US007625703B2

(12) United States Patent
Rothschild et al.

(10) Patent No.: US 7,625,703 B2
(45) Date of Patent: Dec. 1, 2009

(54) CALPASTATIN (CAST) ALLELES

(75) Inventors: Max F. Rothschild, Ames, IA (US); Daniel C. Ciobanu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 428 days.

(21) Appl. No.: 11/565,337

(22) Filed: Nov. 30, 2006

(65) Prior Publication Data
US 2007/0172848 A1 Jul. 26, 2007

Related U.S. Application Data

(63) Continuation of application No. 10/339,279, filed on Jan. 9, 2003, now abandoned.

(60) Provisional application No. 60/347,209, filed on Jan. 9, 2002.

(51) Int. Cl.
*C12Q 1/68* (2006.01)
*C12P 19/34* (2006.01)
*C07H 21/02* (2006.01)

(52) U.S. Cl. .................. 435/6; 435/91.2; 536/23.1

(58) Field of Classification Search ............... None
See application file for complete search history.

(56) References Cited

FOREIGN PATENT DOCUMENTS

WO 02/064820 A1 8/2002

OTHER PUBLICATIONS

Leach LM et al. J. Anim. Sci. (1996) vol. 74, pp. 934-943.*
Janns LLG et al. Genetics (Feb. 1997) vol. 154, pp. 395-408.*
GenBank Locus PGICALPSA (Apr. 27, 1993) GI: 164406 'Pig heart calpastatin gene, complete cds.' from www.ncbi.nlm.nih.gov, printed pp. 1-3.*
Ernst CW et al. Animal Genetics (1998) vol. 29, pp. 212-215.*
Bork et al., "Convergent evolution of similar enzymatic function on different protein folds: The hexokinase, ribokinase, and galactokinase families of sugar kinases", Protein Science, vol. 2, pp. 31-40 (1993).
Ciobanu et al., "Evidence of new appeles in Calpastatin gene associated with meat quality traits in pigs", Growth and meat quality, 75h World Congress on Genetics Applied to Livestock Production, Aug. 19-23, 2002, Montpelier, France, Session 11.
Ciobanu et al., "Genetic variation in two conserved local Romanian pig breeds using type 1 DNA markers", Genet. Sel. Evol., 2001, vol. 33, pp. 417-432, especially pp. 422-423.

Chung, et al., "A DNA polymorphism of the bovine calpastatin gene detectyed by SSCP analysis", Animal Genetics, vol. 30, pp. 66-80 (1999).
Green et al., "Association of a Taq1 calpastatin polymorphism with postmortem measures of beef tenderness in Bos Taurus and Bos indicus-Bos taurus steers and heifers", J. of Animal Science, vol. 74, Suppl 1, p. 111, Abstract No. 23 (1996).
Green et al., "Association of a Taq1 calpastatin polymorphism with postmortem measures of beef tenderness in Charlolais- and Limousin-sired steers and heifers," J. of Animal Science, Vo. 74 (supp. 1) p. 113, Abstract 30 (1996).
Huang et al., "Genetic variations of the porcine PRKAG3 gene in Chinese indigenous pig breeds," Genet. Sel. Evol. 36:481-486 (2004).
Juppner, "Functional properties of PTH/PTHrP receptor", Bone, 17(2):39S-42S (1995).
Lonergan et al., "Relationship of restriction fragment length polymorphism (RFLP)) at the bovine calpastatin locus to calpastatin activity and meat tenderness", J. of Animal Science, 73:3608-3612 (1995).
Maki et al., "Analysis of structure-function relationship of pig calpastatin by expression of mutated cDNAs in *escherichia coli*", J. of Biological Chemistry, 263(21):10254-10261 (1998).
Mummidi et al., "Evolution of human and non-human primate CC chemokine receptor 5 gene and mRNA", J. of Biological Chemistry, 275(25):18946-18961 (2000).
Nonneman, D., et al., "Rapid communication: A polymorphic microsatellite in the promoter region of the bovine calpastatin gene", J. Anim. Sci. 77:3114-3115 (1999).
PIC USA (2003) Insert) Meat Quality: Understanding Industry Measurements and Guidelines. PIC Technical Update. Available at 222.pic.com/usa.
Sensky et al., "Effect of the halothane mutation on t6he calpain-calpastatin system in porcine longissimus muscle", J. of Animal Science, 75(1):173 (1997), Abstract No. 146.
Thisted, Ronald A., "What is a P-value?", Available at 222.statuchicago.edu/~thisted.
Zambonelli et al., "A BglII RFLP at the porcine calpastatin (CAST) locus", Animal Genetics, 26(5):373 (1995).

\* cited by examiner

*Primary Examiner*—Stephen Kapushoc
(74) *Attorney, Agent, or Firm*—McKee, Voorhees & Sease, P.L.C.

(57) ABSTRACT

Disclosed herein are novel alleles characterized by polymorphisms in the CAST gene. The alleles may be used to genetically type animals. In a preferred embodiment, the alleles may be used as markers for animal meat quality and/or growth. Methods for identifying such markers, and methods of screening animals to determine those more likely to produce desired meat quality and/or growth and preferably selecting those animals for future breeding purposes are also disclosed.

6 Claims, 13 Drawing Sheets

TCTCTCGGCCGGGAAGCCAGAAGCAGAGTATCGCCTTCCTCTGCTTCAAC 50

GAGCAAGTCTTCCAGTATGAATCCCACAGAAACCAAGGCTGTAAAAACAG 100

AACCTGAAAAGAAGTCACAATCAACTAAGCCATCTGTGGTTCATGAGAAA 150

AAAACCCAAGAAGTAAAGCCAAAGGAACACCCAGAGCCAAAAAGCCTACC 200

CACGCACTCAGCAGATGCAGGGAGCAAGCGTGCTCATAAAGAAAAGCAG 250

TTTCCAGATCTAaTGAGCAGCCAACATCAGAGAAATCAACAAAACCAAAG 300
          g-engineered ApaLI site

GCTAAACCACAGGACCCGACCCCCAGTGATGGAAAGCTTTCTGTTACTGG 350

TGTATCTGCAGCATCTGGCAAACCAGCTGAGACGAAAAAAGATGATAAAT 400

CATTAACATCGTCTGTACCAGCTGAATCCAAATCAAGTAAACCATCAGGA 450

AAGTCAGATATGGATGCTGCTTTGGATGACTTAATAGACACTTTAGGAGG 500

ACCTGAAGAAACTGAGGAAGATAATACAACATATACTGGACCTGAAGTTT 550

TGGATCCAATGAGTTCTACCTATATAGAGGAATTGGGTAAAAGAGAAGTC 600

ACACTTCCTCCAAaATATAGGGAATTGTTGGATAAAAAGAAGGGATTCC 650

AGTGCCTCCTCCAGACACTTCGAAACCCCTGGGGCCCGATGATGCCATCG 700

ATGCCTTGTCATTAGACTTGACCTGCAGTTCTCCTACAGCTGATGGGAAG 750

AAAACCGAGAAAGAGAAATCTACTGGGGAGGTTTTGAAAGCTCAGTCTGT 800

TGGGGTAATCAgAAGCGCTGCTGCTCCACCCCACGAGAAAAAAGAAGGG 850
      a-Hpy188I

TGGAAGAGGACACGATGAGTGATCAAGCACTGGAGGCTTTGTCAGCTTCC 900

CTGGGCAGCCGGAAGTCAGAACCCGAGCTTGACCTCAGCTCCATTAAGGA 950

AATTGATGAGGCAAAAGCCAAAGAAGAGAAACTAAAGAAGTGTGGTGAAG 1000

ATGACGAAACGGTCCCGCCAGAGTATAGATTGAAACCAGCCATGGATAAA 1050

GATGGAAAACCACTCTTGCCAGAGGCTGAAGAAAAACCCAAGCCCCTGAG 1100

TGAATCAGAACTCATTGACGAACTTTCGGAAGATTTTGACCAGTCTAAGC 1150

GTAAAGAAAAACAATCTAAGCCAACTGAAAAAACAAAAGAGTCTCAGGCC 1200

*Fig. 1A*

```
ACTGCCCCTACTCCTGTGGGAGAGGCCGTGTCTCGGACCTCCTTGTGCTG 1250

TGTGCAGTCGGCACCCCCAAAGCCAGCTACGGGCATGGTGCCAGATGATG 1300

CTGTAGAAGCCTTGGCTGGAAGCCTGGGGAAAAAGGAAGCAGATCCAGAA 1350

GATGGAAAGCCTGTGGAGGATAAAGTCAAGGAGAAAGCCAAAGAAGAGGA 1400

TCGTGAAAAACTTGGTGAAAAGGAAGAAACGATTCCTCCTGATTATAGAT 1450

TAGAAGAGGTCAAGGACAAAGATGGAAAAACTCTCCCGCACAAAGACCCC 1500

AAGGAACCAGTCCTGCCCTTGAGTGAAGACTTCGTCCTTGATGCTTTGTC 1550

CCAGGACTTTGCCGGTCCCCCAGCCgCTTCATCTCTTTTTGAAGATGCTA 1600
                        a-AciI
AACTTTCAGCTGCCGTCTCTGAAGTGGTTTCCCAAACCTCAGCTCCAACC 1650

ACCCACTCTGCAGGTCCACCCCCTGACACTGTGAGTGATGACAAAAAACT 1700

TGACGATGCCCTGGATCAGCTTTCTGACAGTCTGGGGCAAAGACAGCCTG 1750

ACCCAGATGAGAACAAGCCCATAGAGGATAAAGTCAAGGAAAAAGCTGAA 1800

GCTGAACATAGAGACAAGCTGGGAGAAAGAGATGACACTATCCCGCCTGA 1850

ATATAGACATCTCTTGGATAAGGATGAGGAGGGCAAATCAACGAAGCCAC 1900

CCACAAAGAAACCTGAGGCACCAAAGAAACCTGAAGCTGCCCAAGATCCC 1950

ATTGATGCCCTCTCAGGGGATTTTGACAGaTGTCCATCAACTACAGAAAC 2000
                              c-PvuII
CTCAGAGAACACAACAAAGGACAAAGACAAGAAGACGGCTTCCAAGTCCA 2050

AAGCACCCAAGAATGGGGGTAAAGCAAAGGATTCCACAAAGGCAAAGGAG 2100

GAAACTTCCAAACAAAAATCTGATGGAAAGAGTACAAGTTAAAAGTTCAC 2150

ACTATTTTC                                      2159
```

*Fig. 1B*

```
MNPTETKAVKTEPEKKSQSTKPSVVHEKKTQEVKPKEHPEPKSLPTHSAD    50
DomainL
AGSKRAHKEKAVSRSSEQPTSEKSTKPKAKPQDPTPSDGKLSVTGVSAAS   100

GKPAETKKDDKSLTSSVPAESKSSKPSGKSDMDAALDDLIDTLGGPEETE   150
                          domainLdomain1
EDNTTYTGPEVLDPMSSTYIEELGKREVTLPPKYRELLDKKEGIPVPPPD   200

TSKPLGPDDAIDALSLDLTCSSPTADGKKTEKEKSTGEVLKAQSVGVIRS   250
                                                Hpy188I-K
AAAPPHEKKRRVEEDTMSDQALEALSASLGSRKSEPELDLSSIKEIDEAK   300
            Domain1domain2
AKEEKLKKCGEDDETVPPEYRLKPAMDKDGKPLLPEAEEKPKPLSESELI   350

DELSEDFDQSKRKEKQSKPTEKTKESQATAPTPVGEAVSRTSLCCVQSAP   400

PKPATGMVPDDAVEALAGSLGKKEADPEDGKPVEDKVKEKAKEEDREKLG   450
  Dom2domain3
EKEETIPPDYRLEEVKDKDGKTLPHKDPKEPVLPLSEDFVLDALSQDFAG   500

PPAASSLFEDAKLSAAVSEVVSQTSAPTTHSAGPPPDTVSDDKKLDDALD   550
    T-AciI                              Domain3domain4
QLSDSLGQRQPDPDENKPIEDKVKEKAEAEHRDKLGERDDTIPPEYRHLL   600

DKDEEGKSTKPPTKKPEAPKKPEAAQDPIDALSGDFDRCPSTTETSENTT   650
                                     S-PvuII
KDKDKKTASKSKAPKNGGKAKDSTKAKEETSKQKSDGKSTS*           692
```

*Fig. 1C*

11　　　12　　　22
  182bp
  136bp
  46bp
*Fig.2A*

AAATCTACTGGAGAGGTTTTGAAAGCTCAGTCTGTTGGGGTAATCAaAAG
CGCTGCTGCTCCACCCCACGAGAAAAAAGAAGGGTGGAAGAGGTATAAA
TCATTACTTCTTTGCAACGAAGCATGGTCCGCCTGACAGCAGATGCTTTC
CTGAGGCTTATGGAACTGATTCGGGAGAAGTCCGATTGTGCATCACACTT
GATGAGTGTCTTTGCGCTCCTGGTCCTGTGTGGAGTAGTGAAACCAGTCA
GGGTTCACTCGGTCATCTCCAGGCAGGCCTTCTCTTTCTGCAAATGCTTG
TGGGTGATTTCAGCACACTTGCCTTGATTGTGGAGTAAGACTATCTCAAG
ATTCTACTGCTCAGAAGGGCAGGACCCCAGAGCAGCTGCACTCTTGCTT

*Fig. 2B*

11 12 22
  539bp
  498bp
  41bp
*Fig.3A*

AGGGCAAATCAACGAAGCCACCCACAAAGAAACCTGAGGCACCAAAGGTA
AATACTTTTTTACACTCTTGCTGCAACTCTTAAATTTTAGAAATAGAAA
ATTTATTGAATTCTTACCTTGTGCTTTATGATCCCAAAGGGTTTGTATAA
GAATGTATTATTTCTGTTTTCCCGAGAGCCATTCAAGATAGGCAGTTCCA
TTTTCCAGATTAGAAAATTGAAGCTGAGYGAATACTAAGCAATTTGTATA
AAAGAGTAGAAGAAAATAGAGCTGTCAAGATTTTCCTGTTTTAATATCTC
TTTTGTAATACACTACTTTGTTAGGAAAGGAATGACAGCAAGGCTTTATT
TTAAACAAACCTATTTTCAGGGATATGGGAAAATATCCCACAGAGCATTC
TCTCCTTTGCCTCTTCATTGATGGCCATTTCTATTAATATCTCAGAAACC
TGAAGCTGCCCAAGATCCCATTGATGCCCTCTCAGGGGATTTTGACAGaT
GTCCATCAACTACAGAACCTCAGAGAACACAACAAAGG

*Fig.3B*

 
 
 
*Fig.4A*

AGACTTCGTCCTTGATGCTTTGTCCCAGGACTTTGCCGGTCCCCCAGCCgCTTCATCTCTTGTAAG
TCTTTGGAGATTCCTGGTTTAATTTCCTTAGTTTTAGAGTAGCACGAAATAGATGGAAACTTGGG
ACTTAGAATCTGATGTGGGAGCTGAGGAAACAAAATTAATGGCCCTCAACCCATCATAGCCATT
A

*Fig.4B*

11　　　12　　　22
　　　　　535bp
　　　　　506bp
　　　　　29bp
*Fig.5A* a) original sequence 1   agccatctgt ggttcatgag aaaaaaaccc aagaagtaaa gccaaaggaa cacccagagc
61  caaaaagcct acccacgcac tcagcagatg cagggagcaa gcgtgctcat aaagaaaaag
121 cagtttccag atctartgag cagccaacat cagagaaatc aaca b) modified sequence using an engineered reverse primer C28MR.
1   agccatctgt ggttcatgag aaaaaaaccc aagaagtaaa gccaaaggaa cacccagagc
62  caaaaagcct acccacgcac tcagcagatg cagggagcaa gcgtgctcat aaagaaaaag
121 cagtttccag atctart<u>gca</u> <u>cagccaacat cagaga aataaaaa</u>

*Fig.5B*

```
Bost     ------------------------------------------------------------C
Suss     AGCCATCTGTGGTTCATGAGAAAAAAACCCAAGAAGTAAAGCCAAAGGAACACCCAGAGC
                                                                    *

Bost     CAAAAAGCCTACCCAAGCACTCATCAGATACAGGAAGCAAGCATGCTCCTAAGGAAAAAG
Suss     CAAAAAGCCTACCCACGCACTCAGCAGATGCAGGGAGCAAGCGTGCTCATAAAGAAAAAG
         **************  ******  ***** ****  ****** * ***** *** ******

Bost     CCGTTTCCAAATCAAGYGAGCAGCCACCATCAGAGAAATCAACAAAACCAAAG
Suss     CAGTTTCCAGATCTARTGAGCAGCCAACATCAGAGAAATCAACA---------
         * ******* *** * ********** *****************
```

*Fig.7*

CALPASTATIN (CAST) ALLELES

CROSS-REFERENCE TO RELATED APPLICATIONS

This is a continuation application of U.S. patent application Ser. No. 10/339,279 filed Jan. 9, 2003, which is a non-provisional application claiming benefit under 35 U.S.C. § 119(e) of provisional application Ser. No. 60/347,209 filed Jan. 9, 2002.

GRANT REFERENCE

This invention was supported at least in part by USDA/CREES contract number 2001-31200-06019 (IAHAEES project number IOW03600). The United States government may have certain rights in this invention.

FIELD OF THE INVENTION

This invention relates generally to the detection of genetic differences among animals. More particularly, the invention relates to genetic markers that are indicative of heritable phenotypes associated with improved growth, meat quality and other such economic traits in animals. Methods and compositions for use of these markers in genotyping of animals and selection are also disclosed as well as novel sequences.

BACKGROUND OF THE INVENTION

Genetic differences exist among individual animals as well as among breeds which can be exploited by breeding techniques to achieve animals with desirable characteristics. For example, Chinese breeds are known for reaching puberty at an early age and for their large litter size, while American breeds are known for their greater growth rates and leanness. However, heritability for desired traits is often low, and standard breeding methods which select individuals based upon phenotypic variations do not take fully into account genetic variability or complex gene interactions which exist.

Restriction fragment length polymorphism (RFLP) analysis has been used by several groups to study pig DNA. Jung et al., Theor. Appl. Genet., 77:271-274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science*, Mar. 26-28, 1990, incorporated herein by reference, reports on the polymorphism of swine major histocompatibility complex (MHC) genes for Chinese pigs, also demonstrated by RFLP analysis. Jung et al., *Theor. Appl. Genet.*, 77:271-274 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526 issued to Rothschild et al. disclose a polymorphism in the pig estrogen receptor gene which is associated with larger litter size, the disclosure of which is incorporated herein by reference. U.S. Pat. No. 5,935,784 discloses polymorphic markers in the pig prolactin receptor gene which are associated with larger litter size and overall reproductive efficiency.

The quality of raw pig meat is influenced by a large number of genetic and non-genetic factors. The latter include farm, transport, slaughter and processing conditions. Meat scientists have performed a substantial amount of research on these factors, which has led to considerable quality improvement. Part of the research has also been dedicated to the genetic background of the animals, and several studies have revealed the importance of genetic factors. This has made the industry aware that selective breeding of animals and the use of gene technology can play an important role in enhancing pork quality.

Information at DNA level can help to fix a specific major gene, but it can also assist the selection of a quantitative trait for which we already select. Molecular information in addition to phenotypic data can increase the accuracy of selection and therefore the selection response. The size of the extra response in such a Marker Assisted Selection (MAS) program has been considered by many workers from a theoretical point of view. In general terms, MAS is more beneficial for traits with a low heritability and which are expensive to measure phenotypically. Although traits such as meat quality and/or growth are not typically considered in this way there are still significant advantages for the use of markers for these traits. For example, Meuwissen and Goddard considered the impact of MAS for different types of traits. The biggest impacts were for traits such as meat quality, where the trait is measured after slaughter and an additional response of up to 64% could be achieved with the incorporation of marker information. This figure was relatively small, 8%, for growth traits, that can be measured on the live animal. However, once the association has been demonstrated this marker information can be used before the animals are tested or selected phenotypically (see below) and in this situation a response of up to 38% was predicted.

Indeed, the best approach to genetically improve economic traits is to find relevant DNA-markers directly in the population under selection. Phenotypic measurements can be performed continuously on some animals from the nucleus populations of breeding organizations. Since a full assessment of most of these traits can only be done after slaughter, the data must be collected on culled animals and cannot be obtained on potential breeding animals.

This phenotypic data is collected in order to enable the detection of relevant DNA markers, and to validate markers identified using experimental populations or to test candidate genes. Significant markers or genes can then be included directly in the selection process. An advantage of the molecular information is that we can obtain it already at very young age of the breeding animal, which means that animals can be preselected based on DNA markers before the growing performance test is completed. This is a great advantage for the overall testing and selection system.

It can be seen from the foregoing that a need exists for identification of markers which may be used to improve economically beneficial characteristics in animals by identifying and selecting animals with the improved characteristics at the genetic level.

An object of the present invention is to provide genetic markers based on or within the calpastatin (CAST) gene which are indicative of favorable economic characteristics such as meat quality and/or growth.

Another object of the invention is to provide an assay for determining the presence of these genetic markers.

A further object of the invention is to provide a method of evaluating animals that increases accuracy of selection and breeding methods for the desired traits.

Yet another object of the invention is to provide a PCR amplification test which will greatly expedite the determination of presence of the markers.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

This invention relates to the discovery of alternate forms of the calpastatin or CAST gene which are useful to genetically type animals. The may be used for following lineages in breeding, or in a preferred embodiment the novel gene forms may be used as genetic markers associated with phenotypic differences which may be selected for or against. In an even more preferred embodiment the phenotypic differences are meat quality and growth traits. To the extent that this gene is conserved among species and animals, and it is expected that the different alleles disclosed herein will also correlate with variability in this gene in other economic or meat-producing animals such as bovine, sheep, chicken, etc.

To achieve the objects and in accordance with the purpose of the invention, as embodied and broadly described herein, the present invention provides the discovery of alternate genotypes which provide a method for genetically typing animals, preferably for screening animals to determine those more likely to possess favorable meat quality and/or growth traits or to select against pigs which have alleles indicating less favorable growth and/or meat quality traits. As used herein "favorable growth or meat quality trait" means a significant improvement (increase or decrease) in one of many measurable meat quality or growth traits above the mean of a given population, so that this information can be used in breeding to achieve a uniform population which is optimized for meat quality and/or growth, this may include an increase in some traits or a decrease in others depending on the desired characteristics. These factors for meat quality which may be considered include but are not limited to the following:

Loin Minolta Lightness (L*): The range of 43-47 units (from darker to lighter color) is acceptable, but L* of 43 is better; i.e., has higher economic value, in general in this range (this may be dependent upon market, for example in Japan darker pork is preferred).

Loin Japanese Color Score (JCS): The range of 2.5-5.0 units (from lighter to darker color) is acceptable, but JCS of 3-4 is better.

Loin Marbling (level of intramuscular fat): Generally, higher marbling is better as it is associated with improved meat eating quality characteristics.

Loin pH: (ultimate meat acidity measured 24 hours post-mortem; this attribute is the single most important trait of pork quality);—The range of 5.50-5-80 is desirable, but 5.80 is better as it positively influences the color and (low) purge of the meat.

Ham Minolta lightness (L*) The range of 43-52 units is acceptable, but lower (43) is better.

Ham pHu: higher; i.e., 5.80, is better.

Drip loss or purge: the range of 1%-3% is acceptable, but lower is better.

These measures of meat quality are examples of those generally accepted by those of skill in the art. For a review of meat quality traits the following may be consulted: Sosnicki, A. A., E. R. Wilson, E. B. Sheiss, A. deVries, 1998 "Is there a cost effective way to produce high quality pork?", *Reciprocal Meat Conference Proceedings*, Vol. 51.

Growth can be measured by any of a number of standard means such as average daily gain, weight at slaughter, etc.

Thus, the present invention provides a method for screening pigs to identify those more likely to produce favorable meat quality and/or growth, and/or those less likely to produce favorable meat quality and/or growth to optimize breeding and selection techniques for the best meat quality and/or growth.

Methods for assaying for these traits generally comprises the steps 1) obtaining a biological sample from a pig; and 2) analyzing the genomic DNA or protein obtained in 1) to determine which CAST allele(s) is/are present. Also included herein are haplotype data which allows for a series of polymorphisms in the CAST gene to be combined in a selection or identification protocol to maximize the benefits of each of these markers.

Since several of the polymorphisms involve changes in amino acid composition of the CAST protein, assay methods may even involve ascertaining the amino acid composition of the CAST protein. Methods for this type or purification and analysis typically involve isolation of the protein through means including fluorescence tagging with antibodies, separation and purification of the protein (i.e. through reverse phase HPLC system), and use of an automated protein sequencer to identify the amino acid sequence present. Protocols for this assay are standard and known in the art and are disclosed in Ausubel et. al.(eds.), Short Protocols in Molecular Biology Fourth ed. John Wiley and Sons 1999.

In a preferred embodiment a genetic sample is analyzed. Briefly, a sample of genetic material is obtained from an animal, and the sample is analyzed to determine the presence or absence of a polymorphism in the CAST gene that is correlated with improved meat quality and/or growth or both traits depending on the gene form.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In a preferred embodiment the polymorphism is a restriction fragment length polymorphism and the assay comprises identifying the CAST gene from isolated genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from a CAST gene that is either known to have or not to have the desired marker. If an animal tests positive for the markers, such animal can be considered for inclusion in the breeding program. If the animal does not test positive for the marker genotype the animal can be culled from the group and otherwise used. Use of haplotype data can also be incorporated with the screening for multiple alleles for different aspects of meat quality and/or growth.

In a most preferred embodiment the gene is isolated by the use of primers and DNA polymerase to amplify a specific region of the gene which contains the polymorphism. Next the amplified region is digested with a restriction enzyme and fragments are again separated. Visualization of the RFLP pattern is by simple staining of the fragments, or by labeling the primers or the nucleoside triphosphates used in amplification.

In another embodiment, the invention comprises a method for identifying a genetic marker for meat quality and/or growth in a particular population. Male and female animals of the same breed or breed cross or similar genetic lineage is bred, and meat quality and/or growth produced by each pig is determined. A polymorphism in the CAST gene of each pig is identified and associated with the meat quality and/or growth. Preferably, RFLP analysis is used to determine the polymorphism.

In another embodiment, the invention comprises a method for identifying a genetic marker for meat quality and/or growth in any particular economic animal other than a pig. Based upon the highly conserved nature of this gene among different animals and the location of the polymorphisms within these highly conserved regions, is it expected that with no more than routine testing as described herein this marker can be applied to different animal species to select for meat quality and/or growth based on the teachings herein. Male and female animals of the same breed or breed cross or similar genetic lineage are bred, and the meat quality and/or growth produced by each animal is determined and correlated. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. In this case the Reference CAST sequence. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al, *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information on the world wide web at blast.ncbi.nlm.nih.gov/Blast.cgi.

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e)(I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

These programs and algorithms can ascertain the analogy of a particular polymorphism in a target gene to those disclosed herein. It is expected that this polymorphism will exist in other animals and use of the same in other animals than disclosed herein involved no more than routine optimization of parameters using the teachings herein.

It is also possible to establish linkage between specific alleles of alternative DNA markers and alleles of DNA markers known to be associated with a particular gene (e.g. the CAST gene discussed herein), which have previously been shown to be associated with a particular trait. Thus, in the present situation, taking the CAST gene, it would be possible, at least in the short term, to select for animals likely to produce desired meat quality and/or growth, or alternatively against pigs likely to produce less desirable meat quality and/or growth, indirectly, by selecting for certain alleles of a CAST associated marker through the selection of specific alleles of alternative chromosome markers. As used herein the term "genetic marker" shall include not only the polymorphism disclosed by any means of assaying for the protein changes associated with the polymorphism, be they linked markers, use of microsatellites, or even other means of assaying for the causative protein changes indicated by the marker and the use of the same to influence the meat quality and/or growth of an animal.

As used herein, often the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example on the world wide web at Darwin.bio.geneseo.edu which can give restriction enzymes upon analysis of a sequence and the polymorphism to be identified. In fact as disclosed in the teachings herein there are numerous ways of identifying a particular polymorphism or allele with alternate methods which may not even include a restriction enzyme, but which assay for the same genetic or proteomic alternative form.

In yet another embodiment of this invention novel porcine nucleotide sequences have been identified and are disclosed which encode porcine CAST. The cDNA of the porcine CAST gene as well as some intronic DNA sequences are disclosed. These sequences may be used for the design of primers to assay for the SNP's of the invention or for production of recombinant CAST. The invention is intended to include these sequences as well as all conservatively modified variants thereof as well as those sequences which will hybridize under conditions of high stringency to the sequences disclosed. The term CAST as used herein shall be interpreted to include these conservatively modified variants as well as those hybridized sequences.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C.

Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m = 81.5°C. + 16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acids Probes*, Part I, Chapter 2, Ausubel, et al., Eds., Greene Publishing and Wiley-Interscience, New York (1995).

The accompanying figures, which are incorporated herein and which constitute a part of this specification, illustrates one embodiment of the invention and, together with the description, serve to explain the principles of the invention.

DESCRIPTION OF THE FIGURES

FIGS. 1a and 1b are the porcine skeletal calpastatin cDNA sequence (SEQ ID NO: 1) including the polymorphisms (SEQ ID NO: 3, 5, 7, and 9) of the invention. FIG. 1c is the amino acid sequence (SEQ ID NO:2).

FIG. 2a is a sketch of the expected banding pattern of the different genotypes for the Hpy188I polymorphism. FIG. 2b is the sequence around the Hpy188I polymorphism (SEQ ID NO:21).

FIG. 3a is a sketch of the expected banding pattern of the different genotypes for the PvuII polymorphism. FIG. 3b is the sequence around the PvuII polymorphism (SEQ ID NO:22).

FIG. 4a is a sketch of the expected banding pattern of the different genotypes for the AciI polymorphism. FIG. 4b is the sequence around the AciI polymorphism (SEQ ID NO:23).

FIG. 5a is a sketch of the expected banding pattern of the different genotypes for the ApaLI polymorphism. FIG. 5b is the sequence around the ApaLI polymorphism (SEQ ID NO:24 and 25).

FIG. 7 is an alignment between the *Bos taurus* (SEQ ID NO: 19) and *Sus scrofa* (SEQ ID NO:20) sequences for the exon 6 polymorphism using the Clustal L program. The polymorphism is in the same codon for each. The *Bos taurus* nucloetide change is in the second nucleotide triplet codon, while in the *Sus scrofa* the change is in the last nucleotide triplet codon. Both changes result in a synonomous amino acid substitution.

DETAILED DESCRIPTION OF THE INVENTION

Figure 6:
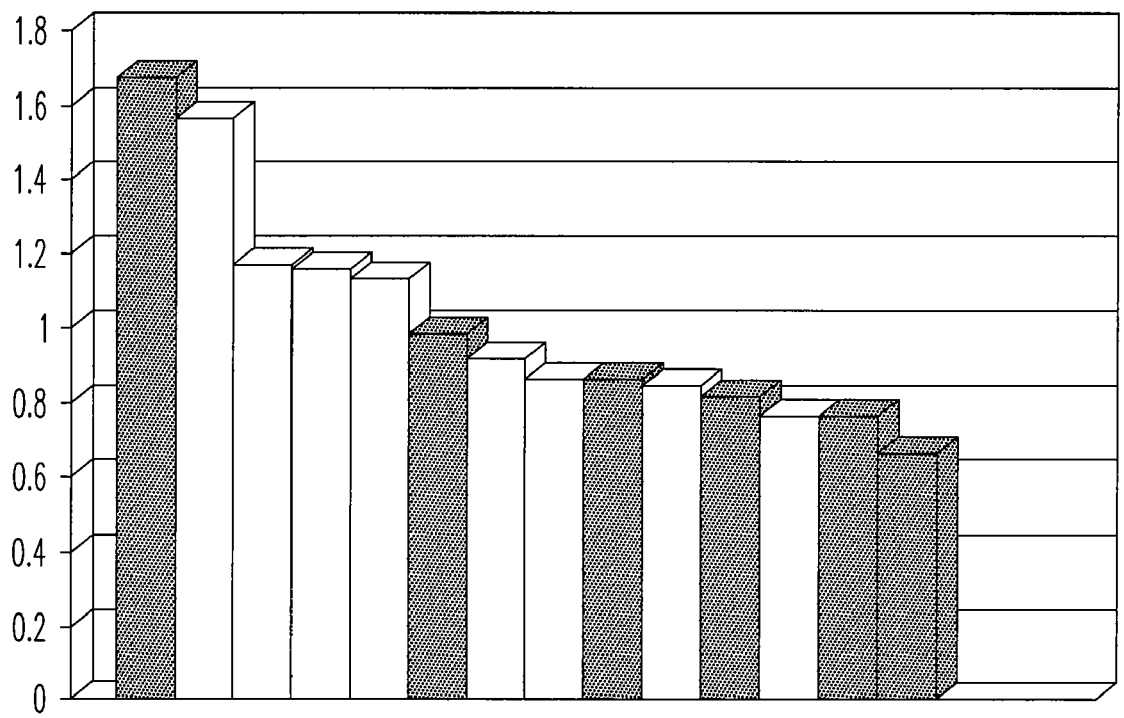
FIG. 6 is a graph showing calpastin activity at 24 hr and cast Hpy188I genotypes 11 and 12.

Reference will now be made in detail to the presently referred embodiments of the invention, which together with the following examples, serve to explain the principles of the invention.

In mammalian skeletal and cardiac muscle, calcium activated proteinases have been implicated in processes that regulate limited proteolysis of myofibrillar and cytoskeletal proteins and maintain the intracellular architecture of the muscle fiber. Many muscle wasting diseases such as muscular dystrophy are accompanied by changes in calpain (calcium-dependent cysteine protease) activity. Calpastatin (CAST) is a calpain specific endogenous protein inhibitor that is coexpressed with calpain. CAST has been hypothesized to be involved in muscle protein degradation in living tissue, and has also been shown to play a key role in post mortem tenderization of meat. Calpastatins isolated from different tissues are heterogenous in size due to alternative splicing of gene transcripts as well as posttranslational processing. The physiological significance of calpastatin diversity is not understood but is postulated to be related to intracellular compartmentalization or differential inhibitor specificity against calpain isoforms. There are four domains in the CAST protein, each one having inhibitory function.

According to the invention, applicants have identified several different alleles of the CAST gene which are correlated with improved growth and meat quality in animals. Applicants have also identified novel porcine skeletal cDNA sequences.

FIGS. 1a and 1b depict the Calpastatin cDNA sequence SEQ ID NO: 1 and depicts the alternate polymorphisms of the invention, (SEQ ID NO: 3, 5, 7, and 9),. Figure 1c depicts the amino acid sequence of porcine skeletal CAST SEQ ID NO:2 showing the alternate forms (SEQ ID NOS 4, 6, 8, and 10). These new markers have been shown to correlate with meat firmness, meat juiciness, meat tenderness, average Instron force, average drip loss, weight before slaughter, loin weight, loin pH, and ham pH, hpromeat (Henessey probe loin depth). According to the invention, the association of these polymorphisms with theses trait(s) enables genetic markers to be identified for specific breeds or genetic lines or animals, with favorable meat quality and or growth early in the animals life.

One of the single nucleotide polymorphisms identified according to the invention represents a shift from an arginine codon (AAA, Allele 2) to lysine (AGA, Allele 1) in exon 13 domain 1 of the CAST gene (SEQ ID NO: 5 and 6)(position 812 of the cDNA sequence, FIG. 1). This polymorphism was shown to have effects on subjective juciness, firmness, instron force, drip loss, cooking loss, crumbliness, fibrosity, guminess, hardness, acceptance, loinminl, loinpH, days on test, hamminl, boneless weight of the loin, LDG, and TDG. There was also several assocaitions with growth traits including live daily gain, daily gain on test, and weight at the end of test. According to one embodiment of the invention, a PCR-RFLP test has been developed to identify the presence of either of these particular alleles in a genetic sample using the restriction enzyme Hpy188I.

Yet another single nucleotide polymorphism identified according to the invention represents a change from an arginine codon (AGA) to a serine codon (AGC Allele 1) in exon 28 (domain 4) of the CAST gene (SEQ ID NO: 9 and 10) (position 1980 of the cDNA sequence, FIG. 1). Variation at this position was correlated with subjective juciness, firmness, instron force, drip loss, cumbliness, fibrosity, guminess, hardness, acceptance, loinminl, loin pH, hpromeat, aloca backfat, days on test, drip percentage, US_MD, and bone in weight of the ham. There was also an asociation with growth traits such as live daily gain, daily gain on test, Henessey probe loin depth, and weight at the end of test.

According to one embodiment of the invention, a PCR-RFLP test was developed to identify the presence of one of these particular alleles in a genetic sample using the restriction enzyme PvuII.

Another single nucleotide polymorphism identified according to the invention represents a change from a threonine codon (ACT, Allele 1) to an alanine codon (GCT) in exon 22 (domain 3) of the CAST gene (SEQ ID NO:7 and 8)(position 1576 of the cDNA sequence, FIG. 1). According to yet anther embodiment of the invention, a PCR-RFLP test was developed to identify the presence of one of these particular alleles in a genetic sample using the restriction enzyme AciI.

Yet another single nucleotide polymorphism identified according to the invention results in a change from a asparagine codon (AAT, Allele 1) to a serine codon (AGT) in exon 6 (domain L) of the CAST gene (SEQ ID NO:3 and 4)(position 263 of the cDNA sequence, FIG. 1). A test for this polymorphism was developed using the restriction enzyme ApaLI. This polymorphism was found to be in complete linkage disequilibrium with the Hpy188I marker. Also according to the invention, a polymorphism in the same codon was found to be present in cattle. FIG. 6 depicts the Clustal L alignment of the *Bos taurus* (cow) and *Sus scrofa* (pig) exon 6 sequences. Due to the highly conserved nature of this gene it is expected that the polymorphisms disclosed herein, particularly in that they all exist in the coding regions of the gene will be present in other animals, breeds, lines, or populations.

Further, haplotype analysis was conducted to identify favorable combinations of the markers identified in CAST gene and sufficiently informative to be able to detect the poissible effect of them.

The invention thus relates to genetic markers for economically valuable traits in animals. The markers represent alleles that are associated significantly with a meat quality and/or growth trait and thus provides a method of screening animals to determine those more likely to produce desired meat quality and/or growth (levels of one or all of these) when bred by identifying the presence or absence of a polymorphism in the CAST gene that is so correlated.

Thus, the invention relates to genetic markers and methods of identifying those markers in an animal of a particular animal, breed, strain, population, or group, whereby the animal is more likely to yield meat of desired meat quality and/or growth.

Any method of identifying the presence or absence of these markers may be used, including for example single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, micro-array-type detection of the CAST gene, or other linked sequences of the CAST gene. Also within the scope of the invention includes assaying for protein conformational or sequences changes which occur in the presence of this polymorphism. The polymorphism may or may not be the causative mutation but will be indicative of the presence of this change and one may assay for the genetic or protein bases for the phenotypic difference.

The following is a general overview of techniques which can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W.H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the CAST gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655-658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 μl) in a buffer of 50 mM Tris-(pH 8.3), 50 mM KCl 1.5 mM $MgCl_2$, 0.5% Tween 20, 0.5% NP40 supplemented with 100 μg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten μl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H. A. (ed.), Stockton Press, New York, which is incorporated herein by reference. PCR can be employed to amplify target regions in very small numbers of cells (1000-5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N. H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63-67; and Radding, 1982, Ann. Rev. Genetics 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427-2448 (1989).

Allele Specific Oligonucleotide Screening Methods

Further diagnostic screening methods employ the allele-specific oligonucleotide (ASO) screening methods, as described by Saiki et al., Nature 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wild-type allele.

Ligase Mediated Allele Detection Method

Target regions of a test subject's DNA can be compared with target regions in unaffected and affected family members by ligase-mediated allele detection. See Landegren et al., Science 241:107-1080 (1988). Ligase may also be used to detect point mutations in the ligation amplification reaction described in Wu et al., Genomics 4:560-569 (1989). The ligation amplification reaction (LAR) utilizes amplification of specific DNA sequence using sequential rounds of template dependent ligation as described in Wu, supra, and Barany, Proc. Nat. Acad. Sci. 88:189-193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501-527 (1986), and Myers et al., in Genomic Analysis, A Practical Approach, K. Davies Ed. IRL Press Limited, Oxford, pp. 95-139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at the CAST locus can be differentiated using single-strand conformation polymorphism analysis, which identifies base differences by alteration in electrophoretic migration of single stranded PCR products, as described in Orita et al., Proc. Nat. Acad. Sci. 85:2766-2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., Am. J. Hum. Genet. 48:212-222 (1991). In another method, differences between target sequences can be detected by enzymatic cleavage of mismatched base pairs, as described in Nelson et al., Nature Genetics 4:11-18 (1993). Briefly, genetic material from an animal and a phenotypicallt different family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with CAST polymorphisms.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology on the world wide web at twt.com.

Non-PCR Based DNA Diagnostics

The identification of a DNA sequence linked to CAST can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where CAST resides, and thus defining a genetic marker linked to CAST, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to the invention, polymorphisms in the CAST gene have been identified which have an association with meat quality and/or growth. The presence or absence of the markers, in one embodiment may be assayed by PCR RFLP analysis using the restriction endonucleases and amplification primers may be designed using analogous human, pig or other CAST sequences due to the high homology in the region surrounding the polymorphisms, or may be designed using known CAST gene sequence data as exemplified in GenBank or even designed from sequences obtained from linkage data from closely surrounding genes based upon the teachings and references herein. The sequences surrounding the polymorphism will facilitate the development of alternate PCR tests in which a primer of about 4-30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), "Short Protocols in Molecular Biology, Fourth Edition" John Wiley and Sons 1999. The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate animal DNA, genetically type individual animals, and detect genetic differences in animals. In particular, a sample of genomic DNA may be evaluated by reference to one or more controls to determine if a polymorphism in the CAST gene is present. Preferably, RFLP analysis is performed with respect to the CAST gene, and the results are compared with a control. The control is the result of a RFLP analysis of the CAST gene of a different animal where the polymorphism of the animal's CAST gene is known. Similarly, the CAST genotype of an animal may be determined by obtaining a sample of its genomic DNA, conducting RFLP analysis of the CAST gene in the DNA, and comparing the results with a control. Again, the control is the result of RFLP analysis of the CAST gene of a different animal. The results genetically type the animal by specifying the polymorphism(s) in its CAST genes. Finally, genetic differences among animals can be detected by obtaining samples of the genomic DNA from at least two animals, identifying the presence or absence of a polymorphism in the CAST gene, and comparing the results to trace lineage, to track animals and the like.

These assays are useful for identifying the genetic markers relating to meat quality and/or growth, as discussed above, for identifying other polymorphisms in the CAST gene that may be correlated with other characteristics, such as litter size and for the general scientific analysis of pig genotypes and phenotypes.

The examples and methods herein disclose a certain gene which has been identified to have a polymorphism which is associated either positively or negatively with a beneficial trait that will have an effect on meat quality and/or growth for animals carrying this polymorphism. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism (allele). Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

EXAMPLE 1

CAST Hpy188I PCR-RFLP Test
Hpy188I polymorphism
Exon: 13 (domain 1)
Non-synonymous change: Arg-Lys
Allele 1-Lys (K)-AAA
Allele 2-Arg (R)-AGA

| Primers | | |
|---|---|---|
| CI4F2: | | |
| 5' AAA TCT ACT GGA GAG GTT TTG AA 3' | | SEQ ID NO:11 |
| CI4R2: | | |
| 5' GAC TTC TCC CGA ATC AGT TCC 3' | | SEQ ID NO:12 |

| PCR conditions Mix1 | |
|---|---|
| 10x PCR buffer | 1.0 µl |
| MgCl$_2$ (15 mM) | 1.0 µl |
| dNTPs (2 mM) | 1.0 µl |
| CI4F2 primer (10 pm/µl) | 0.25 µl |
| CI4R2 primer (10 pM/µl) | 0.25 µl |
| Taq polymerase (5 U/µl) | 0.07 µl |
| ddH$_2$0 | 5.43 µl |
| genomic DNA | 1 µl |

Combine the Mix1 and DNA in a reaction tube. Overlay with mineral oil. Run the following PCR program: 94° C. for 4 min.; 35 cycles of 94° C. for 45 sec., 54° C. for 45 sec and 72° C. for 30 sec; followed by a final extension at 72° C. for 12 min.

Check 3 µl of the PCR on a 2% agarose gel to confirm amplification. Product size is 182bp.

Hpy188I digestion:

| | 1X |
|---|---|
| | Volume (µl) |
| NEB Buffer 4 10X* | 1.0 |
| Hyp188I (10 units/□l) | 0.4 |
| ddWater | 5.6 |
| Mix Final Volume | 7.0 |

*NEB

Aliquot 7 µl Hpy188I mix and add 3 µl PCR product.

Incubate at 37° C.

Gel Electrophoresis:
Add 2 µl orange G loading buffer and load on a 4.0% Nusieve/Me (3:1) agarose.

Run at 150V. Products should be resolved in about 30 minutes.

The expected band pattern and sequence around the polymorphism are shown in FIG. 2.

CAST PvuII PCR-RFLP Test
PvuII polymorphism
Exon: 27 (domain 4)
Non-synonymous change: Arg-Ser
Allele 1-Arg (R)— AGA
Allele 2-Ser (S)— AGC

| Primers | |
|---|---|
| CS26F:<br>5' AGG GCA AAT CAA CGA AGC CAC 3' | SEQ ID NO:13 |
| C27R2:<br>5' CCT TTG TTG TGT TCT CTG AGG 3' | SEQ ID NO:14 |

| PCR conditions<br>Mix1 | |
|---|---|
| 10x PCR buffer | 1.0 µl |
| MgCl₂ (15 mM) | 1.0 µl |
| dNTPs (2 mM) | 1.0 µl |
| CS26F primer (10 pm/µl) | 0.25 µl |
| C27R2 primer (10 pM/µl) | 0.25 µl |
| Taq polymerase (5 U/µl) | 0.07 µl |
| ddH₂0 | 5.43 µl |
| genomic DNA | 1 µl |

Combine the Mix1 and DNA in a reaction tube. Overlay with mineral oil. Run the following PCR program: 94° C. for 4 min.; 35 cycles of 94° C. for 45 sec., 54° C. for 45 sec and 72° C. for 30 sec; followed by a final extension at 72° C. for 12 min.

Check 3 µl of the PCR on a 2% agarose gel to confirm amplification. Product size is 539 bp.

PvuII digestion:

| | 1X |
|---|---|
| | Volume (µl) |
| NEB Buffer 2 10X* | 1.0 |
| PvuII (10 units/µl) | 0.4 |
| ddWater | 5.6 |
| Mix Final Volume | 7.0 |

*NEB

Aliquot 7 µl PvuII mix and add 3 µl PCR product.

Incubate at 37° C.

Gel Electrophoresis:

Add 2 µl orange G loading buffer and load on a 4.0% Nusieve/Me (3:1) agarose.

Run at 150V. Products should be resolved in about 30 minutes.

FIG. 3 shows the expected banding pattern and sequence around the PvuII polymorphism.

CAST AciI PCR-RFLP Test

AciI polymorphism

Exon: 22 (domain 3)

Non-synonymous change: Thr-Ala.

Allele 1-Thr (T)-ACT

Allele 2-Ala (A)-GCT

| Primers | |
|---|---|
| CS22F:<br>5' AGA CTT CGT CCT TGA TGC TTT G 3' | SEQ ID NO:15 |
| CS22R:<br>5' TAA TGG CTA TGA TGG GTT GAG G 3' | SEQ ID NO:16 |

| PCR conditions<br>Mix1 | |
|---|---|
| 10x PCR buffer | 1.0 µl |
| MgCl₂ (15 mM) | 1.0 µl |
| dNTPs (2 mM) | 1.0 µl |
| CS22F primer (10 pm/µl) | 0.25 µl |
| CS22R primer (10 pM/µl) | 0.25 µl |
| Taq polymerase (5 U/µl) | 0.07 µl |
| ddH₂0 | 5.43 µl |
| genomic DNA | 1 µl |

Combine the Mix1 and DNA in a reaction tube. Overlay with mineral oil. Run the following PCR program: 94° C. for 4 min.; 35 cycles of 94° C. for 45 sec., 54° C. for 35 sec and 72° C. for 30 sec; followed by a final extension at 72° C. for 12 min.

Check 3 µl of the PCR on a 2% agarose gel to confirm amplification. Product size is 196 bp.

AciI digestion:

| | 1X |
|---|---|
| | Volume (µl) |
| NEB Buffer 3 10X* | 1.0 |
| AciI (10 units/µl) | 0.4 |
| ddWater | 5.6 |
| Mix Final Volume | 7.0 |

*NEB

Aliquot 7 µl AciI mix and add 3 µl PCR product.

Incubate at 37° C.

Gel Electrophoresis:

Add 2 µl orange G loading buffer and load on a 4.0% Nusieve/Me (3:1) agarose.

Run at 150V. Products should be resolved in about 30 minutes.

FIG. 4 shows the expected banding pattern and the sequence around the CAST-AciI polymorphism.

CAST ApaLI PCR-RFLP Test

ApaLI polymorphism

Exon: 6 (domain L)

Non-synonymous change: Ser-Asn

Allele 1-Asn (N)— AAT

Allele 2-Ser (S)— AGT

| Primers | |
|---|---|
| C282F: | |
| 5' GTA AAG CCA AAG GAA CAC CCA G 3' | (SEQ ID NO:17) |
| C28MR: | |
| 5' TTT TTA TTT CTC TGA TGT TGG CTG TGC A 3' | (SEQ ID NO:18) |

| PCR conditions Mix1 | |
|---|---|
| 10x PCR buffer | 1.0 μl |
| MgCl$_2$ (15 mM) | 1.0 μl |
| dNTPs (2 mM) | 1.0 μl |
| C282F primer (10 pm/μl) | 0.25 μl |
| C28MR primer (10 pM/μl) | 0.25 μl |
| Taq polymerase (5 U/μl) | 0.07 μl |
| ddH$_2$0 | 5.43 μl |
| genomic DNA | 1 μl |

Combine the Mix1 and DNA in a reaction tube. Overlay with mineral oil. Run the following PCR program: 94° C. for 4 min.; 35 cycles of 94° C. for 45 sec., 54° C. for 60 sec and 72° C. for 50 sec; followed by a final extension at 72° C. for 12 min.

Check 2 μl of the PCR on a 2% agarose gel to confirm amplification. Product size is 535 bp.

ApaLI digestion.

The reverse primer (C28MR) was modified (engineered) comparing with the original cDNA sequence and a ApaLI restriction site was added in order to be able to differentiate the alleles.

| 1X | |
|---|---|
| | Volume (μl) |
| NEB Buffer 4 10X | 1.0 |
| ApaLI (10 units/μl) | 0.4 |
| BSA 100X | 0.1 |
| ddWater | 5.5 |
| Mix Final Volume | 7.0 |

Aliquot 7 μl ApaLI mix and add 3 μl PCR product. Incubate at 37° C.

Gel Electrophoresis:
  Add 2 μl orange G loading buffer and load on a 4.0% Nusieve/Me (3:1) agarose.
  Run at 150V. Products should be resolved in about 30 minutes.

FIG. 5 shows the expected band pattern and sequence around the CAST ApaLI polymorphism.

EXAMPLE 2

A. CAST linkage mapping

For linkage mapping, the B×Y resource family (Malek et al. 2001) was genotyped using the CAST-MspI marker previously reported by Ernst et al. (1998) and two-point and multipoint linkage analysis was performed using the CRI-MAP program (Green et al. 1990).

The results of the linkage analysis showed that CAST gene was significantly linked to five markers on SSC2 (the two point recombination frequencies and LOD scores are given in parentheses): SW766 (0.02, 112.92), SW1408 (0.12, 67.34), SW2157 (0.15, 25.99) SW1844 (0.27, 13.16) and SW2445 (0.31, 11.36). These results and multipoint linkage analysis show that the CAST gene is most likely located between SW766 and SW1408, at approximately 73.1 Kosambi cM.

B. Polymorphism Discovery

We sequenced the entire CAST gene using RT-PCR and analyzing samples from the B×Y F$_3$ generation family but also samples from Duroc and Meishan pig breeds, in order to find causative polymorphisms responsible for the phenotypic variation in Plant/abbatoir (24 hr) loin Minolta, water holding capacity and firmness in pigs (Malek et al., 2001). The primers used for sequencing of the entire CAST coding region were designed based on the published cDNA sequence of the CAST heart isoform (GenBank Accession no. M20160). We found four unsynonymous substitutions (see FIG. 1).

Unsynonymous Polymorphisms:

1. CAST-Hpy188I:

AGA-AAA: Arg-Lys; position, exon 13 (domain 1);

Pig: Arg/Lys; rabbit, sheep, bovine, human and mouse, cercopithecus: Arg.

2. CAST-AciI

ACT-GCT: Thr-Ala; position, exon 22 (domain 3);

Pig: Ala/Thr; rabbit, human: Ala; sheep and bovine: Thr; mouse: Ile.

3. CAST-PvuII

AGA-AGC: Arg-Ser; position, exon 27 (domain 4);

Pig: Arg/Ser; rabbit, bovine, human, mouse: Ser.

4. CAST-ApaLI

AGT-AAT: Ser-Asn; position, exon 6 (domain L)

The engineered CAST-ApaLI SNP is important because is in complete linkage disequilibrium with CAST-Hpy188I even though there are about 11 kb distance between them based on human genomic sequence. This fact was revealed by genotyping over 200 animals from different commercial lines. CAST-ApaLI SNP could substitute CAST-Hpy188I which has some effects on meat tenderness.

The repetitive multidomain structure of human Calpastatin is disclosed in Takano & Maki, 1999, the disclosure of which is hereby incorporated herein by reference.

The CAST PvuII and AciI are in a very conserved region of the subdomains. CAST Hpy188I is in exon 13 (TVRSAAP) in the second part of subdomain C, domain 1. All four domains have inhibitory functions independently (Maki et al., 1987; Emori et al., 1988). Subdomain B is the inhibitory center (Ma et al., 1993). Subdomains A and C are important for the potential of the inhibition activity of CAST (Maki et al., 1988); Kawasaki et al., 1989; Uemori et al., 1990). Ma et al. (1994) reported that single mutations in the inhibitory center (subdomain B) or even in either subdomains A or C (involved in the potentiation of the inhibition activity) affects CAST activity.

EXAMPLE 3

Association analysis between the CAST unsynonymous polymorphisms and meat quality and growth traits in pigs.

We designed a PCR-RFLP test for each of the unsynonymous polymorphism we discovered and we genotyped samples from the following resources:

a) The $F_2$ generation of the B×Y family.
b) 14 Duroc DNA samples with Calpastatin activity data from *Longisimus dorsi* muscle measured at 0, 6 and 24 hr after slaughter.
c) 64 samples of a $F_1$ generation Duroc×Yorkshire cross with meat quality data.
d) Three PIC commercial populations as follows: Large White and Duroc synthetic based lines and also a Composite line.

a) The $F_2$ generation of the B×Y family was used for an association study between the CAST-Hpy188I and PvuII substitutions with the traits with QTL in the area where CAST was mapped (Table 2 and 15). CAST-AciI was not polymorphic in this population. This polymorphism we found to be highly informative in Meishan breed and the results are shown in Table 2. The table shows that for CAST Hpy188I, the 11 (KK) genotype is associated with a meat less firm, more juicy, tender and easier to chew and a lower average Instron force. Similar results were obtained for CAST PvuII association study (Table 15).

A haplotype analysis was run in order to be able to dissect which polymorphism has real effects on the traits measured. There are 3 haplotypes present: haplotype 1: Hpy188I-1 and PvuII-1; haplotype 2: Hpy188I-2 and PvuII -1; haplotype 3: Hpy188I-2 and PvuII -2 (Table 16). There are significant differences between the effects of haplotype 1 and 3 for juiceness, instron force and chew score. Haplotype 3 is associated with higher average instron force, the meat is less tender and has a higher chew score. For firmness there are significant differences between the effects of haplotype 1 and 2 and between 2 and 3, both sites being involved in the phenotypic variation of this trait.

Using NetPhos2 software a prediction analysis was performed of possible calpastatin phosphorylation substrates recognized by PKA (cAMP-dependent Protein Kinase). PKA phosphorylates calpastatin and agregates it near the nucleus (Alverna et al., 2001). Same authors consider that this intracellular reversible mechanism regulates the level of cytosolic CAST. Based on this, probably during earlier steps of its inactivation calpains can escape calpastatin inhibition. The prediction analysis revealed that PvuII and eApaLI affect two phosphorylation consensus sequences and finally possible change in calpastatin localization and ability to inhibit calpains.

CAST ApaLI is in linkage disequilibrium with Hpy188I even they are at about 11 kb. distance apart based on human CAST genomic DNA sequence. A test for one of these SNPs can be used to genotype actually both.

TABLE 2

Association results between the genotypes of CAST Hpy188I and some meat quality traits in $F_2$ Berkshire x Yorkshire family

| | Least Square Means* | | | |
|---|---|---|---|---|
| Traits | 11(KK) | 12(KR) | 22(RR) | P |
| Firmness | 3.21 [g, e] | 3.44 [h] | 3.43 [f] | 0.0012 |
| | 136 | 233 | 134 | |
| Juiceness | 6.23 [c] | 6.05 [a] | 5.76 [d, b] | 0.0449 |
| | 136 | 228 | 129 | |
| Tenderness | 8.01 [e, a] | 7.74 [d] | 7.75 [b] | 0.1060 |
| | 136 | 228 | 129 | |
| Chew score | 2.32 [a] | 2.51 [b] | 2.54 [b] | 0.1084 |
| | 136 | 228 | 129 | |

TABLE 2-continued

Association results between the genotypes of CAST Hpy188I and some meat quality traits in $F_2$ Berkshire x Yorkshire family

| | Least Square Means* | | | |
|---|---|---|---|---|
| Traits | 11(KK) | 12(KR) | 22(RR) | P |
| Ave Instron Force | 4.39 [c] | 4.45 [c] | 4.63 [d] | 0.0457 |
| | 127 | 213 | 128 | |

*Significant differences:
[a-b] $p < .1$;
[c-d] $p < .05$;
[e-f] $p < .005$,
[g-h] $p < .0005$ b) A total number of 14 Duroc DNA samples with CAST activity data at 0, 6 and 24 hours were genotyped for the CAST-Hpy188I and PvuII. In the case of Hpy188I where we have a similar number of animals in the two genotype classes we identified a small difference between the means in the favor of 11 genotype at 24 hr (Table 3, FIG. 6). For the same polymorphism there were no differences between the 11 and 12 genotypes regarding CAST activity at 0 and 6 hr. The CAST-AciI polymorphism was not informative in this set of samples. See FIG. 6.

TABLE 3

The mean values of the calpastatin activity in two of the CAST Hpy188I and PvuII genotypes.

| | SNP/ | | | | | |
|---|---|---|---|---|---|---|
| | Calpastatin activity 0 hr units/g | | Calpastatin activity 6 hr Units/g | | Calpastatin activity 24 hr units/g | |
| Genotypes | 11 | 12 | 11 | 12 | 11 | 12 |
| Hpy188I | 2.17 | 2.16 | 1.69 | 1.64 | 1.04 | 0.96 |
| n | 8 | 6 | 8 | 5 | 8 | 6 |
| PvuII | 2.20 | 1.99 | 1.67 | 1.72 | 0.97 | 1.27 |
| n | 12 | 2 | 12 | 1 | 12 | 2 | c) A total number of 64 samples from a $F_1$ generation Duroc×Yorkshire cross with meat quality data, were genotyped for the CAST-Hpy188I and PvuII polymorphisms. The CAST-AciI polymorphism was not informative in this set of samples.

Associations were detected between CAST-Hpy188I polymorphism with firmness (P=0.0936), average drip loss at day 1 (P=0.0701) and WBS force at day 3 (P=0.0315) and 5 (P=0.0045) (Table 4). Significant associations were detected between the genotypes of this polymorphism and the traits mentioned before. The highest association was for WBS force at day 5 (P=0.0045). Except the day 7 the highest variability of this trait is at day 5 and there is possible that CAST-Hpy188I to be associated with CAST activity with final effect on meat tenderness.

TABLE 4

Association analysis of CAST Hpy188I marker with meat quality, body composition and growth traits in a $F_1$ Duroc x Yorkshire cross

| Trait | Mean (s.e.) | $\sigma_p$ | No. animals 11 | 12 | 22 | LSmeans (s.e.) 11 | 12 | 22 | Geno P |
|---|---|---|---|---|---|---|---|---|---|
| Live | 250.09 | 9.72 | 27 | 31 | 6 | 253.32 (3.78) | 253.04 (3.46) | 246.85 (10.16) | 0.8722 |
| Hot | 193.49 | 7.67 | 27 | 31 | 6 | 194.70 (2.88) | 195.18 (2.64) | 194.48 (7.74) | 0.9844 |
| Dressing(%) | 0.774 | 0.015 | 27 | 31 | 6 | 0.769 (0.0053) a | 0.771 (0.0049) | 0.787 (0.0143) b | 0.5305 |
| Loin Temp 45 min | 35.831 | 1.38 | 27 | 31 | 6 | 35.27 (0.40) a | 35.78 (0.37) b | 36.79 (1.08) | 0.2797 |
| Loin pH 45 min | 6.244 | 0.22 | 27 | 31 | 6 | 6.26 (0.09) | 6.33 (0.08) | 6.16 (0.23) | 0.6611 |
| Ham pH 45 min | 6.26 | 0.31 | 27 | 31 | 6 | 6.32 (0.11) | 6.39 (0.10) | 6.07 (0.30) | 0.6156 |
| Loin pH 2 hr | 5.88 | 0.32 | 27 | 31 | 6 | 5.86 (0.12) a | 6.00 (0.11) b | 5.71 (0.32) | 0.4172 |
| Ham pH 2 hr | 5.87 | 0.31 | 27 | 31 | 6 | 5.89 (0.12) | 6.00 (0.11) | 5.77 (0.32) | 0.5909 |
| Loin Temp 4 hr | 15.400 | 2.11 | 27 | 31 | 6 | 14.75 (0.59) | 15.06 (0.54) | 16.45 (1.58) | 0.6308 |
| Loin ph 4 hr | 5.76 | 0.27 | 27 | 31 | 6 | 5.79 (0.11) | 5.88 (0.10) | 5.53 (0.28) | 0.4686 |
| Ham temp 4 hr | 21.52 | 2.12 | 26 | 25 | 6 | 21.86 (0.50) c | 21.66 (0.43) a | 19.17 (1.27) d, b | 0.2406 |
| Ham pH 4 hr | 5.65 | 0.21 | 27 | 31 | 6 | 5.70 (0.07) | 5.70 (0.06) | 5.50 (0.18) | 0.6587 |
| Loin Temp 6 hr | 10.682 | 2.70 | 25 | 22 | 5 | 10.24 (0.51) a | 10.42 (0.47) | 12.13 (1.37) b | 0.5245 |
| Loin pH 6 hr | 5.69 | 0.20 | 27 | 31 | 6 | 5.67 (0.08) | 5.75 (0.07) | 5.58 (0.21) | 0.5121 |
| Ham Temp 6 hr | 17.02 | 2.71 | 27 | 31 | 6 | 17.75 (0.42) | 17.31 (0.36) | 17.50 (1.27) | 0.6618 |
| Ham pH 6 hr | 5.56 | 0.13 | 27 | 31 | 6 | 5.54 (0.04) | 5.55 (0.04) | 5.55 (0.11) | 0.9874 |
| Loin pH 24 hr | 5.56 | 0.08 | 27 | 31 | 6 | 5.60 (0.03) a | 5.56 (0.03) b | 5.56 (0.08) | 0.3814 |
| Loin Temp 24 hr | 2.095 | 0.52 | 27 | 31 | 6 | 2.04 (0.11) | 2.15 (0.10) a | 1.77 (0.30) b | 0.4081 |
| Temp BF 24 hr | 2.948 | 0.49 | 27 | 31 | 6 | 3.00 (0.13) | 3.09 (0.12) a | 2.64 (0.35) b | 0.4691 |
| pH BF 24 hr | 5.62 | 0.13 | 27 | 31 | 6 | 5.63 (0.04) | 5.60 (0.04) | 5.67 (0.12) | 0.5856 |
| Temp SM 24 hr | 2.811 | 0.53 | 27 | 31 | 6 | 2.84 (0.14) | 2.93 (0.13) | 2.47 (0.38) | 0.5354 |
| pH SM 24 hr | 5.60 | 0.13 | 27 | 31 | 6 | 5.60 (0.05) | 5.58 (0.04) | 5.59 (0.12) | 0.8663 |
| Last rib fat | 0.914 | 0.15 | 27 | 31 | 6 | 0.937 (0.041) | 0.964 (0.038) a | 0.819 (0.111) b | 0.4933 |
| NPPC Color | 2.55 | 0.60 | 27 | 31 | 6 | 2.42 (0.21) a | 2.67 (0.20) b | 2.74 (0.58) | 0.4841 |
| Marbling | 1.633 | 0.58 | 27 | 31 | 6 | 1.65 (0.17) a | 1.83 (0.16) b | 1.39 (0.46) | 0.4549 |
| JCS | 2.383 | 0.58 | 27 | 31 | 6 | 2.199 (0.20) | 2.390 (0.18) | 2.453 (0.53) | 0.5960 |
| LD L | 49.69 | 3.31 | 27 | 31 | 6 | 50.49 (1.22) | 49.70 (1.12) | 47.87 (3.28) | 0.6906 |
| Ld a | 4.12 | 1.14 | 27 | 31 | 6 | 4.64 (0.37) a | 4.21 (0.34) b | 3.80 (1.00) | 0.4363 |
| LD b | 10.62 | 1.08 | 27 | 31 | 6 | 11.13 (0.35) a | 10.84 (0.32) a | 9.38 (0.94) b | 0.2694 |
| LD L* | 56.59 | 3.19 | 27 | 31 | 6 | 57.36 (1.18) | 56.59 (1.08) | 54.87 (3.16) | 0.6860 |
| Ld a* | 3.17 | 1.23 | 27 | 31 | 6 | 3.69 (0.39) a | 3.27 (0.36) b | 2.93 (1.06) | 0.5109 |
| SM L | 44.92 | 2.64 | 27 | 31 | 6 | 44.45 (0.94) | 45.13 (0.86) | 44.93 (2.53) | 0.7626 |
| SM a | 6.73 | 1.27 | 27 | 31 | 6 | 7.28 (0.39) a | 6.92 (0.36) a | 5.16 (1.06) b | 0.2132 |
| SM b | 10.44 | 0.99 | 27 | 31 | 6 | 10.60 (0.33) a | 10.65 (0.30) a | 9.37 (0.87) b | 0.4897 |
| SM L* | 51.83 | 2.67 | 27 | 31 | 6 | 51.34 (0.95) | 52.03 (0.87) | 51.88 (2.56) | 0.7595 |
| SM a* | 6.46 | 1.47 | 27 | 31 | 6 | 7.11 (0.45) a | 6.64 (0.41) b, a | 4.73 (1.22) b | 0.2104 |
| SM b* | 15.90 | 1.43 | 27 | 31 | 6 | 16.23 (0.43) a | 16.21 (0.40) a | 14.13 (1.17) b | 0.3352 |
| BF L | 45.87 | 3.70 | 27 | 31 | 6 | 45.98 (1.36) a | 44.39 (1.25) b | 45.64 (3.66) | 0.4920 |
| BF a | 7.83 | 1.29 | 27 | 31 | 6 | 8.47 (0.39) | 8.12 (0.35) | 7.36 (1.04) | 0.5067 |
| BF b | 10.93 | 1.24 | 27 | 31 | 6 | 11.13 (0.43) | 10.71 (0.39) | 10.18 (1.15) | 0.5258 |
| BF L* | 52.79 | 3.69 | 27 | 31 | 6 | 52.85 (1.40) a | 51.27 (1.23) b | 52.57 (3.62) | 0.4842 |
| BF a* | 7.61 | 1.46 | 27 | 31 | 6 | 8.35 (0.42) | 8.06 (0.38) | 7.17 (1.13) | 0.5956 |
| BF b* | 16.57 | 1.65 | 27 | 31 | 6 | 16.88 (0.54) | 16.42 (0.49) | 15.29 (1.44) | 0.5092 |
| Drip Loss Day 1-5 | 0.0194 | 0.0067 | 27 | 31 | 6 | 0.020 (0.0015) a | 0.019 (0.0013) b | 0.016 (0.0039) | 0.4072 |
| Sirloin % Purge | 0.0337 | 0.0148 | 27 | 31 | 6 | 0.031 (0.0043) | 0.029 (0.0039) a | 0.046 (0.0116) b | 0.5071 |
| BF % Purge | 0.0313 | 0.0155 | 26 | 30 | 6 | 0.031 (0.0047) a | 0.026 (0.0044) b | 0.035 (0.0128) | 0.4910 |
| Day 1 WBS | 3.143 | | 27 | 31 | 6 | 2.940 (0.22) a | 3.172 (0.20) b | 3.29 (0.59) | 0.5329 |
| Day 3 WBS | 3.585 | | 27 | 31 | 6 | 3.079 (0.22) a, e | 3.426 (0.20) b, c | 4.847 (0.59) f, d | 0.0315 |
| Day 7 WBS | 3.586 | | 27 | 31 | 6 | 3.301 (0.22) a | 3.407 (0.20) a | 4.279 (0.60) b | 0.3953 |

LSmeans significance levels:
a-b p < .3
c-d p < .1
e-f p < .05
g-h p < .01
i-j p < .005
k-l p < .001
m-n p < .0005
o-p p < .0001

Associations were detected between CAST-PvuII polymorphism and sirloin % purge (P=0.0121) and WBS force at day 5 (P=0.025) (Table 5). Because there were only 2 animals with the 22 genotype, we concentrated on the differences between 11 and 12 genotypes. For WBS force at day 5 (overall P value=0.0045) we detected a significant difference between 11 and 12 genotypes (p<0.01).

TABLE 5

Association analysis of CAST PvuII marker with meat quality, body composition and growth traits in a Duroc x Yorkshire cross

| Trait | Mean | $\sigma_p$ | No. animals 11 | 12 | 22 | Lsmeans (s.e.) 11 | 12 | 22 | Geno P |
|---|---|---|---|---|---|---|---|---|---|
| Live | 250.09 | 9.72 | 40 | 22 | 2 | 254.46 (3.78) a | 253.96 (3.36) a | 233.68 (14.68) b | 0.4522 |
| Hot | 193.49 | 7.67 | 40 | 22 | 2 | 197.11 (2.83) a | 197.06 (2.52) c | 176.93 (10.99) b, d | 0.2515 |
| Dressing(%) | 0.774 | 0.015 | 40 | 22 | 2 | 0.7748 (0.0054) | 0.7758 (0.0048) | 0.7588 (0.0211) | 0.7445 |
| Loin Temp 45 min | 35.831 | 1.38 | 40 | 22 | 2 | 35.484 (0.416) a | 36.021 (0.370) b | 36.286 (1.615) | 0.5729 |
| Loin pH 45 min | 6.244 | 0.22 | 40 | 22 | 2 | 6.246 (0.088) | 6.291 (0.078) | 6.330 (0.342) | 0.9139 |
| Ham Temp 45 min | 36.29 | 1.34 | 40 | 22 | 2 | 35.78 (0.41) a | 36.57 (0.37) b | 36.52 (1.61) | 0.2990 |
| Ham pH 45 min | 6.26 | 0.31 | 40 | 22 | 2 | 6.31 (0.12) | 6.29 (0.10) | 6.35 (0.45) | 0.9864 |
| Loin temp 2 hr | 26.669 | 1.85 | 40 | 22 | 2 | 25.847 (0.648) c | 27.176 (0.577) d | 25.960 (2.517) | 0.2169 |
| Loin pH 2 hr | 5.88 | 0.32 | 40 | 22 | 2 | 5.86 (0.12) | 5.91 (0.11) | 6.02 (0.47) | 0.9352 |
| Ham Temp 2 hr | 28.08 | 3.03 | 40 | 22 | 2 | 28.75 (0.93) | 27.77 (0.83) | 27.86 (3.60) | 0.6886 |
| Ham pH 2 hr | 5.87 | 0.31 | 40 | 22 | 2 | 5.92 (0.12) | 5.85 (0.11) | 6.18 (0.47) | 0.7090 |
| Loin Temp 4 hr | 15.400 | 2.11 | 40 | 22 | 2 | 15.537 (0.599) | 15.299 (0.533) | 13.518 (2.328) | 0.7535 |
| Loin ph 4 hr | 5.76 | 0.27 | 40 | 22 | 2 | 5.77 (0.11) | 5.77 (0.097) | 5.93 (0.425) | 0.9375 |
| Ham temp 4 hr | 21.52 | 2.12 | 37 | 18 | 2 | 21.63 (0.52) | 21.16 (0.46) | 20.04 (1.92) | 0.7013 |
| Ham pH 4 hr | 5.65 | 0.21 | 40 | 22 | 2 | 5.67 (0.07) | 5.60 (0.06) | 5.88 (0.27) | 0.3920 |
| Loin Temp 6 hr | 10.682 | 2.70 | 40 | 22 | 2 | 10.977 (0.525) | 10.559 (0.467) | 9.880 (2.039) | 0.7830 |
| Loin pH 6 hr | 5.69 | 0.20 | 40 | 22 | 2 | 567 (0.08) | 5.70 (0.07) | 5.74 (0.31) | 0.9453 |
| Ham pH 6 hr | 5.56 | 0.13 | 40 | 22 | 2 | 5.55 (0.04) | 5.53 (0.04) | 5.57 (0.16) | 0.8614 |
| Loin pH 24 hr | 5.56 | 0.08 | 40 | 22 | 2 | 5.61 (0.03) a | 5.57 (0.03) b, a | 5.42 (0.11) b | 0.2774 |
| Loin Temp 24 hr | 2.095 | 0.52 | 40 | 22 | 2 | 1.944 (0.113) | 2.061 (0.100) | 2.387 (0.438) | 0.5798 |
| Temp BF 24 hr | 2.948 | 0.49 | 40 | 22 | 2 | 2.90 (0.13) | 3.05 (0.12) | 3.05 (0.51) | 0.6404 |
| pH BF 24 hr | 5.62 | 0.13 | 40 | 22 | 2 | 5.66 (0.04) a | 5.62 (0.04) a | 5.40 (0.17) b | 0.4029 |
| Temp SM 24 hr | 2.811 | 0.53 | 40 | 22 | 2 | 2.64 (0.14) a | 2.88 (0.13) b | 3.26 (0.55) | 0.3434 |
| pH SM 24 hr | 5.60 | 0.13 | 40 | 22 | 2 | 5.62 (0.05) | 5.58 (0.04) | 5.48 (0.18) | 0.6812 |
| Last rib fat | 0.914 | 0.15 | 40 | 22 | 2 | 0.904 (0.042) | 0.937 (0.038) | 0.995 (0.165) | 0.7831 |
| NPPC Color | 2.55 | 0.60 | 40 | 22 | 2 | 2.55 (0.22) | 2.69 (0.20) | 2.48 (0.86) | 0.8471 |
| Firmness | 1.875 | 0.42 | 40 | 22 | 2 | 1.873 (0.146) | 1.938 (0.130) | 1.857 (0.567) | 0.9240 |
| Wetness | 1.945 | 0.50 | 40 | 22 | 2 | 1.833 (0.182) | 2.022 (0.162) | 2.325 (0.708) | 0.6643 |
| Marbling | 1.633 | 0.58 | 40 | 22 | 2 | 1.56 (0.18) | 1.72 (0.16) | 2.11 (0.69) | 0.6936 |
| JCS | 2.383 | 0.58 | 40 | 22 | 2 | 2.337 (0.200) | 2.489 (0.178) | 1.753 (0.777) | 0.5415 |
| LD L | 49.69 | 3.31 | 40 | 22 | 2 | 49.65 (1.24) | 48.83 (1.10) | 52.61 (4.81) | 0.6459 |
| Ld a | 4.12 | 1.14 | 40 | 22 | 2 | 4.33 (0.38) | 4.20 (0.34) | 4.35 (1.49) | 0.9526 |
| LD b | 10.62 | 1.08 | 40 | 22 | 2 | 10.65 (0.36) | 10.38 (0.32) | 11.88 (1.40) | 0.4931 |
| LD L* | 56.59 | 3.19 | 40 | 22 | 2 | 56.53 (1.19) | 55.75 (1.06) | 59.55 (4.63) | 0.6336 |
| Ld a* | 3.17 | 1.23 | 40 | 22 | 2 | 3.41 (0.41) | 3.29 (0.36) | 3.25 (1.57) | 0.9720 |
| LD b* | 15.53 | 1.37 | 40 | 22 | 2 | 15.56 (0.42) | 15.26 (0.37) a | 17.22 (1.62) b | 0.4343 |
| SM L | 44.92 | 2.64 | 40 | 22 | 2 | 44.19 (0.95) | 44.90 (0.85) | 47.63 (3.70) | 0.6821 |
| SM a | 6.73 | 1.27 | 40 | 22 | 2 | 6.57 (0.41) | 6.81 (0.37) | 6.95 (1.61) | 0.8942 |
| SM b | 10.44 | 0.99 | 40 | 22 | 2 | 10.10 (0.33) | 10.40 (0.29) | 11.64 (1.29) | 0.5488 |
| SM L* | 51.83 | 2.67 | 40 | 22 | 2 | 51.07 (0.96) | 51.80 (0.86) | 54.68 (3.74) | 0.6642 |
| SM a* | 6.46 | 1.47 | 40 | 22 | 2 | 6.36 (0.48) | 6.55 (0.42) | 6.36 (1.85) | 0.9396 |
| SM b* | 15.90 | 1.43 | 40 | 22 | 2 | 15.42 (0.45) a | 15.82 (0.40) | 17.63 (1.73) b | 0.5111 |
| BF L | 45.87 | 3.70 | 40 | 22 | 2 | 44.56 (1.39) | 44.38 (1.24) a | 50.60 (5.40) b | 0.5625 |
| BF a | 7.83 | 1.29 | 40 | 22 | 2 | 8.19 (0.40) | 8.18 (0.36) | 7.35 (1.55) | 0.8861 |
| BF b | 10.93 | 1.24 | 40 | 22 | 2 | 10.65 (0.44) | 10.62 (0.39) | 11.66 (1.71) | 0.8516 |
| BF L* | 52.79 | 3.69 | 40 | 22 | 2 | 51.45 (1.37) | 51.26 (1.22) a | 57.50 (5.34) b | 0.5536 |
| BF a* | 7.61 | 1.46 | 40 | 22 | 2 | 8.16 (0.43) | 8.13 (0.38) | 6.73 (1.68) | 0.7469 |
| BF b* | 16.57 | 1.65 | 40 | 22 | 2 | 16.27 (0.55) | 16.24 (0.49) | 17.22 (2.14) | 0.9111 |
| Ave Drip Loss Day 1 | 0.0212 | 0.0114 | 40 | 22 | 2 | 0.0219 (0.0045) | 0.0217 (0.0040) | 0.0197 (0.0174) | 0.9939 |
| Drip Loss Day 1-5 | 0.0194 | 0.0067 | 40 | 22 | 2 | 0.0191 (0.0015) | 0.0189 (0.0014) | 0.0173 (0.0059) | 0.9665 |
| Ave Drip Loss | 0.0402 | 0.0149 | 40 | 22 | 2 | 0.0405 (0.0052) | 0.0402 (0.0046) | 0.0365 (0.0201) | 0.9849 |
| SM % Purge | 0.0344 | 0.0126 | 40 | 22 | 2 | 0.0340 (0.0041) | 0.0328 (0.0037) | 0.0490 (0.0160) | 0.6198 |
| BF % Purge | 0.0313 | 0.0155 | 38 | 22 | 2 | 0.0327 (0.0049) | 0.0311 (0.0043) | 0.0105 (0.0189) | 0.5984 |
| Ave % Purge | 0.0331 | 0.0104 | 40 | 22 | 2 | 0.0304 (0.0030) a | 0.0309 (0.0027) a | 0.0478 (0.0117) b | 0.4199 |
| Day 3 WBS | 3.585 | | 40 | 22 | 2 | 3.465 (0.236) a | 3.860 (0.210) b | 2.917 (0.917) | 0.2339 |

TABLE 5-continued

Association analysis of CAST PvuII marker with meat quality, body composition and growth traits in a Duroc x Yorkshire cross

| Trait | Mean | $\sigma_p$ | No. animals 11 | 12 | 22 | Lsmeans (s.e.) 11 | 12 | 22 | Geno P |
|---|---|---|---|---|---|---|---|---|---|
| Day 5 WBS | 3.524 | | 40 | 22 | 2 | 3.083 (0.208) g | 3.802 (0.185) h | 3.883 (0.807) | 0.0250 |
| Day 7 WBS | 3.586 | | 40 | 22 | 2 | 3.711 (0.227) a | 3.385 (0.202) b | 3.375 (0.881) | 0.5032 |

LSmeans significance levels:
a-b p < .3
c-d p < .1
e-f p < .05
g-h p < .01
i-j p < .005
k-l p < .001
m-n p < .0005
o-p p < .0001 d) We used several PIC commercial populations for an association study in order to verify some of the significant results we obtained using the F2 generation of the B×Y family. The samples we used have data for meat quality, body composition and growth traits. For these samples we did not have Instron force data, but we had firmness (a subjective score) and also drip percentage. We again used only CAST-Hpy188I and PvuII markers. CAST AciI was not sufficiently polymorphic for an association study (see Table 6).

TABLE 6

Genotype and allelic frequency for the porcine CAST-Hpy188I, PvuII and AciI polymorphisms in several PIC commercial lines.

| | Landrace | Large White | Berkshire | Duroc | Duroc Synthetic | Hampshire | Pietrain | Composite |
|---|---|---|---|---|---|---|---|---|
| CastHpy188I | | | | | | | | |
| 11 | 5 | 4 | 21 | 12 | 6 | 11 | 16 | 6 |
| 12 | 14 | 9 | 2 | 12 | 16 | 8 | 8 | 15 |
| 22 | 5 | 10 | | | 2 | 5 | | 3 |
| N | 24 | 23 | 23 | 24 | 24 | 24 | 24 | 24 |
| P | 0.5 | 0.37 | 0.95 | 0.75 | 0.58 | 0.63 | 0.83 | 0.56 |
| Cast-PvuII | | | | | | | | |
| 11 | 21 | 7 | 19 | 21 | 9 | 11 | 24 | 19 |
| 12 | | 10 | 2 | 3 | 14 | 7 | | 5 |
| 22 | | 5 | | | 1 | 5 | | |
| N | 21 | 22 | 21 | 24 | 24 | 23 | 24 | 24 |
| P | 1 | 0.55 | 0.95 | 0.94 | 0.67 | 0.63 | 1 | 0.9 |
| Cast-AciI | | | | | | | | |
| 11 | 21 | 24 | 22 | 22 | 24 | 22 | 22 | 24 |
| 12 | 3 | | 1 | | | 1 | 2 | |
| 22 | | | | | | | | |
| N | 24 | 24 | 23 | 22 | 24 | 23 | 24 | 24 |
| P | 0.94 | 1 | 0.98 | 1 | 1 | 0.98 | 0.96 | 1 | p - frequency of allele 1

In the Large White based line we saw some significant associations (Table 7 and 8). For both markers, firmness has the same trend as in the B×Y population. The 11 (KK) CAST Hpy188I genotype is associated with higher drip percentage. In the same direction are also the effects of CAST-PvuII genotypes. Regarding the other traits we can see that 22 genotype (for both of the markers) is associated with slower growth rate and is leaner than 11. There are significant differences between the genotype on test daily gain (TDG) and US-muscle depth (US_MD) for both of the markers.

TABLE 7

Association results between the genotypes of CAST Hpy188I and some meat quality and growth traits in PIC Large White based population.

| | Least Square Means * | | | |
|---|---|---|---|---|
| Traits | 11(KK) | 12(KR) | 22 (RR) | P |
| Firmness | 2.74 (29)[a] 29 | 2.88 (60) 60 | 2.98 (26)[b] 26 | 0.36 |
| Hprofat | 14.28 (81)[a] 81 | 13.89 (176)[b] 176 | 13.87 (82) 82 | 0.48 |
| LDG, g/d | 648.7 (90)[a] 90 | 649.5 (193)[a] 193 | 643.0 (101)[b] 101 | 0.32 |
| TDG, g/d | 846.1 (86)[c] 86 | 846.7 (189)[e] 189 | 830.0 (101)[d,f] 101 | 0.09 |
| US_MD | 57.90 (85)[e] 85 | 58.50 (185)[e] 185 | 60.33 (98)[f] 98 | 0.03 |

* Significant differences:
[a-b] p < .3;
[c-d] p < .1;
[e-f] p < .05

TABLE 8

Association results between the genotypes of CAST PvuII and some meat quality and growth traits in PIC Large White based population

| | Least Square Means* | | | |
|---|---|---|---|---|
| Traits | 11(RR) | 12(RS) | 22 (SS) | P |
| Firmness | 2.80 (44) 44 | 2.87 (53) 53 | 2.97 (10) 10 | 0.69 |
| Hprofat | 13.96 (111) 111 | 14.06 (164) 164 | 13.38 (41) 41 | 0.28 |
| LDG, g/d | 649.2 (123)[a] 123 | 648.5 (185)[c] 185 | 637.9 (50)[d] 50 | 0.13 |
| TDG, g/d | 846.1 (118)[e] 118 | 846.7 (182)[c] 182 | 830.0 (50)[f,d] 50 | 0.06 |
| US_MD | 57.69 (116)[e,a] 116 | 59.56 (176)[f] 176 | 59.44 (50)[b] 50 | 0.05 |

*Significant differences:
[a-b] p < .3;
[c-d] p < .1;
[e-f] p < .05

In a joint analysis including both markers with and without interaction between them, some associations are suggested. There are interactions detected only for boneless weight of the loin (P=0.03), loinpH (0.04) and hampH (0.02) but the number of individuals in four of the classes is very low making it difficult to draw any conclusions. Including both genotypes in the model, the overall probability was <0.10 for US_MD for Hpy188I, and for loinminb, LMprct, US_MD for PvuII respectively.

In the Duroc Synthetic line we saw some significant associations (Tables 9 and 10). For both markers, the most important association was for drip percentage: P=0.004 for PvuII and P=0.03 for Hpy188I. The difference between LS means of homozygous classes was 1.56% for PvuII and 0.74% for Hpy188I.

In the Composite line for the CAST-Hpy188 I an important association was detected for firmness (Table 11). The 11 genotype is associated with lower firmness, as for Large White population (both markers), and for B×Y (CAST-Hpy188I) and the F1 generation Duroc×Yorkshire for CAST-Hpy188I.

For the CAST-PvuII an interesting association was found for h_binwt (bone in weight of the ham), the 11 genotype being associated with the higher value (Table 12). Also an association was detected for hpromeat (Henessey probe loin depth), with the 11 genotype having the highest value. This association was also confirmation by haplotype analysis in same line (contrast P is 0.06 between haplotype 2 and 3, difference between them is due to PvuII site).

Across the lines we detected for CAST Hpy188I some associations for firmness (0.07) (11 genotype—lower firmness like in B×YF2 population), hamminl (P=0.05), hprorib (P=0.14), endwt (P=0.02), LDG (P=0.06), TDG (0.04) and for US_MD (P=0.05).

For the last four traits the same associations were observed and they were in the same direction as was obtained for Large White population (Table 13).

For the CAST-PvuII some associations were observed for loinminb (0.001), for hammina (P=0.01), endwt (P=0.03), LDG (P=0.13) and for TDG (0.12). For the last three traits the same associations were observed and were in the same direction as was obtained for Large White population and also across lines analysis for CAST Hpy188I (Table 14)

TABLE 9

Analysis of meat quality and production traits with CAST Hpy-188I in PIC Duroc Synthetic based line.

| | Mean | | No. animals | | | Lsmeans (s.e.) | | | geno | α | | δ | |
|---|---|---|---|---|---|---|---|---|---|---|---|---|---|
| Trait | (s.e.) | $\sigma_p$ | 11 | 12 | 22 | 11 | 12 | 22 | p | trait (s.e.) | p | trait (s.e.) | p |
| Marbling | 2.50 (0.05) | 0.71 | 75 | 104 | 23 | 2.47 (0.09) a | 2.62 (0.07) b e | 2.26 (0.14) b f | 0.04 | −0.10 (0.08) | a | 0.17 (0.07) | c |
| LoinpH | 5.73 (0.01) | 0.14 | 106 | 176 | 55 | 5.74 (0.01) e | 5.73 (0.01) c | 5.69 (0.02) f d | 0.11 | −0.02 (0.01) | c | 0.01 (0.01) | |

TABLE 9-continued

Analysis of meat quality and production traits with CAST Hpy-188I in PIC Duroc Synthetic based line.

| Trait | Mean (s.e.) | $\sigma_p$ | No. animals 11 | 12 | 22 | Lsmeans (s.e.) 11 | 12 | 22 | geno p | $\alpha$ trait (s.e.) | p | $\delta$ trait (s.e.) | p |
|---|---|---|---|---|---|---|---|---|---|---|---|---|---|
| Hamminl | 47.98 (0.30) | 4.34 | 75 | 105 | 25 | 48.60 (0.59) a c | 47.62 (0.53) b | 46.84 (0.89) d | 0.15 | −0.88 (0.50) | b | −0.07 (0.39) | |

TABLE 10

Analysis of meat quality and production traits with CAST PvuII in PIC Duroc Synthetic based line.

| Trait | Mean (s.e.) | $\sigma_p$ | No. animals 11 | 12 | 22 | Lsmeans (s.e.) 11 | 12 | 22 | geno p | $\alpha$ trait (s.e.) | p | $\delta$ trait (s.e.) | p |
|---|---|---|---|---|---|---|---|---|---|---|---|---|---|
| L_binwt | 20.64 (0.15) | 2.12 | 113 | 64 | 8 | 20.80 (0.14) e | 20.20 (0.18) f a | 21.08 (0.51) b | 0.02 | 0.14 (0.27) | | −0.49 (0.21) | c |
| Drippret | 2.25 (0.10) | 1.37 | 103 | 51 | 7 | 2.10 (0.12) a i | 2.44 (0.17) b e | 3.66 (0.45) j f | 0.004 | 0.78 (0.24) | e | −0.29 (0.19) | a |

TABLE 11

Analysis of meat quality and production traits with CAST Hpy-188I in PIC Composite line.

| Trait | Mean (s.e.) | $\sigma_p$ | No. animals 11 | 12 | 22 | Lsmeans (s.e.) 11 | 12 | 22 | geno p | $\alpha$ trait (s.e.) | p | $\delta$ trait (s.e.) | p |
|---|---|---|---|---|---|---|---|---|---|---|---|---|---|
| Firmness | 2.71 (0.11) | 0.94 | 26 | 28 | 14 | 2.57 (0.13) c i | 2.87 (0.11) d | 3.29 (0.17) j c | 0.005 | 0.36 (0.11) | e | −0.04 (0.11) | |
| Endwt | 113.3 (0.47) | 7.88 | 82 | 145 | 40 | 111.8 (1.02) e | 111.6 (0.80) e | 108.6 (1.38) f | 0.10 | −1.63 (0.80) | c | 0.89 (0.69) | a |

TABLE 12

Analysis of meat quality and production traits with CAST PvuII in PIC Composite line.

| Trait | Mean (s.e.) | $\sigma_p$ | No. animals 11 | 12 | 22 | Lsmeans (s.e.) 11 | 12 | 22 | geno p | $\alpha$ trait (s.e.) | p | $\delta$ trait (s.e.) | p |
|---|---|---|---|---|---|---|---|---|---|---|---|---|---|
| h_binwt | 25.43 (0.18) | 1.98 | 76 | 23 | 1 | 25.56 (0.22) e a | 24.80 (0.34) f | 23.61 (1.39) b | 0.05 | −0.97 (0.69) | a | 0.15 (0.49) | |
| Hpromeat | 63.19 (0.64) | 9.74 | 149 | 49 | 4 | 60.97 (0.89) e | 58.16 (1.35) f | 58.89 (4.10) | 0.13 | −1.04 (2.05) | | −1.18 (1.54) | |

TABLE 13

Analysis of meat quality and production traits with CAST Hpy-188I Across All lines

| Trait | Mean (s.e.) | $\sigma_p$ | No. animals 11 | 12 | 22 | LSmeans (s.e.) 11 | 12 | 22 |
|---|---|---|---|---|---|---|---|---|
| Marbling | 2.18 (0.03) | 0.78 | 179 | 310 | 104 | 2.23 (0.05) | 2.28 (0.04) a | 2.20 (0.07) b |
| Firmness | 2.86 (0.06) | 1.06 | 118 | 163 | 58 | 2.95 (0.06) c e | 3.10 (0.05) d | 3.17 (0.09) f |
| Hamminl | 46.89 (0.20) | 4.52 | 156 | 253 | 86 | 47.62 (0.39) e | 47.24 (0.33) e | 46.19 (0.49) f |
| Hprorib | 14.59 (0.21) | 4.07 | 130 | 182 | 61 | 15.22 (0.42) c a | 14.30 (0.37) d | 14.30 (0.56) b |
| Endwt | 111.6 (0.24) | 7.62 | 285 | 518 | 201 | 111.4 (0.46) g | 110.9 (0.37) e | 109.6 (0.54) h f |
| LDG, g/d | 664.5 (1.55) | 49.7 | 285 | 518 | 201 | 665.6 (2.91) e | 663.3 (2.26) c | 656.8 (3.16) f d |
| TDG, g/d | 862.1 (2.53) | 75.4 | 225 | 450 | 185 | 870.7 (5.11) e | 867.8 (3.94) e | 854.3 (5.56) f |
| US_MD | 61.52 (0.27) | 8.09 | 226 | 449 | 183 | 59.48 (0.56) e | 59.71 (0.46) e | 60.95 (0.60) f |

| Trait | geno p | Line*geno p | $\alpha$ trait (s.e.) | 1 | 2 | $\delta$ trait (s.e.) | 1 | 2 |
|---|---|---|---|---|---|---|---|---|
| Marbling | 0.40 | 0.009 | −0.02 (0.04) | | c | 0.05 (0.03) | a | c |
| Firmness | 0.07 | 0.02 | 0.11 (0.05) | c | e | 0.03 (0.05) | | |
| Hamminl | 0.05 | 0.69 | −0.71 (0.29) | c | | 0.22 (0.24) | | |
| Hprorib | 0.14 | 0.80 | −0.46 (0.33) | a | | −0.31 (0.29) | a | |

TABLE 13-continued

Analysis of meat quality and production traits with CAST Hpy-188I Across All lines

| | | | | | | | |
|---|---|---|---|---|---|---|---|
| Endwt | 0.02 | 0.38 | −0.91 (0.33) | d | | 0.30 (0.29) | a |
| LDG, g/d | 0.06 | 0.89 | −4.37 (1.93) | c | | 1.42 (1.72) | |
| TDG, g/d | 0.04 | 0.75 | −8.17 (3.44) | c | | 3.54 (3.07) | a |
| US_MD | 0.05 | 0.39 | 0.74 (0.33) | c | a | −0.33 (0.28) | a |

TABLE 14

Analysis of meat quality and production traits with CAST PvuII Across All lines

| | | | No. animals | | | LSmeans (s.e.) | | |
|---|---|---|---|---|---|---|---|---|
| Trait | Mean (s.e.) | σ$_p$ | 11 | 12 | 22 | 11 | 12 | 22 |
| Loinminb | 3.17 (0.04) | 1.23 | 480 | 337 | 71 | 3.35 (0.05) e a | 3.52 (0.06) f i | 3.16 (0.11) b j |
| Hamminl | 46.89 (0.20) | 4.52 | 254 | 167 | 31 | 47.25 (0.33) a | 47.23 (0.39) a | 46.05 (0.80) b |
| Hammina | 8.59 (0.08) | 1.8 | 254 | 166 | 31 | 8.60 (0.12) e a | 8.97 (0.14) f | 8.27 (0.29) b e |
| Endwt | 111.6 (0.24) | 7.62 | 506 | 351 | 77 | 111.2 (0.39) c e | 110.3 (0.46) d a | 109.0 (0.86) f b |
| LDG, g/d | 664.5 (1.55) | 49.7 | 506 | 351 | 77 | 663.1 (2.43) c | 662.9 (2.70) c | 653.4 (4.81) d |
| TDG, g/d | 862.1 (2.53) | 75.4 | 422 | 313 | 73 | 869.2 (4.20) e | 865.5 (4.70) c | 850.8 (8.50) f d |

| | | | α | | | δ | | |
|---|---|---|---|---|---|---|---|---|
| | geno | Line*geno | | p | | | p | |
| Trait | p | p | trait (s.e.) | 1 | 2 | trait (s.e.) | 1 | 2 |
| Loinminb | 0.001 | 0.38 | −0.09 (0.06) | a | a | 0.18 (0.05) | g | |
| Hamminl | 0.32 | 0.76 | −0.60 (0.41) | a | | 0.39 (0.34) | a | |
| Hammina | 0.01 | 0.40 | −0.16 (0.15) | a | | 0.36 (0.12) | e | |
| Endwt | 0.03 | 0.65 | −1.08 (0.45) | c | | 0.11 (0.38) | | |
| LDG, g/d | 0.13 | 0.47 | −4.82 (2.53) | b | | 3.08 (2.13) | a | |
| TDG, g/d | 0.12 | 0.77 | −9.18 (4.49) | c | | 3.66 (3.81) | | |

Haplotype analysis for each population revealed several interesting associations. This analysis allows us to estimate the impact of the different polymorphisms. In order to do this we are interested in the differences between effects of haplotypes that are different at only one polymorphic site so as to detect each site effect. For example in the Duroc Synthetic and Composite Line where we have three haplotypes the unique difference between haplotype 2 (2-1) and 3 (2-2) is at the PvuII site. In this way it is possible to estimate the potential effect of the PvuII polymorphism. In summary based on haplotype analysis we revealed the following effects (taking in account contrast P values lower than 0.10):

CAST Hpy188I has effects (or is in linkage disequilibrium with QTL) on: loinminl (Large White), loinpH (Large White), days on test (Large White), hamminl (Large White, all lines), boneless weight of the loin (Duroc), firmness (Composite), LDG (Composite, all lines), TDG (all lines).

CAST-PvuII has effects (or is in linkage disequilibrium with QTL) on: loinminl (Large White, Duroc and all lines), loin pH (Large White), hpromeat (Large White, all lines), aloca backfat (Large White), days on test (Large White), drip percentage (Duroc), US_MD (Composite) and bone in weight of the ham (Composite).

Both CAST Hpy188I and PvuII have an effect (or are in linkage disequilibrium with a QTL) on % drip loss. We also ran an analysis including both the Duroc and Composite line because there are just 3 haplotypes present in both lines in order to attempt a better estimate of the effects. We obtained a highly significant difference for % drip loss (larger as in Duroc) (Table 17) between the effects of haplotype 1 and 3. Haplotype 3 is associated with higher drip loss as expected based on the other analyses. Also significant differences between haplotype 2 and 3 were revealed, again similar to the Duroc population, suggesting an effect of PvuII alone. When allele 2 is present for both sites (haplotype 3) the change in % drip loss is significant. When we compared the haplotype results with single association study we obtained the same direction in the phenotype variation. For example in the case of firmness, allele CAST-Hpy188I-1 is associated with lower firmness compared with the 2 allele. The same result was revealed by haplotype analysis. The same situation applies for another trait—drip percentage with a strong association that was revealed in Duroc population for CAST-PvuII polymorphism. (as indicated we only consider here the effects based on the differences between the haplotypes and only the differences where P<0.10 taken in account).

TABLE 15

Association results between the genotypes of CAST PvuII and some meat quality traits in F$_2$ Berkshire x Yorkshire family

| TRAITS | 11(RR) | 12(RS) | 22(SS) | P |
|---|---|---|---|---|
| Leanness | 35.37 [a] | 36.10 [b] | 35.92 | 0.232 |
| Firmness | 3.33 | 3.42 | 3.41 | 0.301 |
| 24 h loin pH | 5.73 [a,c] | 5.76 [b] | 5.78 [d] | 0.087 |
| Juiceness | 6.19 [c] | 6.03 | 5.76 [d] | 0.093 |
| Tenderness | 7.98 [a] | 7.76 [b] | 7.76 | 0.151 |
| Chew score | 2.37 | 2.51 | 2.53 | 0.238 |
| InstronForce | 4.39 [a] | 4.49 | 4.62 [b] | 0.105 |
| WHC | 0.203 | 0.199 | 0.178 | 0.277 |

Significant differences:
[a-b] p < .1;
[c-d] p < .05;
[e-f] p < .005,
[g-h] p < .0005.
n = 168 (11), 209-216(12) and 98-104 (22).

TABLE 16

CAST haplotype substitution effects for some meat quality traits in B x Y

| Trait | Haplotype* effect | | | Contrast p value | | |
|---|---|---|---|---|---|---|
| | 1 | 2 | 3 | 1 vs 2 | 1 vs 3 | 2 vs 3 |
| Juiciness | 0.22 | 0.06 | 0 | 0.43 | 0.01 | 0.75 |
| Tenderness | 0.14 | 0.10 | 0 | 0.82 | 0.07 | 0.55 |
| Chew score | −0.12 | −0.02 | 0 | 0.43 | 0.03 | 0.87 |
| InstronForce (kg) | −0.14 | −0.21 | 0 | 0.54 | 0.008 | 0.07 |
| Firmness | −0.06 | 0.18 | 0 | 0.01 | 0.10 | 0.04 |

| | frequency |
|---|---|
| *haplotype 1: Hpy188I -1 and PvuII - 1 | 0.50 |
| haplotype 2: Hpy188I -2 and PvuII - 1 | 0.07 |
| haplotype 3: Hpy188I -2 and PvuII - 2 | 0.43 | n = 448-482

TABLE 17

CAST haplotype substitution effects for % drip loss in two PIC populations

| Line | n | Haplotype* freq. | | | Haplotype effect | | | Contrast p value | | |
|---|---|---|---|---|---|---|---|---|---|---|
| | | 1 | 2 | 3 | 1 | 2 | 3 | 1 vs 2 | 1 vs 3 | 2 vs 3 |
| DS | 154 | 0.61 | 0.19 | 0.20 | −0.55 | −0.46 | 0 | 0.66 | 0.004 | 0.04 |
| C | 93 | 0.62 | 0.28 | 0.10 | −0.47 | −0.24 | 0 | 0.28 | 0.17 | 0.51 |
| DS + C | 297 | 0.61 | 0.22 | 0.17 | −0.58 | −0.40 | 0 | 0.23 | 0.0004 | 0.03 |

*haplotype 1: Hpy188I -1 and PvuII - 1.
haplotype 2: Hpy188I -2 and PvuII - 1.
haplotype 3: Hpy188I -2 and PvuII - 2.

EXAMPLE 4

In order to demonstrate further the effect of the markers discovered in the Calpastatin gene on meat quality and growth traits, we tested their effects in additional populations of pigs:

1. Meat Quality Data Set A.

Phenotypic data (meat quality, body composition and growth traits) were collected on three commercial populations or lines. Statistical analysis was undertaken to determine associations between CAST genotype and variation in the phenotypic traits.

The associations between the CAST polymorphisms and the traits considered were tested using mixed model procedures (SAS® procedure MIXED, SAS Institute Inc., Cary, N.C.) with a model which always included sire as a random effect and slaughter date and marker genotype(s) as fixed effects. Line was added as a fixed effect for across line analyses. Sex and farm were not included because all traits were measured on females only and no more than one farm was represented on each slaughter date. While males were not used in this portion of the analysis our results in the B×Y suggest no sex by genotype effect (see example 3).

The number of animals used in association analyses varied based on the trait measured, and are listed in the tables.

Results for relevant meat quality and growth traits are shown in Tables 1 and 2 for a Large White based line for two of the markers (CAST Hpy188I and CAST PvuII).

These samples did not have instron force data, but firmness (a subjective score) and drip percentage were recorded. For both markers, firmness shows the same trend as was observed for the B×Y population (Example 3)—genotype 11 being associated with lower firmness (a lower value is considered preferable). This difference did not reach statistical significance (p=0.36 for CAST Hpy188I) however this is a subjective score which is a less powerful measure. However, the trend is in the expected direction and it is expected to be a significant difference when larger numbers are recorded. The 22 genotype (for both of the markers) is associated with slower growth rate than the 11 and 12 genotypes and there is a trend for animals of this genotype to be leaner.

Results with a Duroc based population are shown in Tables 3 and 4. Significant associations were found for both markers for Henessey probe loin depth (genotype 11 associated with higher least square (LS) mean value); CAST-PvuII and marbling (P=0.010) where genotype 11 has a lower value.

The third population was a synthetic or composite population originally made by crossing several different breeds. Results are shown in Tables 5 and 6. For the CAST-Hpy188I, a highly significant association was detected for firmness (P=0.0051; Table 5).

The 11 genotype is associated with lower firmness, exactly as in the B×Y $F_2$ experiment (see Example 3) or in the other populations in this example. For CAST-PvuII a highly significant association was discovered again for Henessey probe loin depth (genotype 11 has a higher LS value; P=0.006) (Table 6). Drip loss also tends to be lower with genotype 11 for both of the markers. The difference is statistically significant for CAST Hpy188I (P=0.03).

In order to improve the estimate of the marker effects, the data from the all populations were combined and analysed using the same model (this was deemed to be appropriate as there was no evidence of a significant interaction of genotype by population) (Table 7 and 8).

The most significant association for both of the markers was (as expected from the individual results) with firmness. There are also significant differences between the LS means of the genotypes (p<0.05). There is a 0.26 unit difference between the homozygous genotypes for CAST PvuII and 0.13 units for CAST Hpy188I—and again the 11 genotype was associated with lower firmness for both markers (Table 7 and 8).

TABLE 1

Association results between CAST Hpy188I genotype and some meat quality and growth traits in a Large White based population.

| Traits | 11(KK) | 12(KR) | 22 (RR) | P | Least Square Means * | | |
|---|---|---|---|---|---|---|---|
| Firmness | 2.74 (.14) [a] | 2.88 (.11) | 2.98 (.15) [b] | 0.36 | 29 | 60 | 26 |
| Hprofat | 14.28 (.35) [a] | 13.89 (.29) [b] | 13.87 (.37) | 0.48 | 81 | 176 | 82 |
| LDG, g/d | 648.7 (4.42) [a] | 649.5 (3.36) [a] | 643.0 (4.29) [b] | 0.32 | 90 | 193 | 101 |
| TDG, g/d | 846.1 (7.84) [c] | 846.7 (5.94) [e] | 830.0 (7.60) [d,f] | 0.09 | 86 | 189 | 101 |
| US_MD | 57.90 (.77) [e] | 58.50 (.57) [e] | 60.33 (.74) [f] | 0.03 | 85 | 185 | 98 |

* Significant differences:
[a-b] $p < .3$;
[c-d] $p < .1$;
[e-f] $p < .05$

TABLE 2

Association results between CAST PvuII genotype and some meat quality and growth traits in a Large White based population

| | Least Square Means* | | | | | | |
|---|---|---|---|---|---|---|---|
| Traits | 11(RR) | 12(RS) | 22 (SS) | P | | | |
| Firmness | 2.80 (.12) | 2.87 (.12) | 2.97 (.21) | 0.69 | 44 | 53 | 10 |
| Hprofat | 13.96 (.31) [a] | 14.06 (.28) [a] | 13.38 (.45) [b] | 0.28 | 111 | 164 | 41 |
| LDG, g/d | 649.2 (3.93) [c] | 648.5 (3.42) [c] | 637.9 (5.53) [d] | 0.13 | 123 | 185 | 50 |
| TDG, g/d | 849.1 (6.94) [e] | 842.6 (6.03) [c] | 823.2 (9.82) [f,d] | 0.06 | 118 | 182 | 50 |
| US_MD | 57.69 (.69) [e,a] | 59.56 (.58) [f] | 59.44 (.98) [b] | 0.05 | 116 | 176 | 50 |

* Significant differences:
[a-b] $p < .3$;
[c-d] $p < .1$;
[e-f] $p < .05$

TABLE 3

Association results between CAST Hpy188I genotype and some meat quality and growth traits in a Duroc based population.

| Traits | 11(KK) | 12(KR) | 22 (RR) | P | Least Square Means* | | |
|---|---|---|---|---|---|---|---|
| Drippret | 1.81 (.13) [a] | 2.01 (.15) [b] | 1.87 (.30) [b] | 0.43 | 137 | 100 | 17 |
| Hpromeat | 53.15 (.82) [c,k] | 51.22 (.92) [d,e] | 46.38 (1.92) [l,f] | 0.002 | 129 | 95 | 17 |
| aloca backfat | 12.47 (.28) [e] | 12.77 (.31) [c] | 13.92 (.64) [f,d] | 0.09 | 136 | 99 | 17 |

*Significant differences:
[a-b] $p < .3$;
[c-d] $p < .1$;
[e-f] $p < .05$;
[k-l] $p < .001$

TABLE 4

Association results between CAST PvuII genotype and some meat quality and growth traits in a Duroc based population

| | Least Square Means* | | | | | | |
|---|---|---|---|---|---|---|---|
| Traits | 11(RR) | 12(RS) | 22 (SS) | P | | | |
| Firmness | 3.21 (.05) [a] | 3.27 (.09) | 3.60 (.33) [b] | 0.45 | 152 | 54 | 3 |
| Drippret | 1.84 (.12) [a] | 2.03 (.17) [b] | 1.83 (.48) | 0.50 | 175 | 76 | 6 |
| Hpromeat | 52.94 (.75) [i,a] | 49.43 (1.10) [j] | 48.04 (3.08) [b] | 0.0045 | 166 | 72 | 6 |
| Marbling | 2.76 (.08) [e,c] | 2.56 (0.11) [f] | 3.29 (0.28) [d,e] | 0.01 | 175 | 76 | 6 |

*Significant differences:
[a-b] $p < .3$;
[c-d] $p < .1$;
[e-f] $p < .05$;
[i-j] $p < .005$

TABLE 5

Association results between CAST Hpy188I genotype and some meat quality and growth traits in a Composite population.

| Traits | 11(KK) | 12(KR) | 22 (RR) | P | Least Square Means * | | |
|---|---|---|---|---|---|---|---|
| Firmness | 2.89 (.13)$^{e,i}$ | 3.19 (.10)$^{f,c}$ | 3.50 (.14)$^{j,d}$ | 0.0051 | 33 | 44 | 21 |
| Dripprct | 2.06 (.26)$^{a}$ | 2.41 (.22)$^{b}$ | 2.46 (.28)$^{b}$ | 0.33 | 47 | 64 | 27 |

* Significant differences:
$^{a-b}$ p < .3;
$^{c-d}$ p < .1;
$^{e-f}$ p < .05;
$^{i-j}$ p < .005

TABLE 6

Association results between CAST PvuII genotype and some meat quality and growth traits in a Composite population

| | Least Square Means* | | | | | | |
|---|---|---|---|---|---|---|---|
| Traits | 11(RR) | 12(RS) | 22 (SS) | P | Least Square Means* | | |
| Firmness | 3.17 (.11) | 3.21 (.13) | 3.40 (.34) | 0.81 | 67 | 28 | 3 |
| Dripprct | 2.11 (.20)$^{g}$ | 2.84 (.26)$^{h}$ | 2.41 (.72) | 0.03 | 103 | 34 | 3 |
| Hpromeat | 62.57 (.87)$^{e,g}$ | 59.80 (1.19)$^{f,c}$ | 53.65 (3.35)$^{h,d}$ | 0.006 | 175 | 64 | 6 |
| LMprct | 47.26 (.23)$^{a,i}$ | 46.81 (.29)$^{b,e}$ | 45.05 (.74)$^{j,f}$ | 0.014 | 62 | 27 | 3 |
| Marbling | 2.14 (.08)$^{g}$ | 2.25 (.11)$^{e}$ | 3.21 (.39)$^{h,f}$ | 0.02 | 125 | 46 | 3 |
| US_MD | 63.21 (.7)$^{c,a}$ | 61.63 (.91)$^{d}$ | 59.78 (2.52)$^{b}$ | 0.13 | 215 | 72 | 6 |

*Significant differences:
$^{a-b}$ p < .3;
$^{c-d}$ p < .1;
$^{e-f}$ p < .05;
$^{g-h}$ p < .01;
$^{i-j}$ p < .005.

TABLE 7

Association results between CAST Hpy188I genotype and some meat quality and growth traits across all lines/populations.

| Traits | 11(KK) | 12(KR) | 22 (RR) | P | Least Square Means * | | |
|---|---|---|---|---|---|---|---|
| Firmness | 2.96 (.06)$^{e,c}$ | 3.06 (.05)$^{f}$ | 3.09 (.07) | 0.06 | 319 | 359 | 102 |
| Dripprct | 2.06 (.11) | 2.11 (.10) | 2.14 (.14) | 0.82 | 367 | 421 | 123 |

* Significant differences:
$^{a-b}$ p < .3;
$^{c-d}$ p < .1;
$^{e-f}$ p < .05;

TABLE 8

Association results between CAST PvuII genotype and some meat quality and growth traits across all lines/populations.

| | Least Square Means* | | | | | | |
|---|---|---|---|---|---|---|---|
| Traits | 11(RR) | 12(RS) | 22 (SS) | P | Least Square Means* | | |
| Firmness | 3.03 (.05)$^{e}$ | 3.04 (.05)$^{e}$ | 3.29 (.11)$^{f}$ | 0.06 | 495 | 249 | 30 |
| Dripprct | 2.07 (.1)$^{a}$ | 2.21 (.11)$^{b}$ | 2.04 (.22) | 0.32 | 575 | 295 | 37 |

*Significant differences:
$^{a-b}$ p < .3;
$^{c-d}$ p < .1;
$^{e-f}$ p < .05;

Haplotype Analysis

In order to estimate the effect of both markers, we constructed haplotypes and repeated the analysis. Three common haplotypes were identified: 1 (1_1), 2 (2_1) and 3 (2—2). The combined effects of the three substitutions were estimated as haplotype substitution effects. Contrasts between haplotypes were estimated from a model including sire (random), slaughter date and one variable for each haplotype with values −1, 0 and 1 corresponding to the animal having 0, 1 or 2 copies of the haplotype in question. The haplotype substitution effects were presented as deviations from the effect of haplotype 3 which was set arbitrary to 0.

Haplotype analysis on each population and across the lines revealed several interesting associations (Table 9). The difference between haplotype 1 and 2 reflects the effect of the Hpy188I site and the differences between haplotype 2 and 3 are due to the PvuII site. In summary, based on haplotype analysis we revealed the following effects (taking in account contrast P values lower than 0.10):

CAST Hpy88I has effects (or is in linkage disequilibrium with QTL) on: days on test (Large White), Henessey probe backfat thickness, aloca backfat (Duroc), firmness (Composite —P=0.0008), life time daily gain (LDG) (Duroc, all lines), Henessey probe rib thickness (Composite, all lines), daily gain while on test (TDG) (Duroc, all lines) and the weight of the end of the test (Duroc, all lines).

CAST-PvuII has effects (or is in linkage disequilibrium with QTL) on: Henessey probe loin depth (Large White, Composite), aloca backfat (Large White), days on test (Large White), life time daily gain (Duroc), daily gain while on test (Duroc) and the weight of the end of the test (Duroc), Henessey probe backfat thickness (Duroc), Henessey probe rib thickness, muscle depth at the end of the test and lean meat % of the carcass (Composite).

Effects of both markers on: marbling (Composite), percentage drip loss (Composite; P=0.04; haplotype 1 is associated with a lower substitution effect), Henessey probe loin depth (Composite, P=0.008; haplotype 1 is associated with a high substitution effect; Duroc, haplotype 1 is associated with a higher substitution effect), firmness (all; P=0.06; haplotype 1 is associated with a lower substitution effect), life time daily gain (Large White), daily gain while on test (Large White) and the weight of the end of the test (Large White —P=0.009-haplotype 1 is associated with a higher substitution effect; all lines—P=0.07—haplotype 1 is associated with a higher substitution effect), lean meat % of the carcass (Composite) and muscle depth at the end of the test (Large White).

TABLE 9

Haplotype analysis. Meat quality data set A.

| line | trait | mean (s.e.) | s.d. | estimate hap1 | hap2 | Hap3 | contrast p values hap1 vs 2 | hap 1 vs 3 | Hap2 vs 3 |
|---|---|---|---|---|---|---|---|---|---|
| Large White | hpromeat | 50.30 (0.70) | 12.3 | −0.39 | −1.65 | 0 | 0.13 | 0.52 | 0.05 |
|  | aloc_f | 13.33 (0.17) | 3.14 | 0.31 | 0.69 | 0 | 0.32 | 0.28 | 0.09 |
|  | endwt | 109.2 (0.36) | 6.53 | 1.52 | 0.81 | 0 | 0.37 | 0.009 | 0.31 |
|  | days | 171.0 (0.79) | 10.2 | −0.34 | −2.86 | 0 | 0.10 | 0.78 | 0.08 |
|  | ldg | 644.7 (2.24) | 41.2 | 6.89 | 5.25 | 0 | 0.73 | 0.05 | 0.28 |
|  | tdg | 844.1 (3.83) | 69.6 | 13.35 | 7.03 | 0 | 0.42 | 0.02 | 0.38 |
|  | us_md | 59.02 (0.39) | 7.04 | −1.42 | −0.92 | 0 | 0.54 | 0.02 | 0.27 |
| Duroc | hprofat | 14.03 (0.21) | 3.3 | 0.22 | 1.20 | 0 | 0.09 | 0.60 | 0.09 |
|  | hpromeat | 51.19 (0.46) | 7.2 | 3.30 | 1.77 | 0 | 0.25 | 0.0008 | 0.27 |
|  | aloc_f | 12.78 (0.18) | 2.92 | −0.24 | 0.80 | 0 | 0.02 | 0.45 | 0.12 |
|  | endwt | 106.0 (0.67) | 10.6 | −0.63 | −4.58 | 0 | 0.011 | 0.58 | 0.014 |
|  | ldg | 646.4 (3.78) | 60 | −4.75 | −28.08 | 0 | 0.008 | 0.46 | 0.008 |
|  | tdg | 823.6 (6.80) | 102 | −9.00 | −33.10 | 0 | 0.08 | 0.39 | 0.05 |
| Composite | firmness | 2.92 (0.10) | 1.01 | −0.20 | 0.19 | 0 | 0.0008 | 0.11 | 0.18 |
|  | drippct | 2.14 (0.11) | 1.32 | −0.52 | −0.39 | 0 | 0.50 | 0.04 | 0.15 |
|  | hpromeat | 63.33 (0.64) | 9.91 | 3.10 | 3.92 | 0 | 0.39 | 0.008 | 0.002 |
|  | marbling | 2.21 (0.07) | 0.87 | −0.25 | −0.12 | 0 | 0.19 | 0.04 | 0.34 |
|  | hprorib | 14.30 (0.44) | 4.25 | −0.93 | −2.52 | 0 | 0.08 | 0.34 | 0.03 |
|  | LMprct | 47.24 (0.14) | 1.33 | 0.64 | 0.93 | 0 | 0.27 | 0.03 | 0.006 |
|  | us_md | 65.96 (0.50) | 8.41 | 1.14 | 1.90 | 0 | 0.26 | 0.19 | 0.04 |
| All lines | firmness | 3.05 (0.04) | 1.03 | −0.07 | −0.01 | 0 | 0.13 | 0.06 | 0.92 |
|  | hprorib | 14.90 (0.14) | 4.04 | 0.24 | −0.29 | 0 | 0.09 | 0.38 | 0.42 |
|  | endwt | 110.2 (0.23) | 8.89 | 0.67 | −0.21 | 0 | 0.04 | 0.07 | 0.66 |
|  | ldg | 662.7 (1.46) | 55.4 | 2.84 | −3.11 | 0 | 0.02 | 0.21 | 0.30 |
|  | tdg | 852.3 (2.44) | 83.1 | 4.20 | −6.03 | 0 | 0.02 | 0.27 | 0.23 |

Comparing the haplotype results with the single marker association results we can see as expected for the significant traits the same direction in the phenotype variation. For example, in the case of firmness, allele CAST-Hpy188I-1 is associated with lower firmness compared to the 2 allele. The same result was revealed by haplotype analysis. Haplotype 1 was also found to be the preferred haplotype in the B×Y population (see Example 3).

Trait Description—Data Set A

Firmness—subjective score of loin firmness (1 to 3)—lower is better.

Percentage drip loss (Drpprct)—amount of moisture lost from the longissimus muscle during 48 h.—lower is better.

Henessey probe loin depth (hpromeat)—higher is better.

Muscle depth at the end of the test (us_md)—higher is better

Daily gain while on test (TDG)—g/day—higher is better

Life time daily gain (LDG)—g/day—higher is better

Weight of the end of the test (endwt)

Lean meat % of the carcass (LMprct)

Days on test (days)

Henessey probe backfat thickness (hprofat)

Aloca backfat (aloc_f)—backfat thickness p2 position.

Henessey probe rib thickness (hprorib)

2. Meat Quality Data Set B.

The individuals sampled for this study represent common commercial (slaughter pig) pigs resulting from crosses involving three or more pure lines. Animals were harvested in a commercial abattoir. Phenotypic data was collected for several subjective and non-subjective meat quality traits.

Loins from each individual were aged for exactly 14 days from the date when the carcasses were cut into primals. After 14 days of aging, purge loss, cooking loss, drip loss, moisture %, intramuscular fat % (IMF) and shear force were measured.

For the individual marker analysis a linear model was used with product (combination of sireline and damline) as fixed effect. The genotype was entered as fixed effect to estimate Least Squares Means. Single marker association analysis revealed significant association for tenderness and tenderness related traits:

CAST Hpy188I has effects on: cooking loss_% (P=0.0004; genotype 11 has a lower least square mean value; there is a 4.26% difference between the homozygotes LS means); moisture % (P=0.08; 11 has a lower LS mean value); subjective juiciness and tenderness score (P=0.06-0.07; genotype 11 has a higher value). There is also evidence for an effect on shear force (P=0.16) difference between the homozygotes =0.23 (Table 10).

CAST-PvuII has effects on: loin pH (P=0.06) and juiciness score (P=0.04; genotype 11 has a higher LS mean value) (Table 11).

TABLE 10

Analysis of meat quality and production traits with CAST Hpy 188I - Meat quality data set B.

| Trait | Mean (s.e.) | $\sigma_p$ | No. animals 11 | 12 | 22 | LSmeans (s.e.) 11 | 12 | 22 | geno p |
|---|---|---|---|---|---|---|---|---|---|
| drip_% | 1.72 (0.04) | 0.6 | 39 | 105 | 48 | 1.62 (0.11) | 1.66 (0.07) | 1.72 (0.10) | 0.73 |
| Shear Force | 1.91 (0.04) | 0.54 | 39 | 106 | 47 | 1.73 (0.10) a c | 1.90 (0.06) b | 1.96 (0.09) d | 0.16 |
| Cooking loss_% | 24.09 (0.35) | 4.96 | 39 | 106 | 48 | 22.29 (0.90) a m | 23.83 (0.57) b i | 26.55 (0.82) n j | 0.0004 |
| Moisture_% | 74.87 (0.05) | 0.74 | 39 | 106 | 48 | 74.57 (0.13) e c | 74.88 (0.08) f | 74.88 (0.12) d | 0.08 |
| Subjective Tenderness score | 7.39 (0.09) | 1.34 | 39 | 106 | 46 | 7.68 (0.24) e a | 7.09 (0.15) f | 7.21 (0.22) b | 0.07 |
| Subjective Juiciness score | 8.09 (0.08) | 1.17 | 39 | 106 | 46 | 8.32 (0.21) c e | 7.91 (0.13) d | 7.72 (0.19) f | 0.06 |

* Significant differences:
a-b p < .3;
c-d p < .1;
e-f p < .05;
g-h p < .01;
i-j p < .005;
m-n p < .0005

TABLE 11

Analysis of meat quality and production traits with CAST PvuII - Meat quality data set B.

| Trait | Mean (s.e.) | $\sigma_p$ | No. animals 11 | 12 | 22 | LSmeans (s.e.) 11 | 12 | 22 | geno p |
|---|---|---|---|---|---|---|---|---|---|
| LoinpH | 5.73 (0.01) | 0.18 | 78 | 64 | 16 | 5.72 (0.03) e | 5.70 (0.03) e | 5.60 (0.05) f | 0.06 |
| Drip_% | 1.72 (0.04) | 0.6 | 95 | 86 | 23 | 1.64 (0.08) | 1.68 (0.08) | 1.77 (0.14) | 0.66 |
| Shear Force | 1.91 (0.04) | 0.54 | 96 | 86 | 22 | 1.87 (0.07) | 1.90 (0.07) | 1.89 (0.12) | 0.93 |
| Cooking loss_% | 24.09 (0.35) | 4.96 | 96 | 86 | 23 | 23.67 (0.63) e | 24.04 (0.63) c | 26.00 (1.11) f d | 0.14 |
| Fat_% | 2.00 (0.05) | 0.68 | 78 | 71 | 18 | 1.87 (0.10) | 1.95 (0.09) | 1.91 (0.17) | 0.77 |
| Subjective Tenderness score | 7.39 (0.09) | 1.34 | 96 | 85 | 22 | 7.44 (0.17) c | 7.08 (0.17) d | 7.15 (0.30) | 0.18 |
| Subjective Juiciness score | 8.09 (0.08) | 1.17 | 96 | 85 | 22 | 8.22 (0.15) e | 7.84 (0.15) f | 7.66 (0.27) f | 0.04 |

* Significant differences:
a-b p < .3;
c-d p < .1;
e-f p < .05;
g-h p < .01;
i-j p < .005.

Haplotype Analysis

Three common haplotypes were identified: 1, 2 and 3. The combined effects of the three substitutions were estimated as haplotype substitution effects. A linear model was used with product (combination of sireline and damline) as fixed effect. Contrasts between haplotypes were estimated from a model in which we used one variable for each haplotype with values −1, 0 and 1 corresponding to the animal having 0, 1 or 2 copies of the haplotype in question. The haplotype substitution effects were presented as deviations from the effect of haplotype 3 which was set arbitrary to 0 (Table 12).

CAST Hpy188I has effects on: shear force (P=0.04; haplotype 1 has lower substitution effect), cooking loss (P=0.0004; haplotype 1 has a lower substitution effect).

effects of both markers on: cooking loss (P=0.002; haplotype 1 has a lower substitution effect), subjective tenderness (P=0.09; haplotype 1 is associated with a higher substitution effect) and juiciness score (P=0.008; haplotype 1 has a higher substitution effect).

TABLE 12

Haplotype analysis - Meat quality data set B.

| | | | estimate | | | contrast p values | | |
|---|---|---|---|---|---|---|---|---|
| Trait | mean (s.e.) | s.d. | hap1 | hap2 | hap3 | hap1 vs 2 | hap 1 vs 3 | Hap2 vs 3 |
| Loin pH | 5.73 (0.02) | 0.18 | 0.055 | 0.026 | 0 | 0.34 | 0.03 | 0.37 |
| Shear Force | 1.92 (0.04) | 0.55 | −0.074 | 0.097 | 0 | 0.04 | 0.28 | 0.22 |
| Cooking loss_% | 24.23 (0.36) | 5.01 | −1.916 | 0.727 | 0 | 0.0004 | 0.002 | 0.30 |
| Moisture_% | 74.87 (0.05) | 0.76 | −0.151 | −0.001 | 0 | 0.18 | 0.10 | 0.99 |
| Subjective Tenderness score | 7.33 (0.10) | 1.32 | 0.276 | 0.199 | 0 | 0.69 | 0.09 | 0.29 |
| Subjective Juiciness score | 8.02 (0.08) | 1.14 | 0.381 | 0.253 | 0 | 0.45 | 0.008 | 0.12 |

Trait Description—Data Set B

Cooking loss %—measured in the 14 days aged longissimus muscle at 80° C. Juiciness—moisture feeling inside the mouth as a result of the chewing (subjective). Tenderness—force required to bite through the loin sample (subjective). Shear Force—measurement of the tenderness of the broiled chops—lower is better.

3. Meat Quality Data Set C.

This set consists in gilts from 10 different commercial lines. A large number of meat quality traits were measured including a large set of sensory and texture traits, starting with juiciness, fibrosity, etc., and ending up with acceptance.

For the individual marker association analysis a mixed model was used with line and slaughterdate as fixed effects and sire as random effect. The genotype was entered as fixed effect to estimate Least Squares Means. (Table 13 and 14). Single marker association analysis revealed the following significant associations:

CAST Hpy188I has effects on the sensory and texture traits like: crumbliness (P=0.05; genotype 11 is associated with a higher LS mean value) and fibrosity (P=0.03; genotype 11 has a lower value); cooking loss was not significant (P=0.18) but genotype 11 has a lower value and the difference between homozygotes is close to significance (P<0.10).

CAST-PvuII has effects on: intramuscular fat (Gluteus medius) (P=0.04; genotype 11 is significantly leaner) and firmness (P=0.05).

TABLE 13

Analysis of meat quality and production traits with CAST Hpy 188I - Meat quality data set C.

| | | | No. animals | | | LSmeans (s.e.) | | | geno |
|---|---|---|---|---|---|---|---|---|---|
| Trait | Mean (s.e.) | $\sigma_p$ | 11 | 12 | 22 | 11 | 12 | 22 | p |
| s_crumbli | 4.38 (0.03) | 0.8 | 162 | 235 | 183 | 4.54 (0.07) c e | 4.40 (0.05) d a | 4.31 (0.06) f b | 0.05 |
| cooking loss | 33.70 (0.12) | 2.29 | 96 | 136 | 103 | 33.37 (0.21) a c | 33.71 (0.16) b | 33.94 (0.20) d | 0.18 |
| s_fibrosity | 3.35 (0.03) | 0.81 | 162 | 235 | 183 | 3.24 (0.06) e | 3.43 (0.05) f | 3.42 (0.06) f | 0.03 |
| t_gumines | 6.25 (0.07) | 1.17 | 70 | 108 | 83 | 6.01 (0.15) e | 6.45 (0.12) f a | 6.23 (0.15) b | 0.05 |

* Significant differences:
a-b p < .3;
c-d p < .1;
e-f p < .05;
g-h p < .01;
i-j p < .005.

TABLE 14

Analysis of meat quality and production traits with CAST PvuII - Meat quality data set C.

| | | | No. animals | | | LSmeans (s.e.) | | | geno |
|---|---|---|---|---|---|---|---|---|---|
| Trait | Mean (s.e.) | $\sigma_p$ | 11 | 12 | 22 | | (s.e.) | | p |
| IMFGm | 1.29 (0.03) | 0.48 | 151 | 110 | 58 | 1.24 (0.04) e a | 1.39 (0.04) f | 1.33 (0.06) b | 0.04 |
| Firmness | 2.93 (0.05) | 0.83 | 111 | 118 | 46 | 2.91 (0.08) c | 2.87 (0.07) e | 3.17 (0.11) d f | 0.05 |

* Significant differences:
a-b p < .3;
c-d p < .1;
e-f p < .05;
g-h p < .01;
i-j p < .005.

Haplotype Analysis

Three common haplotypes were identified: 1, 2 and 3. The combined effects of the three substitutions were estimated as haplotype substitution effects. A mixed model was used with line and slaughterdate as fixed effects and sire as random effect. Contrasts between haplotypes were estimated from a model in which we used one variable for each haplotype with values −1, 0 and 1 corresponding to the animal having 0, 1 or 2 copies of the haplotype in question. The haplotype substitution effects were presented as deviations from the effect of haplotype 3 which was set arbitrary to 0 (Table 15). Based on the contrast between the haplotype effects we were able to reveal the effect of each marker on several meat quality traits, and it is attributed separately, based on the contrast between the haplotype's effects:

CAST Hpy188I has effects on several sensory and texture traits: hardness (P=0.004); crumbliness (P<0.0001, haplotype 1 is associated with a higher substitution effect); juiciness (P=0.07, haplotype 1 has a higher substitution effect); fibrosity (P=0.003); acceptance (P=0.005); guminess (P=0.02); cooking loss (P=0.11; haplotype 1 has a lower substitution effect).

CAST-PvuII has effects on: hardness (P=0.0005); crumbliness (P=0.0005); fibrosity (P=0.02); acceptance (P=0.003) and guminess (P=0.02).

lotype 1 is associated with faster growth. These effects could be related to the effect of Calpastatin/calpain system on protein turnover or reflect linkage disequilibrium with another locus directly impacting these traits. It is possible to utilize the CAST markers (through linkage disequilibrium) to select for these traits.

In the Composite line and the across lines analysis (data set A), a significant effect was found for firmness. Haplotype 1 was associated with lower substitution effect for firmness, the same haplotype was also found to be the preferred haplotype in the B×Y $F_2$ resource population (Example 3).

In the Composite line (data set A) a significant effect was found for drip loss; signs of associations for this particular trait were also found in other lines/data sets.

Meat quality data set B revealed very significant effects on cooking loss, significant differences in instron force and subjective tenderness measures. Using haplotype analysis we were able to detect a highly significant 5.29% difference in cooking loss between the homozygote classes.

Both markers have significant effects on several tenderness and tenderness related measures on meat quality in set C. For one of these traits, for example, —acceptability—a highly significant difference was revealed between the substitution effects of the worst and the best haplotype.

TABLE 15

Haplotype analysis - Meat quality data set C.

| Trait | mean (s.e.) | s.d. | estimate hap1 | hap3 | hap4 | contrast p values hap1 vs 2 | hap 1 vs 3 | Hap2 vs 3 |
|---|---|---|---|---|---|---|---|---|
| S_hardness | 4.18 (0.04) | 0.88 | 0.075 | 0.284 | 0 | 0.004 | 0.23 | 0.0005 |
| S_crumbliness | 4.39 (0.03) | 0.8 | 0.007 | −0.256 | 0 | <.0001 | 0.91 | 0.0005 |
| cooking loss | 33.73 (0.12) | 2.23 | −0.200 | 0.140 | 0 | 0.11 | 0.28 | 0.57 |
| S_juiciness | 3.11 (0.03) | 0.74 | 0.016 | −0.095 | 0 | 0.07 | 0.75 | 0.16 |
| S_fibrosity | 3.35 (0.03) | 0.8 | −0.019 | 0.164 | 0 | 0.003 | 0.72 | 0.02 |
| S_acceptance | 4.39 (0.04) | 0.85 | −0.037 | −0.239 | 0 | 0.005 | 0.54 | 0.003 |
| t_guminess | 6.22 (0.07) | 1.17 | 0.021 | 0.401 | 0 | 0.02 | 0.87 | 0.02 |

Trait Description—Data Set C

Cooking loss—mesured in the longissimus muscle at 80° C.—lower is better.

Intramuscular fat (IMFGm)—measured by NIT Gluteus Medius muscle.

Hardness—force required to bite through the loin sample—lower is better.

Fibrosity—textural property measured by ease with which a substance can be separated—lower is better.

Juiciness—moisture feeling inside the mouth as a result of the chewing—higher is better.

Acceptability—or acceptance: an experience characterized by a positive attitude —higher is better.

Crumbliness—textural property characterized by ease with which a substance can be separated into smaller particles during the chewing—higher is better.

Guminess—was defined as the product of hardness×cohesiveness—lower is better.

These results further support the findings (Example 3) indicating that the CAST Hpy188I and PvuII polymorphisms are useful as markers in selection programs for tenderness and/or related meat quality traits. Haplotype 1 is the preferred haplotype for juiciness, tenderness and firmness; CAST Hpy188I seems to have slightly larger effects than PvuII.

In addition, there are effects on growth/loin depth in some populations and in the across lines analysis (dataset A). Hap- In general, haplotype 1 is associated with a more tender, juicy meat; less cooking loss and firmness and more acceptable pork and can therefore be used to select for improved meat quality.

REFERENCES

All references cited herein are hereby incorporated in their entirety by reference. This includes but is not limited to:

Alverna, M., De Tulio, R., Passalacqua, M., Salamino, F., Pontremoli, S., Melloni, E., 2001, Changes in intracellular calpastatin localization are mediated by reversible phosphorylation, Biochem. J. (2001) 354, 25-30.

Ernst C. W., Robic A., Yerle M., Wang L., Rothschild M. F., 1998 Mapping of calpastatin and three microsatellites to porcine chromosome 2q2.1-q2.4., Anim. Genet. 29 212-215.

Ma, H., Yang, H. Q, Takano, E., Hatanaka, M., Maki, M., 1994, Amino-terminal conserved region in proteinase inhibitor domain of calpastatin potentiates its calpain inhibitory activity by interacting with calmodulin-like domain of proteinase. J. Biol. Chem. 268:24430-24436.

Malek M., J. C. M. Dekkers, H. K. Lee, T. J. Baas, K. Prusa, E. Huff-Lonergan, M. F. Rothschild (2001). A molecular genome scan analysis to identify chromosomal region influencing economic traits in the pig. II. Meat and muscle composition. Mammalian Genome 12, 637-645.

What is claimed is:

1. A method for identifying a meat quality trait that is statistically significantly associated with a pig calpastatin (CAST) gene allele in a particular breed, strain, population or group of pigs, said method comprising:
   obtaining sample genetic material from said pigs in a particular breed, strain, population, or group, said genetic material comprising nucleic acids encoding the pig CAST gene;
   detecting in said genetic material the presence of first CAST gene alleles which have an adenine at the position corresponding to position 812 of SEQ ID NO: 1, and second CAST gene alleles which have a guanine at the position corresponding to position 812 of SEQ ID NO: 1; and
   correlating whether a statistically significant association between the detected CAST gene alleles and a meat quality trait-exists in said breed, strain, population or group.

2. The method of claim 1 wherein the presence of a guanine at nucleotide position 812 of SEQ ID NO: 1 is identifiable by a Hpyl88I restriction enzyme or a restriction fragment length polymorphism.

3. The method of claim 1 wherein said detecting is selected from the group consisting of: restriction fragment length polymorphism (RFLP) analysis, minisequencing, MALD-TOF, SINE, heteroduplex analysis, one base extension methods, single strand conformational polymorphism (SSCP) analysis, denaturing gradient gel electrophoresis (DGGE) and temperature gradient gel electrophoresis (TGGE).

4. The method of claim 1 further comprising amplifying a portion of the CAST which contains said alleles.

5. The method of claim 4 wherein said amplification includes the steps of:
   selecting a forward and a reverse sequence primer capable of amplifying a region of the CAST gene which contains a polymorphic Hpyl88I site.

6. The method of claim 5 wherein said forward and reverse primers are selected from primer SEQ ID NO: 11 and primer SEQ ID NO: 12.

* * * * *

UNITED STATES PATENT AND TRADEMARK OFFICE
CERTIFICATE OF CORRECTION

PATENT NO.        : 7,625,703 B2                                    Page 1 of 1
APPLICATION NO.   : 11/565337
DATED             : December 1, 2009
INVENTOR(S)       : Rothschild et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 429 days.

Signed and Sealed this

Second Day of November, 2010

David J. Kappos
*Director of the United States Patent and Trademark Office*

SEQUENCE LISTING

<160> NUMBER OF SEQ ID NOS: 25

<210> SEQ ID NO 1
<211> LENGTH: 2159
<212> TYPE: DNA
<213> ORGANISM: Sus scrofa
<220> FEATURE:
<221> NAME/KEY: CDS
<222> LOCATION: (67)..(2139)
<223> OTHER INFORMATION:

<400> SEQUENCE: 1

```
tctctcggcc gggaagccag aagcagagta tcgccttcct ctgcttcaac gagcaagtct        60 tccagt atg aat ccc aca gaa acc aag gct gta aaa aca gaa cct gaa          108
       Met Asn Pro Thr Glu Thr Lys Ala Val Lys Thr Glu Pro Glu
       1               5                   10 aag aag tca caa tca act aag cca tct gtg gtt cat gag aaa aaa acc        156
Lys Lys Ser Gln Ser Thr Lys Pro Ser Val Val His Glu Lys Lys Thr
15                  20                  25                  30 caa gaa gta aag cca aag gaa cac cca gag cca aaa agc cta ccc acg        204
Gln Glu Val Lys Pro Lys Glu His Pro Glu Pro Lys Ser Leu Pro Thr
                35                  40                  45 cac tca gca gat gca ggg agc aag cgt gct cat aaa gaa aaa gca gtt        252
His Ser Ala Asp Ala Gly Ser Lys Arg Ala His Lys Glu Lys Ala Val
            50                  55                  60 tcc aga tct aat gag cag cca aca tca gag aaa tca aca aaa cca aag        300
Ser Arg Ser Asn Glu Gln Pro Thr Ser Glu Lys Ser Thr Lys Pro Lys
        65                  70                  75 gct aaa cca cag gac ccg acc ccc agt gat gga aag ctt tct gtt act        348
Ala Lys Pro Gln Asp Pro Thr Pro Ser Asp Gly Lys Leu Ser Val Thr
    80                  85                  90 ggt gta tct gca gca tct ggc aaa cca gct gag acg aaa aaa gat gat        396
Gly Val Ser Ala Ala Ser Gly Lys Pro Ala Glu Thr Lys Lys Asp Asp
95                  100                 105                 110 aaa tca tta aca tcg tct gta cca gct gaa tcc aaa tca agt aaa cca        444
Lys Ser Leu Thr Ser Ser Val Pro Ala Glu Ser Lys Ser Ser Lys Pro
                115                 120                 125 tca gga aag tca gat atg gat gct gct ttg gat gac tta ata gac act        492
Ser Gly Lys Ser Asp Met Asp Ala Ala Leu Asp Asp Leu Ile Asp Thr
            130                 135                 140 tta gga gga cct gaa gaa act gag gaa gat aat aca aca tat act gga        540
Leu Gly Gly Pro Glu Glu Thr Glu Glu Asp Asn Thr Thr Tyr Thr Gly
        145                 150                 155 cct gaa gtt ttg gat cca atg agt tct acc tat ata gag gaa ttg ggt        588
Pro Glu Val Leu Asp Pro Met Ser Ser Thr Tyr Ile Glu Glu Leu Gly
    160                 165                 170 aaa aga gaa gtc aca ctt cct cca aaa tat agg gaa ttg ttg gat aaa        636
Lys Arg Glu Val Thr Leu Pro Pro Lys Tyr Arg Glu Leu Leu Asp Lys
175                 180                 185                 190 aaa gaa ggg att cca gtg cct cct cca gac act tcg aaa ccc ctg ggg        684
Lys Glu Gly Ile Pro Val Pro Pro Pro Asp Thr Ser Lys Pro Leu Gly
                195                 200                 205 ccc gat gat gcc atc gat gcc ttg tca tta gac ttg acc tgc agt tct        732
Pro Asp Asp Ala Ile Asp Ala Leu Ser Leu Asp Leu Thr Cys Ser Ser
            210                 215                 220 cct aca gct gat ggg aag aaa acc gag aaa gag aaa tct act ggg gag        780
Pro Thr Ala Asp Gly Lys Lys Thr Glu Lys Glu Lys Ser Thr Gly Glu
        225                 230                 235
```

```
gtt ttg aaa gct cag tct gtt ggg gta atc aga agc gct gct gct cca      828
Val Leu Lys Ala Gln Ser Val Gly Val Ile Arg Ser Ala Ala Ala Pro
    240             245                 250 ccc cac gag aaa aaa aga agg gtg gaa gag gac acg atg agt gat caa      876
Pro His Glu Lys Lys Arg Arg Val Glu Glu Asp Thr Met Ser Asp Gln
255                 260                 265                 270 gca ctg gag gct ttg tca gct tcc ctg ggc agc cgg aag tca gaa ccc      924
Ala Leu Glu Ala Leu Ser Ala Ser Leu Gly Ser Arg Lys Ser Glu Pro
                275                 280                 285 gag ctt gac ctc agc tcc att aag gaa att gat gag gca aaa gcc aaa      972
Glu Leu Asp Leu Ser Ser Ile Lys Glu Ile Asp Glu Ala Lys Ala Lys
            290                 295                 300 gaa gag aaa cta aag aag tgt ggt gaa gat gac gaa acg gtc ccg cca     1020
Glu Glu Lys Leu Lys Lys Cys Gly Glu Asp Asp Glu Thr Val Pro Pro
        305                 310                 315 gag tat aga ttg aaa cca gcc atg gat aaa gat gga aaa cca ctc ttg     1068
Glu Tyr Arg Leu Lys Pro Ala Met Asp Lys Asp Gly Lys Pro Leu Leu
    320                 325                 330 cca gag gct gaa gaa aaa ccc aag ccc ctg agt gaa tca gaa ctc att     1116
Pro Glu Ala Glu Glu Lys Pro Lys Pro Leu Ser Glu Ser Glu Leu Ile
335                 340                 345                 350 gac gaa ctt tcg gaa gat ttt gac cag tct aag cgt aaa gaa aaa caa     1164
Asp Glu Leu Ser Glu Asp Phe Asp Gln Ser Lys Arg Lys Glu Lys Gln
                355                 360                 365 tct aag cca act gaa aaa aca aaa gag tct cag gcc act gcc cct act     1212
Ser Lys Pro Thr Glu Lys Thr Lys Glu Ser Gln Ala Thr Ala Pro Thr
            370                 375                 380 cct gtg gga gag gcc gtg tct cgg acc tcc ttg tgc tgt gtg cag tcg     1260
Pro Val Gly Glu Ala Val Ser Arg Thr Ser Leu Cys Cys Val Gln Ser
        385                 390                 395 gca ccc cca aag cca gct acg ggc atg gtg cca gat gat gct gta gaa     1308
Ala Pro Pro Lys Pro Ala Thr Gly Met Val Pro Asp Asp Ala Val Glu
    400                 405                 410 gcc ttg gct gga agc ctg ggg aaa aag gaa gca gat cca gaa gat gga     1356
Ala Leu Ala Gly Ser Leu Gly Lys Lys Glu Ala Asp Pro Glu Asp Gly
415                 420                 425                 430 aag cct gtg gag gat aaa gtc aag gag aaa gcc aaa gaa gag gat cgt     1404
Lys Pro Val Glu Asp Lys Val Lys Glu Lys Ala Lys Glu Glu Asp Arg
                435                 440                 445 gaa aaa ctt ggt gaa aag gaa gaa acg att cct cct gat tat aga tta     1452
Glu Lys Leu Gly Glu Lys Glu Glu Thr Ile Pro Pro Asp Tyr Arg Leu
            450                 455                 460 gaa gag gtc aag gac aaa gat gga aaa act ctc ccg cac aaa gac ccc     1500
Glu Glu Val Lys Asp Lys Asp Gly Lys Thr Leu Pro His Lys Asp Pro
        465                 470                 475 aag gaa cca gtc ctg ccc ttg agt gaa gac ttc gtc ctt gat gct ttg     1548
Lys Glu Pro Val Leu Pro Leu Ser Glu Asp Phe Val Leu Asp Ala Leu
    480                 485                 490 tcc cag gac ttt gcc ggt ccc cca gcc gct tca tct ctt ttt gaa gat     1596
Ser Gln Asp Phe Ala Gly Pro Pro Ala Ala Ser Ser Leu Phe Glu Asp
495                 500                 505                 510 gct aaa ctt tca gct gcc gtc tct gaa gtg gtt tcc caa acc tca gct     1644
Ala Lys Leu Ser Ala Ala Val Ser Glu Val Val Ser Gln Thr Ser Ala
                515                 520                 525 cca acc acc cac tct gca ggt cca ccc cct gac act gtg agt gat gac     1692
Pro Thr Thr His Ser Ala Gly Pro Pro Pro Asp Thr Val Ser Asp Asp
            530                 535                 540
```

```
aaa aaa ctt gac gat gcc ctg gat cag ctt tct gac agt ctg ggg caa        1740
Lys Lys Leu Asp Asp Ala Leu Asp Gln Leu Ser Asp Ser Leu Gly Gln
            545                 550                 555 aga cag cct gac cca gat gag aac aag ccc ata gag gat aaa gtc aag        1788
Arg Gln Pro Asp Pro Asp Glu Asn Lys Pro Ile Glu Asp Lys Val Lys
560                 565                 570 gaa aaa gct gaa gct gaa cat aga gac aag ctg gga gaa aga gat gac        1836
Glu Lys Ala Glu Ala Glu His Arg Asp Lys Leu Gly Glu Arg Asp Asp
575                 580                 585                 590 act atc ccg cct gaa tat aga cat ctc ttg gat aag gat gag gag ggc        1884
Thr Ile Pro Pro Glu Tyr Arg His Leu Leu Asp Lys Asp Glu Glu Gly
                595                 600                 605 aaa tca acg aag cca ccc aca aag aaa cct gag gca cca aag aaa cct        1932
Lys Ser Thr Lys Pro Pro Thr Lys Lys Pro Glu Ala Pro Lys Lys Pro
            610                 615                 620 gaa gct gcc caa gat ccc att gat gcc ctc tca ggg gat ttt gac aga        1980
Glu Ala Ala Gln Asp Pro Ile Asp Ala Leu Ser Gly Asp Phe Asp Arg
625                 630                 635 tgt cca tca act aca gaa acc tca gag aac aca aca aag gac aaa gac        2028
Cys Pro Ser Thr Thr Glu Thr Ser Glu Asn Thr Thr Lys Asp Lys Asp
640                 645                 650 aag aag acg gct tcc aag tcc aaa gca ccc aag aat ggg ggt aaa gca        2076
Lys Lys Thr Ala Ser Lys Ser Lys Ala Pro Lys Asn Gly Gly Lys Ala
655                 660                 665                 670 aag gat tcc aca aag gca aag gag gaa act tcc aaa caa aaa tct gat        2124
Lys Asp Ser Thr Lys Ala Lys Glu Glu Thr Ser Lys Gln Lys Ser Asp
                675                 680                 685 gga aag agt aca agt taaaagttca cactattttc                              2159
Gly Lys Ser Thr Ser
            690
```

<210> SEQ ID NO 2
<211> LENGTH: 691
<212> TYPE: PRT
<213> ORGANISM: Sus scrofa

<400> SEQUENCE: 2

```
Met Asn Pro Thr Glu Thr Lys Ala Val Lys Thr Glu Pro Glu Lys Lys
1               5                   10                  15

Ser Gln Ser Thr Lys Pro Ser Val Val His Glu Lys Lys Thr Gln Glu
            20                  25                  30

Val Lys Pro Lys Glu His Pro Glu Pro Lys Ser Leu Pro Thr His Ser
        35                  40                  45

Ala Asp Ala Gly Ser Lys Arg Ala His Lys Glu Lys Ala Val Ser Arg
    50                  55                  60

Ser Asn Glu Gln Pro Thr Ser Glu Lys Ser Thr Lys Pro Lys Ala Lys
65                  70                  75                  80

Pro Gln Asp Pro Thr Pro Ser Asp Gly Lys Leu Ser Val Thr Gly Val
                85                  90                  95

Ser Ala Ala Ser Gly Lys Pro Ala Glu Thr Lys Lys Asp Asp Lys Ser
            100                 105                 110

Leu Thr Ser Ser Val Pro Ala Glu Ser Lys Ser Ser Lys Pro Ser Gly
        115                 120                 125

Lys Ser Asp Met Asp Ala Ala Leu Asp Asp Leu Ile Asp Thr Leu Gly
    130                 135                 140

Gly Pro Glu Glu Thr Glu Glu Asp Asn Thr Thr Tyr Thr Gly Pro Glu
145                 150                 155                 160
```

-continued

```
Val Leu Asp Pro Met Ser Ser Thr Tyr Ile Glu Leu Gly Lys Arg
                165                 170                 175

Glu Val Thr Leu Pro Pro Lys Tyr Arg Glu Leu Leu Asp Lys Lys Glu
            180                 185                 190

Gly Ile Pro Val Pro Pro Asp Thr Ser Lys Pro Leu Gly Pro Asp
            195                 200                 205

Asp Ala Ile Asp Ala Leu Ser Leu Asp Leu Thr Cys Ser Ser Pro Thr
210                 215                 220

Ala Asp Gly Lys Lys Thr Glu Lys Glu Lys Ser Thr Gly Glu Val Leu
225                 230                 235                 240

Lys Ala Gln Ser Val Gly Val Ile Arg Ser Ala Ala Pro Pro His
                245                 250                 255

Glu Lys Lys Arg Arg Val Glu Glu Asp Thr Met Ser Asp Gln Ala Leu
                260                 265                 270

Glu Ala Leu Ser Ala Ser Leu Gly Ser Arg Lys Ser Glu Pro Glu Leu
            275                 280                 285

Asp Leu Ser Ser Ile Lys Glu Ile Asp Glu Ala Lys Ala Lys Glu Glu
            290                 295                 300

Lys Leu Lys Lys Cys Gly Glu Asp Glu Thr Val Pro Pro Glu Tyr
305                 310                 315                 320

Arg Leu Lys Pro Ala Met Asp Lys Asp Gly Lys Pro Leu Leu Pro Glu
                325                 330                 335

Ala Glu Glu Lys Pro Lys Pro Leu Ser Glu Ser Glu Leu Ile Asp Glu
            340                 345                 350

Leu Ser Glu Asp Phe Asp Gln Ser Lys Arg Lys Glu Lys Gln Ser Lys
            355                 360                 365

Pro Thr Glu Lys Thr Lys Glu Ser Gln Ala Thr Ala Pro Thr Pro Val
            370                 375                 380

Gly Glu Ala Val Ser Arg Thr Ser Leu Cys Cys Val Gln Ser Ala Pro
385                 390                 395                 400

Pro Lys Pro Ala Thr Gly Met Val Pro Asp Asp Ala Val Glu Ala Leu
                405                 410                 415

Ala Gly Ser Leu Gly Lys Lys Glu Ala Asp Pro Glu Asp Gly Lys Pro
            420                 425                 430

Val Glu Asp Lys Val Lys Glu Lys Ala Lys Glu Glu Asp Arg Glu Lys
            435                 440                 445

Leu Gly Glu Lys Glu Glu Thr Ile Pro Pro Asp Tyr Arg Leu Glu Glu
            450                 455                 460

Val Lys Asp Lys Asp Gly Lys Thr Leu Pro His Lys Asp Pro Lys Glu
465                 470                 475                 480

Pro Val Leu Pro Leu Ser Glu Asp Phe Val Leu Asp Ala Leu Ser Gln
                485                 490                 495

Asp Phe Ala Gly Pro Pro Ala Ala Ser Ser Leu Phe Glu Asp Ala Lys
                500                 505                 510

Leu Ser Ala Ala Val Ser Glu Val Val Ser Gln Thr Ser Ala Pro Thr
            515                 520                 525

Thr His Ser Ala Gly Pro Pro Asp Thr Val Ser Asp Lys Lys
            530                 535                 540

Leu Asp Asp Ala Leu Asp Gln Leu Ser Asp Ser Leu Gly Gln Arg Gln
545                 550                 555                 560

Pro Asp Pro Asp Glu Asn Lys Pro Ile Glu Asp Lys Val Lys Glu Lys
                565                 570                 575
```

```
Ala Glu Ala Glu His Arg Asp Lys Leu Gly Glu Arg Asp Asp Thr Ile
            580                 585                 590

Pro Pro Glu Tyr Arg His Leu Leu Asp Lys Asp Glu Glu Gly Lys Ser
            595                 600                 605

Thr Lys Pro Pro Thr Lys Lys Pro Glu Ala Pro Lys Lys Pro Glu Ala
            610                 615                 620

Ala Gln Asp Pro Ile Asp Ala Leu Ser Gly Asp Phe Asp Arg Cys Pro
625                 630                 635                 640

Ser Thr Thr Glu Thr Ser Glu Asn Thr Thr Lys Asp Lys Asp Lys Lys
            645                 650                 655

Thr Ala Ser Lys Ser Lys Ala Pro Lys Asn Gly Gly Lys Ala Lys Asp
            660                 665                 670

Ser Thr Lys Ala Lys Glu Glu Thr Ser Lys Gln Lys Ser Asp Gly Lys
            675                 680                 685

Ser Thr Ser
    690

<210> SEQ ID NO 3
<211> LENGTH: 2159
<212> TYPE: DNA
<213> ORGANISM: Sus scrofa
<220> FEATURE:
<221> NAME/KEY: CDS
<222> LOCATION: (67)..(2139)
<223> OTHER INFORMATION:

<400> SEQUENCE: 3
tctctcggcc gggaagccag aagcagagta tcgccttcct ctgcttcaac gagcaagtct        60 tccagt atg aat ccc aca gaa acc aag gct gta aaa aca gaa cct gaa         108
       Met Asn Pro Thr Glu Thr Lys Ala Val Lys Thr Glu Pro Glu
       1               5                   10 aag aag tca caa tca act aag cca tct gtg gtt cat gag aaa aaa acc       156
Lys Lys Ser Gln Ser Thr Lys Pro Ser Val Val His Glu Lys Lys Thr
15                  20                  25                  30 caa gaa gta aag cca aag gaa cac cca gag cca aaa agc cta ccc acg       204
Gln Glu Val Lys Pro Lys Glu His Pro Glu Pro Lys Ser Leu Pro Thr
                35                  40                  45 cac tca gca gat gca ggg agc aag cgt gct cat aaa gaa aaa gca gtt       252
His Ser Ala Asp Ala Gly Ser Lys Arg Ala His Lys Glu Lys Ala Val
            50                  55                  60 tcc aga tct aat gag cag cca aca tca gag aaa tca aca aaa cca aag       300
Ser Arg Ser Asn Glu Gln Pro Thr Ser Glu Lys Ser Thr Lys Pro Lys
        65                  70                  75 gct aaa cca cag gac ccg acc ccc agt gat gga aag ctt tct gtt act       348
Ala Lys Pro Gln Asp Pro Thr Pro Ser Asp Gly Lys Leu Ser Val Thr
    80                  85                  90 ggt gta tct gca gca tct ggc aaa cca gct gag acg aaa aaa gat gat       396
Gly Val Ser Ala Ala Ser Gly Lys Pro Ala Glu Thr Lys Lys Asp Asp
95                  100                 105                 110 aaa tca tta aca tcg tct gta cca gct gaa tcc aaa tca agt aaa cca       444
Lys Ser Leu Thr Ser Ser Val Pro Ala Glu Ser Lys Ser Ser Lys Pro
                115                 120                 125 tca gga aag tca gat atg gat gct gct ttg gat gac tta ata gac act       492
Ser Gly Lys Ser Asp Met Asp Ala Ala Leu Asp Asp Leu Ile Asp Thr
            130                 135                 140 tta gga gga cct gaa gaa act gag gaa gat aat aca aca tat act gga       540
Leu Gly Gly Pro Glu Glu Thr Glu Glu Asp Asn Thr Thr Tyr Thr Gly
        145                 150                 155
```

```
cct gaa gtt ttg gat cca atg agt tct acc tat ata gag gaa ttg ggt      588
Pro Glu Val Leu Asp Pro Met Ser Ser Thr Tyr Ile Glu Glu Leu Gly
    160                 165                 170 aaa aga gaa gtc aca ctt cct cca aaa tat agg gaa ttg ttg gat aaa      636
Lys Arg Glu Val Thr Leu Pro Pro Lys Tyr Arg Glu Leu Leu Asp Lys
175                 180                 185                 190 aaa gaa ggg att cca gtg cct cct cca gac act tcg aaa ccc ctg ggg      684
Lys Glu Gly Ile Pro Val Pro Pro Pro Asp Thr Ser Lys Pro Leu Gly
                    195                 200                 205 ccc gat gat gcc atc gat gcc ttg tca tta gac ttg acc tgc agt tct      732
Pro Asp Asp Ala Ile Asp Ala Leu Ser Leu Asp Leu Thr Cys Ser Ser
                210                 215                 220 cct aca gct gat ggg aag aaa acc gag aaa gag aaa tct act ggg gag      780
Pro Thr Ala Asp Gly Lys Lys Thr Glu Lys Glu Lys Ser Thr Gly Glu
            225                 230                 235 gtt ttg aaa gct cag tct gtt ggg gta atc aga agc gct gct gct cca      828
Val Leu Lys Ala Gln Ser Val Gly Val Ile Arg Ser Ala Ala Ala Pro
        240                 245                 250 ccc cac gag aaa aaa aga agg gtg gaa gag gac acg atg agt gat caa      876
Pro His Glu Lys Lys Arg Arg Val Glu Glu Asp Thr Met Ser Asp Gln
255                 260                 265                 270 gca ctg gag gct ttg tca gct tcc ctg ggc agc cgg aag tca gaa ccc      924
Ala Leu Glu Ala Leu Ser Ala Ser Leu Gly Ser Arg Lys Ser Glu Pro
                275                 280                 285 gag ctt gac ctc agc tcc att aag gaa att gat gag gca aaa gcc aaa      972
Glu Leu Asp Leu Ser Ser Ile Lys Glu Ile Asp Glu Ala Lys Ala Lys
                290                 295                 300 gaa gag aaa cta aag aag tgt ggt gaa gat gac gaa acg gtc ccg cca     1020
Glu Glu Lys Leu Lys Lys Cys Gly Glu Asp Asp Glu Thr Val Pro Pro
            305                 310                 315 gag tat aga ttg aaa cca gcc atg gat aaa gat gga aaa cca ctc ttg     1068
Glu Tyr Arg Leu Lys Pro Ala Met Asp Lys Asp Gly Lys Pro Leu Leu
        320                 325                 330 cca gag gct gaa gaa aaa ccc aag ccc ctg agt gaa tca gaa ctc att     1116
Pro Glu Ala Glu Glu Lys Pro Lys Pro Leu Ser Glu Ser Glu Leu Ile
335                 340                 345                 350 gac gaa ctt tcg gaa gat ttt gac cag tct aag cgt aaa gaa aaa caa     1164
Asp Glu Leu Ser Glu Asp Phe Asp Gln Ser Lys Arg Lys Glu Lys Gln
                355                 360                 365 tct aag cca act gaa aaa aca aaa gag tct cag gcc act gcc cct act     1212
Ser Lys Pro Thr Glu Lys Thr Lys Glu Ser Gln Ala Thr Ala Pro Thr
            370                 375                 380 cct gtg gga gag gcc gtg tct cgg acc tcc ttg tgc tgt gtg cag tcg     1260
Pro Val Gly Glu Ala Val Ser Arg Thr Ser Leu Cys Cys Val Gln Ser
        385                 390                 395 gca ccc cca aag cca gct acg ggc atg gtg cca gat gat gct gta gaa     1308
Ala Pro Pro Lys Pro Ala Thr Gly Met Val Pro Asp Asp Ala Val Glu
400                 405                 410 gcc ttg gct gga agc ctg ggg aaa aag gaa gca gat cca gaa gat gga     1356
Ala Leu Ala Gly Ser Leu Gly Lys Lys Glu Ala Asp Pro Glu Asp Gly
415                 420                 425                 430 aag cct gtg gag gat aaa gtc aag gag aaa gcc aaa gaa gag gat cgt     1404
Lys Pro Val Glu Asp Lys Val Lys Glu Lys Ala Lys Glu Glu Asp Arg
                435                 440                 445 gaa aaa ctt ggt gaa aag gaa gaa acg att cct cct gat tat aga tta     1452
Glu Lys Leu Gly Glu Lys Glu Glu Thr Ile Pro Pro Asp Tyr Arg Leu
            450                 455                 460 gaa gag gtc aag gac aaa gat gga aaa act ctc ccg cac aaa gac ccc     1500
Glu Glu Val Lys Asp Lys Asp Gly Lys Thr Leu Pro His Lys Asp Pro
        465                 470                 475
```

```
aag gaa cca gtc ctg ccc ttg agt gaa gac ttc gtc ctt gat gct ttg      1548
Lys Glu Pro Val Leu Pro Leu Ser Glu Asp Phe Val Leu Asp Ala Leu
    480                 485                 490 tcc cag gac ttt gcc ggt ccc cca gcc gct tca tct ctt ttt gaa gat      1596
Ser Gln Asp Phe Ala Gly Pro Pro Ala Ala Ser Ser Leu Phe Glu Asp
495                 500                 505                 510 gct aaa ctt tca gct gcc gtc tct gaa gtg gtt tcc caa acc tca gct      1644
Ala Lys Leu Ser Ala Ala Val Ser Glu Val Val Ser Gln Thr Ser Ala
                515                 520                 525 cca acc acc cac tct gca ggt cca ccc cct gac act gtg agt gat gac      1692
Pro Thr Thr His Ser Ala Gly Pro Pro Pro Asp Thr Val Ser Asp Asp
            530                 535                 540 aaa aaa ctt gac gat gcc ctg gat cag ctt tct gac agt ctg ggg caa      1740
Lys Lys Leu Asp Asp Ala Leu Asp Gln Leu Ser Asp Ser Leu Gly Gln
        545                 550                 555 aga cag cct gac cca gat gag aac aag ccc ata gag gat aaa gtc aag      1788
Arg Gln Pro Asp Pro Asp Glu Asn Lys Pro Ile Glu Asp Lys Val Lys
    560                 565                 570 gaa aaa gct gaa gct gaa cat aga gac aag ctg gga gaa aga gat gac      1836
Glu Lys Ala Glu Ala Glu His Arg Asp Lys Leu Gly Glu Arg Asp Asp
575                 580                 585                 590 act atc ccg cct gaa tat aga cat ctc ttg gat aag gat gag gag ggc      1884
Thr Ile Pro Pro Glu Tyr Arg His Leu Leu Asp Lys Asp Glu Glu Gly
                595                 600                 605 aaa tca acg aag cca ccc aca aag aaa cct gag gca cca aag aaa cct      1932
Lys Ser Thr Lys Pro Pro Thr Lys Lys Pro Glu Ala Pro Lys Lys Pro
            610                 615                 620 gaa gct gcc caa gat ccc att gat gcc ctc tca ggg gat ttt gac aga      1980
Glu Ala Ala Gln Asp Pro Ile Asp Ala Leu Ser Gly Asp Phe Asp Arg
        625                 630                 635 tgt cca tca act aca gaa acc tca gag aac aca aca aag gac aaa gac      2028
Cys Pro Ser Thr Thr Glu Thr Ser Glu Asn Thr Thr Lys Asp Lys Asp
    640                 645                 650 aag aag acg gct tcc aag tcc aaa gca ccc aag aat ggg ggt aaa gca      2076
Lys Lys Thr Ala Ser Lys Ser Lys Ala Pro Lys Asn Gly Gly Lys Ala
655                 660                 665                 670 aag gat tcc aca aag gca aag gag gaa act tcc aaa caa aaa tct gat      2124
Lys Asp Ser Thr Lys Ala Lys Glu Glu Thr Ser Lys Gln Lys Ser Asp
                675                 680                 685 gga aag agt aca agt taaaagttca cactatttc                             2159
Gly Lys Ser Thr Ser
            690

<210> SEQ ID NO 4
<211> LENGTH: 691
<212> TYPE: PRT
<213> ORGANISM: Sus scrofa

<400> SEQUENCE: 4

Met Asn Pro Thr Glu Thr Lys Ala Val Lys Thr Glu Pro Glu Lys Lys
1               5                   10                  15

Ser Gln Ser Thr Lys Pro Ser Val Val His Glu Lys Lys Thr Gln Glu
            20                  25                  30

Val Lys Pro Lys Glu His Pro Glu Pro Lys Ser Leu Pro Thr His Ser
        35                  40                  45

Ala Asp Ala Gly Ser Lys Arg Ala His Lys Glu Lys Ala Val Ser Arg
    50                  55                  60

Ser Asn Glu Gln Pro Thr Ser Glu Lys Ser Thr Lys Pro Lys Ala Lys
65                  70                  75                  80
```

-continued

```
Pro Gln Asp Pro Thr Pro Ser Asp Gly Lys Leu Ser Val Thr Gly Val
                85                  90                  95

Ser Ala Ala Ser Gly Lys Pro Ala Glu Thr Lys Lys Asp Asp Lys Ser
            100                 105                 110

Leu Thr Ser Ser Val Pro Ala Glu Ser Lys Ser Ser Lys Pro Ser Gly
        115                 120                 125

Lys Ser Asp Met Asp Ala Ala Leu Asp Asp Leu Ile Asp Thr Leu Gly
    130                 135                 140

Gly Pro Glu Glu Thr Glu Glu Asp Asn Thr Thr Tyr Thr Gly Pro Glu
145                 150                 155                 160

Val Leu Asp Pro Met Ser Ser Thr Tyr Ile Glu Leu Gly Lys Arg
                165                 170                 175

Glu Val Thr Leu Pro Pro Lys Tyr Arg Glu Leu Leu Asp Lys Lys Glu
            180                 185                 190

Gly Ile Pro Val Pro Pro Asp Thr Ser Lys Pro Leu Gly Pro Asp
        195                 200                 205

Asp Ala Ile Asp Ala Leu Ser Leu Asp Leu Thr Cys Ser Ser Pro Thr
    210                 215                 220

Ala Asp Gly Lys Lys Thr Glu Lys Glu Lys Ser Thr Gly Glu Val Leu
225                 230                 235                 240

Lys Ala Gln Ser Val Gly Val Ile Arg Ser Ala Ala Pro Pro His
                245                 250                 255

Glu Lys Lys Arg Arg Val Glu Glu Asp Thr Met Ser Asp Gln Ala Leu
            260                 265                 270

Glu Ala Leu Ser Ala Ser Leu Gly Ser Arg Lys Ser Glu Pro Glu Leu
        275                 280                 285

Asp Leu Ser Ser Ile Lys Glu Ile Asp Glu Ala Lys Ala Lys Glu Glu
    290                 295                 300

Lys Leu Lys Lys Cys Gly Glu Asp Asp Glu Thr Val Pro Pro Glu Tyr
305                 310                 315                 320

Arg Leu Lys Pro Ala Met Asp Lys Asp Gly Lys Pro Leu Leu Pro Glu
                325                 330                 335

Ala Glu Glu Lys Pro Lys Pro Leu Ser Glu Ser Glu Leu Ile Asp Glu
            340                 345                 350

Leu Ser Glu Asp Phe Asp Gln Ser Lys Arg Lys Glu Lys Gln Ser Lys
        355                 360                 365

Pro Thr Glu Lys Thr Lys Glu Ser Gln Ala Thr Ala Pro Thr Pro Val
    370                 375                 380

Gly Glu Ala Val Ser Arg Thr Ser Leu Cys Cys Val Gln Ser Ala Pro
385                 390                 395                 400

Pro Lys Pro Ala Thr Gly Met Val Pro Asp Ala Val Glu Ala Leu
                405                 410                 415

Ala Gly Ser Leu Gly Lys Lys Glu Ala Asp Pro Glu Asp Gly Lys Pro
            420                 425                 430

Val Glu Asp Lys Val Lys Glu Lys Ala Lys Glu Glu Asp Arg Glu Lys
        435                 440                 445

Leu Gly Glu Lys Glu Glu Thr Ile Pro Pro Asp Tyr Arg Leu Glu Glu
    450                 455                 460

Val Lys Asp Lys Asp Gly Lys Thr Leu Pro His Lys Asp Pro Lys Glu
465                 470                 475                 480

Pro Val Leu Pro Leu Ser Glu Asp Phe Val Leu Asp Ala Leu Ser Gln
                485                 490                 495
```

```
Asp Phe Ala Gly Pro Pro Ala Ala Ser Ser Leu Phe Glu Asp Ala Lys
            500                 505                 510

Leu Ser Ala Ala Val Ser Glu Val Val Ser Gln Thr Ser Ala Pro Thr
        515                 520                 525

Thr His Ser Ala Gly Pro Pro Asp Thr Val Ser Asp Lys Lys
    530                 535                 540

Leu Asp Asp Ala Leu Asp Gln Leu Ser Asp Ser Leu Gly Gln Arg Gln
545                 550                 555                 560

Pro Asp Pro Asp Glu Asn Lys Pro Ile Glu Asp Lys Val Lys Glu Lys
                565                 570                 575

Ala Glu Ala Glu His Arg Asp Lys Leu Gly Glu Arg Asp Asp Thr Ile
            580                 585                 590

Pro Pro Glu Tyr Arg His Leu Leu Asp Lys Asp Glu Glu Gly Lys Ser
        595                 600                 605

Thr Lys Pro Pro Thr Lys Lys Pro Glu Ala Pro Lys Lys Pro Glu Ala
    610                 615                 620

Ala Gln Asp Pro Ile Asp Ala Leu Ser Gly Asp Phe Asp Arg Cys Pro
625                 630                 635                 640

Ser Thr Thr Glu Thr Ser Glu Asn Thr Thr Lys Asp Lys Asp Lys Lys
                645                 650                 655

Thr Ala Ser Lys Ser Lys Ala Pro Lys Asn Gly Gly Lys Ala Lys Asp
            660                 665                 670

Ser Thr Lys Ala Lys Glu Glu Thr Ser Lys Gln Lys Ser Asp Gly Lys
        675                 680                 685

Ser Thr Ser
    690

<210> SEQ ID NO 5
<211> LENGTH: 2159
<212> TYPE: DNA
<213> ORGANISM: Sus scrofa
<220> FEATURE:
<221> NAME/KEY: CDS
<222> LOCATION: (67)..(2139)
<223> OTHER INFORMATION:

<400> SEQUENCE: 5
tctctcggcc gggaagccag aagcagagta tcgccttcct ctgcttcaac gagcaagtct      60 tccagt atg aat ccc aca gaa acc aag gct gta aaa aca gaa cct gaa        108
       Met Asn Pro Thr Glu Thr Lys Ala Val Lys Thr Glu Pro Glu
       1               5                   10 aag aag tca caa tca act aag cca tct gtg gtt cat gag aaa aaa acc      156
Lys Lys Ser Gln Ser Thr Lys Pro Ser Val Val His Glu Lys Lys Thr
15                  20                  25                  30 caa gaa gta aag cca aag gaa cac cca gag cca aaa agc cta ccc acg      204
Gln Glu Val Lys Pro Lys Glu His Pro Glu Pro Lys Ser Leu Pro Thr
                35                  40                  45 cac tca gca gat gca ggg agc aag cgt gct cat aaa gaa aaa gca gtt      252
His Ser Ala Asp Ala Gly Ser Lys Arg Ala His Lys Glu Lys Ala Val
            50                  55                  60 tcc aga tct aat gag cag cca aca tca gag aaa tca aca aaa cca aag      300
Ser Arg Ser Asn Glu Gln Pro Thr Ser Glu Lys Ser Thr Lys Pro Lys
        65                  70                  75 gct aaa cca cag gac ccg acc ccc agt gat gga aag ctt tct gtt act      348
Ala Lys Pro Gln Asp Pro Thr Pro Ser Asp Gly Lys Leu Ser Val Thr
    80                  85                  90 ggt gta tct gca gca tct ggc aaa cca gct gag acg aaa aaa gat gat      396
Gly Val Ser Ala Ala Ser Gly Lys Pro Ala Glu Thr Lys Lys Asp Asp
```

```
                95                  100                 105                 110
aaa tca tta aca tcg tct gta cca gct gaa tcc aaa tca agt aaa cca         444
Lys Ser Leu Thr Ser Ser Val Pro Ala Glu Ser Lys Ser Ser Lys Pro
                    115                 120                 125 tca gga aag tca gat atg gat gct gct ttg gat gac tta ata gac act         492
Ser Gly Lys Ser Asp Met Asp Ala Ala Leu Asp Asp Leu Ile Asp Thr
            130                 135                 140 tta gga gga cct gaa gaa act gag gaa gat aat aca aca tat act gga         540
Leu Gly Gly Pro Glu Glu Thr Glu Glu Asp Asn Thr Thr Tyr Thr Gly
                145                 150                 155 cct gaa gtt ttg gat cca atg agt tct acc tat ata gag gaa ttg ggt         588
Pro Glu Val Leu Asp Pro Met Ser Ser Thr Tyr Ile Glu Glu Leu Gly
            160                 165                 170 aaa aga gaa gtc aca ctt cct cca aaa tat agg gaa ttg ttg gat aaa         636
Lys Arg Glu Val Thr Leu Pro Pro Lys Tyr Arg Glu Leu Leu Asp Lys
175                 180                 185                 190 aaa gaa ggg att cca gtg cct cct cca gac act tcg aaa ccc ctg ggg         684
Lys Glu Gly Ile Pro Val Pro Pro Pro Asp Thr Ser Lys Pro Leu Gly
                        195                 200                 205 ccc gat gat gcc atc gat gcc ttg tca tta gac ttg acc tgc agt tct         732
Pro Asp Asp Ala Ile Asp Ala Leu Ser Leu Asp Leu Thr Cys Ser Ser
                210                 215                 220 cct aca gct gat ggg aag aaa acc gag aaa gag aaa tct act ggg gag         780
Pro Thr Ala Asp Gly Lys Lys Thr Glu Lys Glu Lys Ser Thr Gly Glu
            225                 230                 235 gtt ttg aaa gct cag tct gtt ggg gta atc aaa agc gct gct gct cca         828
Val Leu Lys Ala Gln Ser Val Gly Val Ile Lys Ser Ala Ala Ala Pro
        240                 245                 250 ccc cac gag aaa aaa aga agg gtg gaa gag gac acg atg agt gat caa         876
Pro His Glu Lys Lys Arg Arg Val Glu Glu Asp Thr Met Ser Asp Gln
255                 260                 265                 270 gca ctg gag gct ttg tca gct tcc ctg ggc agc cgg aag tca gaa ccc         924
Ala Leu Glu Ala Leu Ser Ala Ser Leu Gly Ser Arg Lys Ser Glu Pro
                275                 280                 285 gag ctt gac ctc agc tcc att aag gaa att gat gag gca aaa gcc aaa         972
Glu Leu Asp Leu Ser Ser Ile Lys Glu Ile Asp Glu Ala Lys Ala Lys
            290                 295                 300 gaa gag aaa cta aag aag tgt ggt gaa gat gac gaa acg gtc ccg cca        1020
Glu Glu Lys Leu Lys Lys Cys Gly Glu Asp Asp Glu Thr Val Pro Pro
                305                 310                 315 gag tat aga ttg aaa cca gcc atg gat aaa gat gga aaa cca ctc ttg        1068
Glu Tyr Arg Leu Lys Pro Ala Met Asp Lys Asp Gly Lys Pro Leu Leu
        320                 325                 330 cca gag gct gaa gaa aaa ccc aag ccc ctg agt gaa tca gaa ctc att        1116
Pro Glu Ala Glu Glu Lys Pro Lys Pro Leu Ser Glu Ser Glu Leu Ile
335                 340                 345                 350 gac gaa ctt tcg gaa gat ttt gac cag tct aag cgt aaa gaa aaa caa        1164
Asp Glu Leu Ser Glu Asp Phe Asp Gln Ser Lys Arg Lys Glu Lys Gln
                355                 360                 365 tct aag cca act gaa aaa aca aaa gag tct cag gcc act gcc cct act        1212
Ser Lys Pro Thr Glu Lys Thr Lys Glu Ser Gln Ala Thr Ala Pro Thr
            370                 375                 380 cct gtg gga gag gcc gtg tct cgg acc tcc ttg tgc tgt gtg cag tcg        1260
Pro Val Gly Glu Ala Val Ser Arg Thr Ser Leu Cys Cys Val Gln Ser
                        385                 390                 395 gca ccc cca aag cca gct acg ggc atg gtg cca gat gat gct gta gaa        1308
Ala Pro Pro Lys Pro Ala Thr Gly Met Val Pro Asp Asp Ala Val Glu
                400                 405                 410 gcc ttg gct gga agc ctg ggg aaa aag gaa gca gat cca gaa gat gga        1356
```

```
Ala Leu Ala Gly Ser Leu Gly Lys Lys Glu Ala Asp Pro Glu Asp Gly
415                 420                 425                 430 aag cct gtg gag gat aaa gtc aag gag aaa gcc aaa gaa gag gat cgt      1404
Lys Pro Val Glu Asp Lys Val Lys Glu Lys Ala Lys Glu Glu Asp Arg
                435                 440                 445 gaa aaa ctt ggt gaa aag gaa gaa acg att cct cct gat tat aga tta      1452
Glu Lys Leu Gly Glu Lys Glu Glu Thr Ile Pro Pro Asp Tyr Arg Leu
            450                 455                 460 gaa gag gtc aag gac aaa gat gga aaa act ctc ccg cac aaa gac ccc      1500
Glu Glu Val Lys Asp Lys Asp Gly Lys Thr Leu Pro His Lys Asp Pro
        465                 470                 475 aag gaa cca gtc ctg ccc ttg agt gaa gac ttc gtc ctt gat gct ttg      1548
Lys Glu Pro Val Leu Pro Leu Ser Glu Asp Phe Val Leu Asp Ala Leu
    480                 485                 490 tcc cag gac ttt gcc ggt ccc cca gcc gct tca tct ctt ttt gaa gat      1596
Ser Gln Asp Phe Ala Gly Pro Pro Ala Ala Ser Ser Leu Phe Glu Asp
495                 500                 505                 510 gct aaa ctt tca gct gcc gtc tct gaa gtg gtt tcc caa acc tca gct      1644
Ala Lys Leu Ser Ala Ala Val Ser Glu Val Val Ser Gln Thr Ser Ala
                515                 520                 525 cca acc acc cac tct gca ggt cca ccc cct gac act gtg agt gat gac      1692
Pro Thr Thr His Ser Ala Gly Pro Pro Pro Asp Thr Val Ser Asp Asp
            530                 535                 540 aaa aaa ctt gac gat gcc ctg gat cag ctt tct gac agt ctg ggg caa      1740
Lys Lys Leu Asp Asp Ala Leu Asp Gln Leu Ser Asp Ser Leu Gly Gln
        545                 550                 555 aga cag cct gac cca gat gag aac aag ccc ata gag gat aaa gtc aag      1788
Arg Gln Pro Asp Pro Asp Glu Asn Lys Pro Ile Glu Asp Lys Val Lys
    560                 565                 570 gaa aaa gct gaa gct gaa cat aga gac aag ctg gga gaa aga gat gac      1836
Glu Lys Ala Glu Ala Glu His Arg Asp Lys Leu Gly Glu Arg Asp Asp
575                 580                 585                 590 act atc ccg cct gaa tat aga cat ctc ttg gat aag gat gag gag ggc      1884
Thr Ile Pro Pro Glu Tyr Arg His Leu Leu Asp Lys Asp Glu Glu Gly
                595                 600                 605 aaa tca acg aag cca ccc aca aag aaa cct gag gca cca aag aaa cct      1932
Lys Ser Thr Lys Pro Pro Thr Lys Lys Pro Glu Ala Pro Lys Lys Pro
            610                 615                 620 gaa gct gcc caa gat ccc att gat gcc ctc tca ggg gat ttt gac aga      1980
Glu Ala Ala Gln Asp Pro Ile Asp Ala Leu Ser Gly Asp Phe Asp Arg
        625                 630                 635 tgt cca tca act aca gaa acc tca gag aac aca aca aag gac aaa gac      2028
Cys Pro Ser Thr Thr Glu Thr Ser Glu Asn Thr Thr Lys Asp Lys Asp
    640                 645                 650 aag aag acg gct tcc aag tcc aaa gca ccc aag aat ggg ggt aaa gca      2076
Lys Lys Thr Ala Ser Lys Ser Lys Ala Pro Lys Asn Gly Gly Lys Ala
655                 660                 665                 670 aag gat tcc aca aag gca aag gag gaa act tcc aaa caa aaa tct gat      2124
Lys Asp Ser Thr Lys Ala Lys Glu Glu Thr Ser Lys Gln Lys Ser Asp
                675                 680                 685 gga aag agt aca agt taaaagttca cactattttc                            2159
Gly Lys Ser Thr Ser
            690

<210> SEQ ID NO 6
<211> LENGTH: 691
<212> TYPE: PRT
<213> ORGANISM: Sus scrofa

<400> SEQUENCE: 6
```

-continued

```
Met Asn Pro Thr Glu Thr Lys Ala Val Lys Thr Glu Pro Glu Lys Lys
1               5                   10                  15

Ser Gln Ser Thr Lys Pro Ser Val Val His Glu Lys Lys Thr Gln Glu
            20                  25                  30

Val Lys Pro Lys Glu His Pro Glu Pro Lys Ser Leu Pro Thr His Ser
        35                  40                  45

Ala Asp Ala Gly Ser Lys Arg Ala His Lys Glu Lys Ala Val Ser Arg
50                  55                  60

Ser Asn Glu Gln Pro Thr Ser Glu Lys Ser Thr Lys Pro Lys Ala Lys
65                  70                  75                  80

Pro Gln Asp Pro Thr Pro Ser Asp Gly Lys Leu Ser Val Thr Gly Val
                85                  90                  95

Ser Ala Ala Ser Gly Lys Pro Ala Glu Thr Lys Lys Asp Asp Lys Ser
            100                 105                 110

Leu Thr Ser Ser Val Pro Ala Glu Ser Lys Ser Ser Lys Pro Ser Gly
        115                 120                 125

Lys Ser Asp Met Asp Ala Ala Leu Asp Asp Leu Ile Asp Thr Leu Gly
    130                 135                 140

Gly Pro Glu Glu Thr Glu Glu Asp Asn Thr Thr Tyr Thr Gly Pro Glu
145                 150                 155                 160

Val Leu Asp Pro Met Ser Ser Thr Tyr Ile Glu Glu Leu Gly Lys Arg
                165                 170                 175

Glu Val Thr Leu Pro Pro Lys Tyr Arg Glu Leu Leu Asp Lys Lys Glu
            180                 185                 190

Gly Ile Pro Val Pro Pro Asp Thr Ser Lys Pro Leu Gly Pro Asp
    195                 200                 205

Asp Ala Ile Asp Ala Leu Ser Leu Asp Leu Thr Cys Ser Ser Pro Thr
210                 215                 220

Ala Asp Gly Lys Lys Thr Glu Lys Glu Lys Ser Thr Gly Glu Val Leu
225                 230                 235                 240

Lys Ala Gln Ser Val Gly Val Ile Lys Ser Ala Ala Pro Pro His
                245                 250                 255

Glu Lys Lys Arg Arg Val Glu Glu Asp Thr Met Ser Asp Gln Ala Leu
            260                 265                 270

Glu Ala Leu Ser Ala Ser Leu Gly Ser Arg Lys Ser Glu Pro Glu Leu
        275                 280                 285

Asp Leu Ser Ser Ile Lys Glu Ile Asp Glu Ala Lys Ala Lys Glu Glu
    290                 295                 300

Lys Leu Lys Lys Cys Gly Glu Asp Glu Thr Val Pro Pro Glu Tyr
305                 310                 315                 320

Arg Leu Lys Pro Ala Met Asp Lys Asp Gly Lys Pro Leu Leu Pro Glu
                325                 330                 335

Ala Glu Glu Lys Pro Lys Pro Leu Ser Glu Ser Glu Leu Ile Asp Glu
            340                 345                 350

Leu Ser Glu Asp Phe Asp Gln Ser Lys Arg Lys Glu Lys Gln Ser Lys
        355                 360                 365

Pro Thr Glu Lys Thr Lys Glu Ser Gln Ala Thr Ala Pro Thr Pro Val
    370                 375                 380

Gly Glu Ala Val Ser Arg Thr Ser Leu Cys Cys Val Gln Ser Ala Pro
385                 390                 395                 400

Pro Lys Pro Ala Thr Gly Met Val Pro Asp Asp Ala Val Glu Ala Leu
                405                 410                 415

Ala Gly Ser Leu Gly Lys Lys Glu Ala Asp Pro Glu Asp Gly Lys Pro
```

-continued

```
                420                 425                 430
Val Glu Asp Lys Val Lys Glu Lys Ala Lys Glu Asp Arg Glu Lys
        435                 440                 445

Leu Gly Glu Lys Glu Glu Thr Ile Pro Pro Asp Tyr Arg Leu Glu
    450                 455                 460

Val Lys Asp Lys Asp Gly Lys Thr Leu Pro His Lys Asp Pro Lys Glu
465                 470                 475                 480

Pro Val Leu Pro Leu Ser Glu Asp Phe Val Leu Asp Ala Leu Ser Gln
                485                 490                 495

Asp Phe Ala Gly Pro Pro Ala Ala Ser Ser Leu Phe Glu Asp Ala Lys
            500                 505                 510

Leu Ser Ala Ala Val Ser Glu Val Val Ser Gln Thr Ser Ala Pro Thr
        515                 520                 525

Thr His Ser Ala Gly Pro Pro Pro Asp Thr Val Ser Asp Asp Lys Lys
    530                 535                 540

Leu Asp Asp Ala Leu Asp Gln Leu Ser Asp Ser Leu Gly Gln Arg Gln
545                 550                 555                 560

Pro Asp Pro Asp Glu Asn Lys Pro Ile Glu Asp Lys Val Lys Glu Lys
                565                 570                 575

Ala Glu Ala Glu His Arg Asp Lys Leu Gly Glu Arg Asp Asp Thr Ile
            580                 585                 590

Pro Pro Glu Tyr Arg His Leu Leu Asp Lys Asp Glu Glu Gly Lys Ser
        595                 600                 605

Thr Lys Pro Pro Thr Lys Lys Pro Glu Ala Pro Lys Lys Pro Glu Ala
    610                 615                 620

Ala Gln Asp Pro Ile Asp Ala Leu Ser Gly Asp Phe Asp Arg Cys Pro
625                 630                 635                 640

Ser Thr Thr Glu Thr Ser Glu Asn Thr Thr Lys Asp Lys Asp Lys Lys
                645                 650                 655

Thr Ala Ser Lys Ser Lys Ala Pro Lys Asn Gly Gly Lys Ala Lys Asp
            660                 665                 670

Ser Thr Lys Ala Lys Glu Glu Thr Ser Lys Gln Lys Ser Asp Gly Lys
        675                 680                 685

Ser Thr Ser
    690

<210> SEQ ID NO 7
<211> LENGTH: 2159
<212> TYPE: DNA
<213> ORGANISM: Sus scrofa
<220> FEATURE:
<221> NAME/KEY: CDS
<222> LOCATION: (67)..(2139)
<223> OTHER INFORMATION:

<400> SEQUENCE: 7
tctctcggcc gggaagccag aagcagagta tcgccttcct ctgcttcaac gagcaagtct    60 tccagt atg aat ccc aca gaa acc aag gct gta aaa aca gaa cct gaa       108
       Met Asn Pro Thr Glu Thr Lys Ala Val Lys Thr Glu Pro Glu
       1               5                   10 aag aag tca caa tca act aag cca tct gtg gtt cat gag aaa aaa acc     156
Lys Lys Ser Gln Ser Thr Lys Pro Ser Val Val His Glu Lys Lys Thr
15                  20                  25                  30 caa gaa gta aag cca aag gaa cac cca gag cca aaa agc cta ccc acg     204
Gln Glu Val Lys Pro Lys Glu His Pro Glu Pro Lys Ser Leu Pro Thr
                35                  40                  45
```

-continued

| | |
|---|---|
| cac tca gca gat gca ggg agc aag cgt gct cat aaa gaa aaa gca gtt<br>His Ser Ala Asp Ala Gly Ser Lys Arg Ala His Lys Glu Lys Ala Val<br>50      55      60 | 252 |
| tcc aga tct aat gag cag cca aca tca gag aaa tca aca aaa cca aag<br>Ser Arg Ser Asn Glu Gln Pro Thr Ser Glu Lys Ser Thr Lys Pro Lys<br>65      70      75 | 300 |
| gct aaa cca cag gac ccg acc ccc agt gat gga aag ctt tct gtt act<br>Ala Lys Pro Gln Asp Pro Thr Pro Ser Asp Gly Lys Leu Ser Val Thr<br>80      85      90 | 348 |
| ggt gta tct gca gca tct ggc aaa cca gct gag acg aaa aaa gat gat<br>Gly Val Ser Ala Ala Ser Gly Lys Pro Ala Glu Thr Lys Lys Asp Asp<br>95     100     105     110 | 396 |
| aaa tca tta aca tcg tct gta cca gct gaa tcc aaa tca agt aaa cca<br>Lys Ser Leu Thr Ser Ser Val Pro Ala Glu Ser Lys Ser Ser Lys Pro<br>115     120     125 | 444 |
| tca gga aag tca gat atg gat gct gct ttg gat gac tta ata gac act<br>Ser Gly Lys Ser Asp Met Asp Ala Ala Leu Asp Asp Leu Ile Asp Thr<br>130     135     140 | 492 |
| tta gga gga cct gaa gaa act gag gaa gat aat aca aca tat act gga<br>Leu Gly Gly Pro Glu Glu Thr Glu Glu Asp Asn Thr Thr Tyr Thr Gly<br>145     150     155 | 540 |
| cct gaa gtt ttg gat cca atg agt tct acc tat ata gag gaa ttg ggt<br>Pro Glu Val Leu Asp Pro Met Ser Ser Thr Tyr Ile Glu Glu Leu Gly<br>160     165     170 | 588 |
| aaa aga gaa gtc aca ctt cct cca aaa tat agg gaa ttg ttg gat aaa<br>Lys Arg Glu Val Thr Leu Pro Pro Lys Tyr Arg Glu Leu Leu Asp Lys<br>175     180     185     190 | 636 |
| aaa gaa ggg att cca gtg cct cct cca gac act tcg aaa ccc ctg ggg<br>Lys Glu Gly Ile Pro Val Pro Pro Pro Asp Thr Ser Lys Pro Leu Gly<br>195     200     205 | 684 |
| ccc gat gat gcc atc gat gcc ttg tca tta gac ttg acc tgc agt tct<br>Pro Asp Asp Ala Ile Asp Ala Leu Ser Leu Asp Leu Thr Cys Ser Ser<br>210     215     220 | 732 |
| cct aca gct gat ggg aag aaa acc gag aaa gag aaa tct act ggg gag<br>Pro Thr Ala Asp Gly Lys Lys Thr Glu Lys Glu Lys Ser Thr Gly Glu<br>225     230     235 | 780 |
| gtt ttg aaa gct cag tct gtt ggg gta atc aga agc gct gct gct cca<br>Val Leu Lys Ala Gln Ser Val Gly Val Ile Arg Ser Ala Ala Ala Pro<br>240     245     250 | 828 |
| ccc cac gag aaa aaa aga agg gtg gaa gag gac acg atg agt gat caa<br>Pro His Glu Lys Lys Arg Arg Val Glu Glu Asp Thr Met Ser Asp Gln<br>255     260     265     270 | 876 |
| gca ctg gag gct ttg tca gct tcc ctg ggc agc cgg aag tca gaa ccc<br>Ala Leu Glu Ala Leu Ser Ala Ser Leu Gly Ser Arg Lys Ser Glu Pro<br>275     280     285 | 924 |
| gag ctt gac ctc agc tcc att aag gaa att gat gag gca aaa gcc aaa<br>Glu Leu Asp Leu Ser Ser Ile Lys Glu Ile Asp Glu Ala Lys Ala Lys<br>290     295     300 | 972 |
| gaa gag aaa cta aag aag tgt ggt gaa gat gac gaa acg gtc ccg cca<br>Glu Glu Lys Leu Lys Lys Cys Gly Glu Asp Asp Glu Thr Val Pro Pro<br>305     310     315 | 1020 |
| gag tat aga ttg aaa cca gcc atg gat aaa gat gga aaa cca ctc ttg<br>Glu Tyr Arg Leu Lys Pro Ala Met Asp Lys Asp Gly Lys Pro Leu Leu<br>320     325     330 | 1068 |
| cca gag gct gaa gaa aaa ccc aag ccc ctg agt gaa tca gaa ctc att<br>Pro Glu Ala Glu Glu Lys Pro Lys Pro Leu Ser Glu Ser Glu Leu Ile<br>335     340     345     350 | 1116 |
| gac gaa ctt tcg gaa gat ttt gac cag tct aag cgt aaa gaa aaa caa<br>Asp Glu Leu Ser Glu Asp Phe Asp Gln Ser Lys Arg Lys Glu Lys Gln<br>355     360     365 | 1164 |

-continued

| | |
|---|---|
| tct aag cca act gaa aaa aca aaa gag tct cag gcc act gcc cct act<br>Ser Lys Pro Thr Glu Lys Thr Lys Glu Ser Gln Ala Thr Ala Pro Thr<br>370                              375                     380 | 1212 |
| cct gtg gga gag gcc gtg tct cgg acc tcc ttg tgc tgt gtg cag tcg<br>Pro Val Gly Glu Ala Val Ser Arg Thr Ser Leu Cys Cys Val Gln Ser<br>               385                              390                     395 | 1260 |
| gca ccc cca aag cca gct acg ggc atg gtg cca gat gat gct gta gaa<br>Ala Pro Pro Lys Pro Ala Thr Gly Met Val Pro Asp Asp Ala Val Glu<br>400                              405                            410 | 1308 |
| gcc ttg gct gga agc ctg ggg aaa aag gaa gca gat cca gaa gat gga<br>Ala Leu Ala Gly Ser Leu Gly Lys Lys Glu Ala Asp Pro Glu Asp Gly<br>415                           420                     425                     430 | 1356 |
| aag cct gtg gag gat aaa gtc aag gag aaa gcc aaa gaa gag gat cgt<br>Lys Pro Val Glu Asp Lys Val Lys Glu Lys Ala Lys Glu Glu Asp Arg<br>                             435                          440                     445 | 1404 |
| gaa aaa ctt ggt gaa aag gaa gaa acg att cct cct gat tat aga tta<br>Glu Lys Leu Gly Glu Lys Glu Glu Thr Ile Pro Pro Asp Tyr Arg Leu<br>450                              455                            460 | 1452 |
| gaa gag gtc aag gac aaa gat gga aaa act ctc ccg cac aaa gac ccc<br>Glu Glu Val Lys Asp Lys Asp Gly Lys Thr Leu Pro His Lys Asp Pro<br>                         465                            470                     475 | 1500 |
| aag gaa cca gtc ctg ccc ttg agt gaa gac ttc gtc ctt gat gct ttg<br>Lys Glu Pro Val Leu Pro Leu Ser Glu Asp Phe Val Leu Asp Ala Leu<br>480                              485                            490 | 1548 |
| tcc cag gac ttt gcc ggt ccc cca gcc act tca tct ctt ttt gaa gat<br>Ser Gln Asp Phe Ala Gly Pro Pro Ala Thr Ser Ser Leu Phe Glu Asp<br>495                           500                     505                     510 | 1596 |
| gct aaa ctt tca gct gcc gtc tct gaa gtg gtt tcc caa acc tca gct<br>Ala Lys Leu Ser Ala Ala Val Ser Glu Val Val Ser Gln Thr Ser Ala<br>                         515                           520                     525 | 1644 |
| cca acc acc cac tct gca ggt cca ccc cct gac act gtg agt gat gac<br>Pro Thr Thr His Ser Ala Gly Pro Pro Pro Asp Thr Val Ser Asp Asp<br>                             530                           535                     540 | 1692 |
| aaa aaa ctt gac gat gcc ctg gat cag ctt tct gac agt ctg ggg caa<br>Lys Lys Leu Asp Asp Ala Leu Asp Gln Leu Ser Asp Ser Leu Gly Gln<br>545                           550                        555 | 1740 |
| aga cag cct gac cca gat gag aac aag ccc ata gag gat aaa gtc aag<br>Arg Gln Pro Asp Pro Asp Glu Asn Lys Pro Ile Glu Asp Lys Val Lys<br>                         560                           565                     570 | 1788 |
| gaa aaa gct gaa gct gaa cat aga gac aag ctg gga gaa aga gat gac<br>Glu Lys Ala Glu Ala Glu His Arg Asp Lys Leu Gly Glu Arg Asp Asp<br>575                           580                     585                     590 | 1836 |
| act atc ccg cct gaa tat aga cat ctc ttg gat aag gat gag gag ggc<br>Thr Ile Pro Pro Glu Tyr Arg His Leu Leu Asp Lys Asp Glu Glu Gly<br>                         595                           600                     605 | 1884 |
| aaa tca acg aag cca ccc aca aag aaa cct gag gca cca aag aaa cct<br>Lys Ser Thr Lys Pro Pro Thr Lys Lys Pro Glu Ala Pro Lys Lys Pro<br>610                           615                           620 | 1932 |
| gaa gct gcc caa gat ccc att gat gcc ctc tca ggg gat ttt gac aga<br>Glu Ala Ala Gln Asp Pro Ile Asp Ala Leu Ser Gly Asp Phe Asp Arg<br>                         625                           630                     635 | 1980 |
| tgt cca tca act aca gaa acc tca gag aac aca aca aag gac aaa gac<br>Cys Pro Ser Thr Thr Glu Thr Ser Glu Asn Thr Thr Lys Asp Lys Asp<br>640                           645                           650 | 2028 |
| aag aag acg gct tcc aag tcc aaa gca ccc aag aat ggg ggt aaa gca<br>Lys Lys Thr Ala Ser Lys Ser Lys Ala Pro Lys Asn Gly Gly Lys Ala<br>655                           660                     665                     670 | 2076 |
| aag gat tcc aca aag gca aag gag gaa act tcc aaa caa aaa tct gat<br>Lys Asp Ser Thr Lys Ala Lys Glu Glu Thr Ser Lys Gln Lys Ser Asp | 2124 |

-continued

```
                        675                 680                 685
gga aag agt aca agt taaaagttca cactattttc                              2159
Gly Lys Ser Thr Ser
            690

<210> SEQ ID NO 8
<211> LENGTH: 691
<212> TYPE: PRT
<213> ORGANISM: Sus scrofa

<400> SEQUENCE: 8

Met Asn Pro Thr Glu Thr Lys Ala Val Lys Thr Glu Pro Glu Lys Lys
1               5                   10                  15

Ser Gln Ser Thr Lys Pro Ser Val Val His Glu Lys Lys Thr Gln Glu
            20                  25                  30

Val Lys Pro Lys Glu His Pro Glu Pro Lys Ser Leu Pro Thr His Ser
        35                  40                  45

Ala Asp Ala Gly Ser Lys Arg Ala His Lys Glu Lys Ala Val Ser Arg
    50                  55                  60

Ser Asn Glu Gln Pro Thr Ser Glu Lys Ser Thr Lys Pro Lys Ala Lys
65                  70                  75                  80

Pro Gln Asp Pro Thr Pro Ser Asp Gly Lys Leu Ser Val Thr Gly Val
                85                  90                  95

Ser Ala Ala Ser Gly Lys Pro Ala Glu Thr Lys Lys Asp Asp Lys Ser
            100                 105                 110

Leu Thr Ser Ser Val Pro Ala Glu Ser Lys Ser Ser Lys Pro Ser Gly
        115                 120                 125

Lys Ser Asp Met Asp Ala Ala Leu Asp Asp Leu Ile Asp Thr Leu Gly
    130                 135                 140

Gly Pro Glu Glu Thr Glu Glu Asp Asn Thr Thr Tyr Thr Gly Pro Glu
145                 150                 155                 160

Val Leu Asp Pro Met Ser Ser Thr Tyr Ile Glu Glu Leu Gly Lys Arg
                165                 170                 175

Glu Val Thr Leu Pro Pro Lys Tyr Arg Glu Leu Leu Asp Lys Lys Glu
            180                 185                 190

Gly Ile Pro Val Pro Pro Asp Thr Ser Lys Pro Leu Gly Pro Asp
        195                 200                 205

Asp Ala Ile Asp Ala Leu Ser Leu Asp Leu Thr Cys Ser Ser Pro Thr
    210                 215                 220

Ala Asp Gly Lys Lys Thr Glu Lys Glu Lys Ser Thr Gly Glu Val Leu
225                 230                 235                 240

Lys Ala Gln Ser Val Gly Val Ile Arg Ser Ala Ala Pro His
                245                 250                 255

Glu Lys Lys Arg Arg Val Glu Glu Asp Thr Met Ser Asp Gln Ala Leu
            260                 265                 270

Glu Ala Leu Ser Ala Ser Leu Gly Ser Arg Lys Ser Glu Pro Glu Leu
        275                 280                 285

Asp Leu Ser Ser Ile Lys Glu Ile Asp Glu Ala Lys Ala Lys Glu Glu
    290                 295                 300

Lys Leu Lys Lys Cys Gly Glu Asp Glu Thr Val Pro Pro Glu Tyr
305                 310                 315                 320

Arg Leu Lys Pro Ala Met Asp Lys Asp Gly Lys Pro Leu Leu Pro Glu
                325                 330                 335

Ala Glu Glu Lys Pro Lys Pro Leu Ser Glu Ser Glu Leu Ile Asp Glu
            340                 345                 350
```

```
Leu Ser Glu Asp Phe Asp Gln Ser Lys Arg Lys Glu Lys Gln Ser Lys
        355                 360                 365

Pro Thr Glu Lys Thr Lys Glu Ser Gln Ala Thr Ala Pro Thr Pro Val
    370                 375                 380

Gly Glu Ala Val Ser Arg Thr Ser Leu Cys Cys Val Gln Ser Ala Pro
385                 390                 395                 400

Pro Lys Pro Ala Thr Gly Met Val Pro Asp Asp Ala Val Glu Ala Leu
                405                 410                 415

Ala Gly Ser Leu Gly Lys Lys Glu Ala Asp Pro Glu Asp Gly Lys Pro
            420                 425                 430

Val Glu Asp Lys Val Lys Glu Lys Ala Lys Glu Glu Asp Arg Glu Lys
        435                 440                 445

Leu Gly Glu Lys Glu Glu Thr Ile Pro Pro Asp Tyr Arg Leu Glu Glu
    450                 455                 460

Val Lys Asp Lys Asp Gly Lys Thr Leu Pro His Lys Asp Pro Lys Glu
465                 470                 475                 480

Pro Val Leu Pro Leu Ser Glu Asp Phe Val Leu Asp Ala Leu Ser Gln
                485                 490                 495

Asp Phe Ala Gly Pro Pro Ala Thr Ser Ser Leu Phe Glu Asp Ala Lys
            500                 505                 510

Leu Ser Ala Ala Val Ser Glu Val Val Ser Gln Thr Ser Ala Pro Thr
        515                 520                 525

Thr His Ser Ala Gly Pro Pro Pro Asp Thr Val Ser Asp Asp Lys Lys
    530                 535                 540

Leu Asp Asp Ala Leu Asp Gln Leu Ser Asp Ser Leu Gly Gln Arg Gln
545                 550                 555                 560

Pro Asp Pro Asp Glu Asn Lys Pro Ile Glu Asp Lys Val Lys Glu Lys
                565                 570                 575

Ala Glu Ala Glu His Arg Asp Lys Leu Gly Glu Arg Asp Asp Thr Ile
            580                 585                 590

Pro Pro Glu Tyr Arg His Leu Leu Asp Lys Asp Glu Glu Gly Lys Ser
        595                 600                 605

Thr Lys Pro Pro Thr Lys Lys Pro Glu Ala Pro Lys Lys Pro Glu Ala
    610                 615                 620

Ala Gln Asp Pro Ile Asp Ala Leu Ser Gly Asp Phe Asp Arg Cys Pro
625                 630                 635                 640

Ser Thr Thr Glu Thr Ser Glu Asn Thr Thr Lys Asp Lys Asp Lys Lys
                645                 650                 655

Thr Ala Ser Lys Ser Lys Ala Pro Lys Asn Gly Gly Lys Ala Lys Asp
            660                 665                 670

Ser Thr Lys Ala Lys Glu Glu Thr Ser Lys Gln Lys Ser Asp Gly Lys
        675                 680                 685

Ser Thr Ser
    690

<210> SEQ ID NO 9
<211> LENGTH: 2159
<212> TYPE: DNA
<213> ORGANISM: Sus scrofa
<220> FEATURE:
<221> NAME/KEY: CDS
<222> LOCATION: (67)..(2139)
<223> OTHER INFORMATION:

<400> SEQUENCE: 9
```

-continued

```
tctctcggcc gggaagccag aagcagagta tcgccttcct ctgcttcaac gagcaagtct      60 tccagt atg aat ccc aca gaa acc aag gct gta aaa aca gaa cct gaa        108
       Met Asn Pro Thr Glu Thr Lys Ala Val Lys Thr Glu Pro Glu
       1               5                   10 aag aag tca caa tca act aag cca tct gtg gtt cat gag aaa aaa acc      156
Lys Lys Ser Gln Ser Thr Lys Pro Ser Val Val His Glu Lys Lys Thr
15                  20                  25                  30 caa gaa gta aag cca aag gaa cac cca gag cca aaa agc cta ccc acg      204
Gln Glu Val Lys Pro Lys Glu His Pro Glu Pro Lys Ser Leu Pro Thr
                35                  40                  45 cac tca gca gat gca ggg agc aag cgt gct cat aaa gaa aaa gca gtt      252
His Ser Ala Asp Ala Gly Ser Lys Arg Ala His Lys Glu Lys Ala Val
            50                  55                  60 tcc aga tct aat gag cag cca aca tca gag aaa tca aca aaa cca aag      300
Ser Arg Ser Asn Glu Gln Pro Thr Ser Glu Lys Ser Thr Lys Pro Lys
65                  70                  75 gct aaa cca cag gac ccg acc ccc agt gat gga aag ctt tct gtt act      348
Ala Lys Pro Gln Asp Pro Thr Pro Ser Asp Gly Lys Leu Ser Val Thr
    80                  85                  90 ggt gta tct gca gca tct ggc aaa cca gct gag acg aaa aaa gat gat      396
Gly Val Ser Ala Ala Ser Gly Lys Pro Ala Glu Thr Lys Lys Asp Asp
95                  100                 105                 110 aaa tca tta aca tcg tct gta cca gct gaa tcc aaa tca agt aaa cca      444
Lys Ser Leu Thr Ser Ser Val Pro Ala Glu Ser Lys Ser Ser Lys Pro
                115                 120                 125 tca gga aag tca gat atg gat gct gct ttg gat gac tta ata gac act      492
Ser Gly Lys Ser Asp Met Asp Ala Ala Leu Asp Asp Leu Ile Asp Thr
            130                 135                 140 tta gga gga cct gaa gaa act gag gaa gat aat aca aca tat act gga      540
Leu Gly Gly Pro Glu Glu Thr Glu Glu Asp Asn Thr Thr Tyr Thr Gly
145                 150                 155 cct gaa gtt ttg gat cca atg agt tct acc tat ata gag gaa ttg ggt      588
Pro Glu Val Leu Asp Pro Met Ser Ser Thr Tyr Ile Glu Glu Leu Gly
    160                 165                 170 aaa aga gaa gtc aca ctt cct cca aaa tat agg gaa ttg ttg gat aaa      636
Lys Arg Glu Val Thr Leu Pro Pro Lys Tyr Arg Glu Leu Leu Asp Lys
175                 180                 185                 190 aaa gaa ggg att cca gtg cct cct cca gac act tcg aaa ccc ctg ggg      684
Lys Glu Gly Ile Pro Val Pro Pro Pro Asp Thr Ser Lys Pro Leu Gly
                195                 200                 205 ccc gat gat gcc atc gat gcc ttg tca tta gac ttg acc tgc agt tct      732
Pro Asp Asp Ala Ile Asp Ala Leu Ser Leu Asp Leu Thr Cys Ser Ser
            210                 215                 220 cct aca gct gat ggg aag aaa acc gag aaa gag aaa tct act ggg gag      780
Pro Thr Ala Asp Gly Lys Lys Thr Glu Lys Glu Lys Ser Thr Gly Glu
225                 230                 235 gtt ttg aaa gct cag tct gtt ggg gta atc aga agc gct gct gct cca      828
Val Leu Lys Ala Gln Ser Val Gly Val Ile Arg Ser Ala Ala Ala Pro
    240                 245                 250 ccc cac gag aaa aaa aga agg gtg gaa gag gac acg atg agt gat caa      876
Pro His Glu Lys Lys Arg Arg Val Glu Glu Asp Thr Met Ser Asp Gln
255                 260                 265                 270 gca ctg gag gct ttg tca gct tcc ctg ggc agc cgg aag tca gaa ccc      924
Ala Leu Glu Ala Leu Ser Ala Ser Leu Gly Ser Arg Lys Ser Glu Pro
                275                 280                 285 gag ctt gac ctc agc tcc att aag gaa att gat gag gca aaa gcc aaa      972
Glu Leu Asp Leu Ser Ser Ile Lys Glu Ile Asp Glu Ala Lys Ala Lys
            290                 295                 300 gaa gag aaa cta aag aag tgt ggt gaa gat gac gaa acg gtc ccg cca     1020
```

```
            Glu Glu Lys Leu Lys Lys Cys Gly Glu Asp Asp Glu Thr Val Pro Pro
                    305                 310                 315 gag tat aga ttg aaa cca gcc atg gat aaa gat gga aaa cca ctc ttg          1068
Glu Tyr Arg Leu Lys Pro Ala Met Asp Lys Asp Gly Lys Pro Leu Leu
320                 325                 330 cca gag gct gaa gaa aaa ccc aag ccc ctg agt gaa tca gaa ctc att          1116
Pro Glu Ala Glu Glu Lys Pro Lys Pro Leu Ser Glu Ser Glu Leu Ile
335                 340                 345                 350 gac gaa ctt tcg gaa gat ttt gac cag tct aag cgt aaa gaa aaa caa          1164
Asp Glu Leu Ser Glu Asp Phe Asp Gln Ser Lys Arg Lys Glu Lys Gln
                    355                 360                 365 tct aag cca act gaa aaa aca aaa gag tct cag gcc act gcc cct act          1212
Ser Lys Pro Thr Glu Lys Thr Lys Glu Ser Gln Ala Thr Ala Pro Thr
                370                 375                 380 cct gtg gga gag gcc gtg tct cgg acc tcc ttg tgc tgt gtg cag tcg          1260
Pro Val Gly Glu Ala Val Ser Arg Thr Ser Leu Cys Cys Val Gln Ser
            385                 390                 395 gca ccc cca aag cca gct acg ggc atg gtg cca gat gat gct gta gaa          1308
Ala Pro Pro Lys Pro Ala Thr Gly Met Val Pro Asp Asp Ala Val Glu
        400                 405                 410 gcc ttg gct gga agc ctg ggg aaa aag gaa gca gat cca gaa gat gga          1356
Ala Leu Ala Gly Ser Leu Gly Lys Lys Glu Ala Asp Pro Glu Asp Gly
415                 420                 425                 430 aag cct gtg gag gat aaa gtc aag gag aaa gcc aaa gaa gag gat cgt          1404
Lys Pro Val Glu Asp Lys Val Lys Glu Lys Ala Lys Glu Glu Asp Arg
                    435                 440                 445 gaa aaa ctt ggt gaa aag gaa gaa acg att cct cct gat tat aga tta          1452
Glu Lys Leu Gly Glu Lys Glu Glu Thr Ile Pro Pro Asp Tyr Arg Leu
                450                 455                 460 gaa gag gtc aag gac aaa gat gga aaa act ctc ccg cac aaa gac ccc          1500
Glu Glu Val Lys Asp Lys Asp Gly Lys Thr Leu Pro His Lys Asp Pro
            465                 470                 475 aag gaa cca gtc ctg ccc ttg agt gaa gac ttc gtc ctt gat gct ttg          1548
Lys Glu Pro Val Leu Pro Leu Ser Glu Asp Phe Val Leu Asp Ala Leu
        480                 485                 490 tcc cag gac ttt gcc ggt ccc cca gcc gct tca tct ctt ttt gaa gat          1596
Ser Gln Asp Phe Ala Gly Pro Pro Ala Ala Ser Ser Leu Phe Glu Asp
495                 500                 505                 510 gct aaa ctt tca gct gcc gtc tct gaa gtg gtt tcc caa acc tca gct          1644
Ala Lys Leu Ser Ala Ala Val Ser Glu Val Val Ser Gln Thr Ser Ala
                    515                 520                 525 cca acc acc cac tct gca ggt cca ccc cct gac act gtg agt gat gac          1692
Pro Thr Thr His Ser Ala Gly Pro Pro Pro Asp Thr Val Ser Asp Asp
                530                 535                 540 aaa aaa ctt gac gat gcc ctg gat cag ctt tct gac agt ctg ggg caa          1740
Lys Lys Leu Asp Asp Ala Leu Asp Gln Leu Ser Asp Ser Leu Gly Gln
            545                 550                 555 aga cag cct gac cca gat gag aac aag ccc ata gag gat aaa gtc aag          1788
Arg Gln Pro Asp Pro Asp Glu Asn Lys Pro Ile Glu Asp Lys Val Lys
        560                 565                 570 gaa aaa gct gaa gct gaa cat aga gac aag ctg gga gaa aga gat gac          1836
Glu Lys Ala Glu Ala Glu His Arg Asp Lys Leu Gly Glu Arg Asp Asp
575                 580                 585                 590 act atc ccg cct gaa tat aga cat ctc ttg gat aag gat gag gag ggc          1884
Thr Ile Pro Pro Glu Tyr Arg His Leu Leu Asp Lys Asp Glu Glu Gly
                    595                 600                 605 aaa tca acg aag cca ccc aca aag aaa cct gag gca cca aag aaa cct          1932
Lys Ser Thr Lys Pro Pro Thr Lys Lys Pro Glu Ala Pro Lys Lys Pro
                610                 615                 620
```

```
gaa gct gcc caa gat ccc att gat gcc ctc tca ggg gat ttt gac agc      1980
Glu Ala Ala Gln Asp Pro Ile Asp Ala Leu Ser Gly Asp Phe Asp Ser
            625                 630                 635 tgt cca tca act aca gaa acc tca gag aac aca aca aag gac aaa gac      2028
Cys Pro Ser Thr Thr Glu Thr Ser Glu Asn Thr Thr Lys Asp Lys Asp
640                 645                 650 aag aag acg gct tcc aag tcc aaa gca ccc aag aat ggg ggt aaa gca      2076
Lys Lys Thr Ala Ser Lys Ser Lys Ala Pro Lys Asn Gly Gly Lys Ala
655                 660                 665                 670 aag gat tcc aca aag gca aag gag gaa act tcc aaa caa aaa tct gat      2124
Lys Asp Ser Thr Lys Ala Lys Glu Glu Thr Ser Lys Gln Lys Ser Asp
            675                 680                 685 gga aag agt aca agt taaaagttca cactattttc                            2159
Gly Lys Ser Thr Ser
            690
```

<210> SEQ ID NO 10
<211> LENGTH: 691
<212> TYPE: PRT
<213> ORGANISM: Sus scrofa

<400> SEQUENCE: 10

```
Met Asn Pro Thr Glu Thr Lys Ala Val Lys Thr Glu Pro Glu Lys Lys
1               5                   10                  15

Ser Gln Ser Thr Lys Pro Ser Val Val His Glu Lys Lys Thr Gln Glu
            20                  25                  30

Val Lys Pro Lys Glu His Pro Glu Pro Lys Ser Leu Pro Thr His Ser
        35                  40                  45

Ala Asp Ala Gly Ser Lys Arg Ala His Lys Glu Lys Ala Val Ser Arg
    50                  55                  60

Ser Asn Glu Gln Pro Thr Ser Glu Lys Ser Thr Lys Pro Lys Ala Lys
65                  70                  75                  80

Pro Gln Asp Pro Thr Pro Ser Asp Gly Lys Leu Ser Val Thr Gly Val
                85                  90                  95

Ser Ala Ala Ser Gly Lys Pro Ala Glu Thr Lys Lys Asp Asp Lys Ser
            100                 105                 110

Leu Thr Ser Ser Val Pro Ala Glu Ser Lys Ser Ser Lys Pro Ser Gly
        115                 120                 125

Lys Ser Asp Met Asp Ala Ala Leu Asp Asp Leu Ile Asp Thr Leu Gly
    130                 135                 140

Gly Pro Glu Glu Thr Glu Glu Asp Asn Thr Thr Tyr Thr Gly Pro Glu
145                 150                 155                 160

Val Leu Asp Pro Met Ser Ser Thr Tyr Ile Glu Glu Leu Gly Lys Arg
                165                 170                 175

Glu Val Thr Leu Pro Pro Lys Tyr Arg Glu Leu Leu Asp Lys Lys Glu
            180                 185                 190

Gly Ile Pro Val Pro Pro Asp Thr Ser Lys Pro Leu Gly Pro Asp
        195                 200                 205

Asp Ala Ile Asp Ala Leu Ser Leu Asp Leu Thr Cys Ser Ser Pro Thr
    210                 215                 220

Ala Asp Gly Lys Lys Thr Glu Lys Glu Lys Ser Thr Gly Glu Val Leu
225                 230                 235                 240

Lys Ala Gln Ser Val Gly Val Ile Arg Ser Ala Ala Pro Pro His
                245                 250                 255

Glu Lys Lys Arg Arg Val Glu Glu Asp Thr Met Ser Asp Gln Ala Leu
            260                 265                 270
```

-continued

```
Glu Ala Leu Ser Ala Ser Leu Gly Ser Arg Lys Ser Glu Pro Glu Leu
        275                 280                 285

Asp Leu Ser Ser Ile Lys Glu Ile Asp Glu Ala Lys Ala Lys Glu Glu
    290                 295                 300

Lys Leu Lys Lys Cys Gly Glu Asp Asp Glu Thr Val Pro Pro Glu Tyr
305                 310                 315                 320

Arg Leu Lys Pro Ala Met Asp Lys Asp Gly Lys Pro Leu Leu Pro Glu
                325                 330                 335

Ala Glu Glu Lys Pro Lys Pro Leu Ser Glu Ser Glu Leu Ile Asp Glu
            340                 345                 350

Leu Ser Glu Asp Phe Asp Gln Ser Lys Arg Lys Glu Lys Gln Ser Lys
        355                 360                 365

Pro Thr Glu Lys Thr Lys Glu Ser Gln Ala Thr Ala Pro Thr Pro Val
    370                 375                 380

Gly Glu Ala Val Ser Arg Thr Ser Leu Cys Cys Val Gln Ser Ala Pro
385                 390                 395                 400

Pro Lys Pro Ala Thr Gly Met Val Pro Asp Asp Ala Val Glu Ala Leu
                405                 410                 415

Ala Gly Ser Leu Gly Lys Lys Glu Ala Asp Pro Glu Asp Gly Lys Pro
            420                 425                 430

Val Glu Asp Lys Val Lys Glu Lys Ala Lys Glu Glu Asp Arg Glu Lys
        435                 440                 445

Leu Gly Glu Lys Glu Glu Thr Ile Pro Pro Asp Tyr Arg Leu Glu Glu
    450                 455                 460

Val Lys Asp Lys Asp Gly Lys Thr Leu Pro His Lys Asp Pro Lys Glu
465                 470                 475                 480

Pro Val Leu Pro Leu Ser Glu Asp Phe Val Leu Asp Ala Leu Ser Gln
                485                 490                 495

Asp Phe Ala Gly Pro Pro Ala Ala Ser Ser Leu Phe Glu Asp Ala Lys
            500                 505                 510

Leu Ser Ala Ala Val Ser Glu Val Val Ser Gln Thr Ser Ala Pro Thr
        515                 520                 525

Thr His Ser Ala Gly Pro Pro Asp Thr Val Ser Asp Asp Lys Lys
    530                 535                 540

Leu Asp Asp Ala Leu Asp Gln Leu Ser Asp Ser Leu Gly Gln Arg Gln
545                 550                 555                 560

Pro Asp Pro Asp Glu Asn Lys Pro Ile Glu Asp Lys Val Lys Glu Lys
                565                 570                 575

Ala Glu Ala Glu His Arg Asp Lys Leu Gly Glu Arg Asp Asp Thr Ile
            580                 585                 590

Pro Pro Glu Tyr Arg His Leu Leu Asp Lys Asp Glu Glu Gly Lys Ser
        595                 600                 605

Thr Lys Pro Pro Thr Lys Lys Pro Glu Ala Pro Lys Lys Pro Glu Ala
    610                 615                 620

Ala Gln Asp Pro Ile Asp Ala Leu Ser Gly Asp Phe Asp Ser Cys Pro
625                 630                 635                 640

Ser Thr Thr Glu Thr Ser Glu Asn Thr Thr Lys Asp Lys Asp Lys Lys
                645                 650                 655

Thr Ala Ser Lys Ser Lys Ala Pro Lys Asn Gly Gly Lys Ala Lys Asp
            660                 665                 670

Ser Thr Lys Ala Lys Glu Glu Thr Ser Lys Gln Lys Ser Asp Gly Lys
        675                 680                 685

Ser Thr Ser
```

<210> SEQ ID NO 11
<211> LENGTH: 23
<212> TYPE: DNA
<213> ORGANISM: synthetic

<400> SEQUENCE: 11
aaatctactg gagaggtttt gaa                                             23

<210> SEQ ID NO 12
<211> LENGTH: 21
<212> TYPE: DNA
<213> ORGANISM: synthetic

<400> SEQUENCE: 12
gacttctccc gaatcagttc c                                               21

<210> SEQ ID NO 13
<211> LENGTH: 21
<212> TYPE: DNA
<213> ORGANISM: synthetic

<400> SEQUENCE: 13
agggcaaatc aacgaagcca c                                               21

<210> SEQ ID NO 14
<211> LENGTH: 21
<212> TYPE: DNA
<213> ORGANISM: synthetic

<400> SEQUENCE: 14
cctttgttgt gttctctgag g                                               21

<210> SEQ ID NO 15
<211> LENGTH: 22
<212> TYPE: DNA
<213> ORGANISM: synthetic

<400> SEQUENCE: 15
agacttcgtc cttgatgctt tg                                              22

<210> SEQ ID NO 16
<211> LENGTH: 22
<212> TYPE: DNA
<213> ORGANISM: synthetic

<400> SEQUENCE: 16
taatggctat gatgggttga gg                                              22

<210> SEQ ID NO 17
<211> LENGTH: 22
<212> TYPE: DNA
<213> ORGANISM: synthetic

<400> SEQUENCE: 17
gtaaagccaa aggaacaccc ag                                              22

<210> SEQ ID NO 18
<211> LENGTH: 28
<212> TYPE: DNA
<213> ORGANISM: synthetic

<400> SEQUENCE: 18

-continued tttttatttc tctgatgttg gctgtgca                                              28

<210> SEQ ID NO 19
<211> LENGTH: 114
<212> TYPE: DNA
<213> ORGANISM: Bos taurus

<400> SEQUENCE: 19
ccaaaaagcc tacccaagca ctcatcagat acaggaagca agcatgctcc taaggaaaaa          60
gccgtttcca aatcaagyga gcagccacca tcagagaaat caacaaaacc aaag              114

<210> SEQ ID NO 20
<211> LENGTH: 164
<212> TYPE: DNA
<213> ORGANISM: Sus scrofa

<400> SEQUENCE: 20
agccatctgt ggttcatgag aaaaaaaccc aagaagtaaa gccaaaggaa cacccagagc          60
caaaaagcct acccacgcac tcagcagatg cagggagcaa gcgtgctcat aaagaaaaag        120
cagtttccag atctartgag cagccaacat cagagaaatc aaca                         164

<210> SEQ ID NO 21
<211> LENGTH: 399
<212> TYPE: DNA
<213> ORGANISM: Sus scrofa

<400> SEQUENCE: 21
aaatctactg gagaggtttt gaaagctcag tctgttgggg taatcaaaag cgctgctgct          60
ccaccccacg agaaaaaaag aagggtggaa gaggtataaa tcattacttc tttgcaacga        120
agcatggtcc gcctgacagc agatgctttc ctgaggctta tggaactgat tcgggagaag        180
tccgattgtg catcacactt gatgagtgtc tttgcgctcc tggtcctgtg tggagtagtg        240
aaaccagtca gggttcactc ggtcatctcc aggcaggcct tctctttctg caaatgcttg        300
tgggtgattt cagcacactt gccttgattg tggagtaaga ctatctcaag attctactgc        360
tcagaagggc aggaccccag agcagctgca ctcttgctt                                399

<210> SEQ ID NO 22
<211> LENGTH: 539
<212> TYPE: DNA
<213> ORGANISM: Sus scrofa

<400> SEQUENCE: 22
agggcaaatc aacgaagcca cccacaaaga aacctgaggc accaaaggta aatactttt           60 ttacactctt gctgcaactc ttaaattta gaaatagaaa atttattgaa ttcttacctt          120
gtgctttatg atcccaaagg gtttgtataa gaatgtatta tttctgtttt cccgagagcc        180
attcaagata ggcagttcca ttttccagat tagaaaattg aagctgagyg aatactaagc        240
aatttgtata aaagagtaga agaaaataga gctgtcaaga ttttcctgtt ttaatatctc        300
ttttgtaata cactactttg ttaggaaagg aatgacagca aggctttatt ttaaacaaac        360
ctattttcag ggatatggga aaatatccca cagagcattc tctcctttgc ctcttcattg        420
atggccattt ctattaatat ctcagaaacc tgaagctgcc caagatccca ttgatgccct        480
ctcaggggat tttgacagat gtccatcaac tacagaaacc tcagagaaca caacaaagg        539

<210> SEQ ID NO 23

```
-continued

<211> LENGTH: 195
<212> TYPE: DNA
<213> ORGANISM: Sus scrofa

<400> SEQUENCE: 23
agacttcgtc cttgatgctt tgtcccagga ctttgccggt cccccagccg cttcatctct      60
tgtaagtctt tggagattcc tggtttaatt tccttagttt tagagtagca cgaaatagat     120
ggaaacttgg gacttagaat ctgatgtggg agctgaggaa acaaaattaa tggccctcaa     180
cccatcatag ccatt                                                     195

<210> SEQ ID NO 24
<211> LENGTH: 164
<212> TYPE: DNA
<213> ORGANISM: Sus scrofa

<400> SEQUENCE: 24
agccatctgt ggttcatgag aaaaaaaccc aagaagtaaa gccaaaggaa cacccagagc      60
caaaaagcct acccacgcac tcagcagatg cagggagcaa gcgtgctcat aaagaaaaag     120
cagtttccag atctartgag cagccaacat cagagaaatc aaca                     164

<210> SEQ ID NO 25
<211> LENGTH: 164
<212> TYPE: DNA
<213> ORGANISM: Sus scrofa

<400> SEQUENCE: 25
agccatctgt ggttcatgag aaaaaaaccc aagaagtaaa gccaaaggaa cacccagagc      60
caaaaagcct acccacgcac tcagcagatg cagggagcaa gcgtgctcat aaagaaaaag     120
cagtttccag atctartgca cagccaacat cagagaaata aaaa                     164
```